US010729758B2

(12) United States Patent
Osorio et al.

(10) Patent No.: US 10,729,758 B2
(45) Date of Patent: Aug. 4, 2020

(54) BROADLY REACTIVE MOSAIC PEPTIDE FOR INFLUENZA VACCINE

(71) Applicant: Wisconsin Alumni Research Foundation, Madison, WI (US)

(72) Inventors: Jorge E. Osorio, Mount Horeb, WI (US); Tony Goldberg, Madison, WI (US); Attapon Kamlangdee, Madison, WI (US); Brock Adam Kingstad-Bakke, Madison, WI (US); Tavis Anderson, Statesboro, GA (US)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 0 days.

(21) Appl. No.: 14/735,911

(22) Filed: Jun. 10, 2015

(65) Prior Publication Data

US 2015/0352202 A1 Dec. 10, 2015

Related U.S. Application Data

(63) Continuation of application No. 14/207,123, filed on Mar. 12, 2014, now abandoned.

(60) Provisional application No. 61/785,071, filed on Mar. 14, 2013.

(51) Int. Cl.

| | |
|---|---|
| ***A61K 39/145*** | (2006.01) |
| ***A61K 45/06*** | (2006.01) |
| ***C12N 7/00*** | (2006.01) |
| ***C07K 14/005*** | (2006.01) |
| ***A61K 39/12*** | (2006.01) |
| *A61K 39/00* | (2006.01) |

(52) U.S. Cl.

CPC ............ *A61K 39/145* (2013.01); *A61K 39/12* (2013.01); *A61K 45/06* (2013.01); *C07K 14/005* (2013.01); *C12N 7/00* (2013.01); *A61K 2039/5256* (2013.01); *A61K 2039/58* (2013.01); *C12N 2710/24143* (2013.01); *C12N 2760/16034* (2013.01); *C12N 2760/16122* (2013.01); *C12N 2760/16134* (2013.01); *C12N 2760/16222* (2013.01)

(58) Field of Classification Search

None

See application file for complete search history.

(56) References Cited

U.S. PATENT DOCUMENTS

| | | | |
|---|---|---|---|
| 6,440,422 | B1 | 8/2002 | Sutter et al. |
| 7,981,428 | B2 | 7/2011 | Wong et al. |
| 2014/0286981 | A1 | 9/2014 | Osorio et al. |

FOREIGN PATENT DOCUMENTS

| | | | |
|---|---|---|---|
| WO | WO-2008/073161 A2 | | 6/2008 |
| WO | WO/10/006144 | * | 1/2010 |
| WO | WO-2012/042279 A2 | | 4/2012 |
| WO | WO-2012/089833 A2 | | 7/2012 |
| WO | WO-2013/148164 A1 | | 10/2013 |

OTHER PUBLICATIONS

Amorij et al., Development of Stable Influenza Vaccine Powder Formulations: Challenges and Possibilities, 2008, Pharmaceutical Research, vol. 25, No. 6, pp. 1256-1273.*

Genbank Accession # ACO36364, hemagglutinin [Influenza A virus (A/Managua/3616.01/2007(H3N2))], Mar. 2009.*

"Genbank EU195416", (Mar. 12, 2010), 2 pgs.

"Genbank EU124163", (May 1, 2008), 2 pgs.

"U.S. Appl. No. 14/207,123, Non Final Office Action dated Feb. 10, 2015", 10 pgs.

"U.S. Appl. No. 14/207,123, Response filed Dec. 4, 2014 to Restriction Requirement dated Sep. 26, 2014", 7 pgs.

"U.S. Appl. No. 14/207,123, Restriction Requirement dated Sep. 26, 2014", 11 pgs.

Hessel, Annett, et al., "Vectors Based on Modified Vaccinia Ankara Expressing Influenza H5N1 Hemagglutinin Induce Substantial Cross-Clade Protective Immunity", *PLoS One*, 6(1): e16247. (Jan. 2011), 1-13.

* cited by examiner

*Primary Examiner* — Benjamin P Blumel

(74) *Attorney, Agent, or Firm* — Schwegman Lundberg & Woessner, P.A.

(57) ABSTRACT

The invention provides for mosaic influenza virus HA and NA sequences and uses thereof.

9 Claims, 47 Drawing Sheets

Specification includes a Sequence Listing.

TO FIG. 2B

MICRONEUTRALIZATION TEST

LUNG VIRAL TITER

Lung titer (VN/1203/04)

| Group | Mouse 1 | Mouse 2 |
|---|---|---|
| H5M/VN | — | — |
| Inactivated/VN | 3.16E+06 | 5.62E+04 |
| MVA/VN | 1.78E+07 | 5.62E+05 |

Lung titer (MONG/244/05)

| | Mouse 1 | Mouse 2 |
|---|---|---|
| H5M/Mg | — | — |
| Inactivated/Mg | 3.16E+02 | 3.16E+02 |
| MVA/Mg | 1.00E+03 | 1.00E+03 |

LUNG VIRAL TITER (TCID50)

HISTOPATHOLOGY

A/VIETNAM/12032004-CHALLENGED

HISTOPATHOLOGY

A/WHOOPER SWAN/MONGOLIA/244/2005-CHALLENGED

HISTOPATHOLOGY

A/HUMAN/HONG KONG/483/1997-CHALLENGED

H1 subtype.

MKVKLLVLLCTFTATYADTICIGYHANNSTDTVDTVLEKNVTVTHSVNLL
EDSHNGKLCLLKGIAPLQLGNCSVAGWILGNPECELLISKESWSYIVEKP
NPENGTCYPGHFADYEELREQLSSVSSFERFEIFPKESSWPNHTVTGVSA
SCSHNGESSFYRNLLWLTGKNGLYPNLSKSYANNKEKEVLVLWGVHHPPN
IGDQRALYHTENAYVSVVSSHYSRKFTPEIAKRPKVRDQEGRINYYWTLL
EPGDTIIFEANGNLIAPRYAFALSRGFGSGIINSNAPMDKCDAKCQTPQG
AINSSLPFQNVHPVTIGECPKYVRSAKLRMVTGLRNIPSIQSRGLFGAIA
GFIEGGWTGMVDGWYGYHHQNEQGSGYAADQKSTQNAINGITNKVNSVIE
KMNTQFTAVGKEFNKLERRMENLNKKVDDGFLDVWTYNAELLVLLENERT
LDFHDSNVKNLYEKVKSQLKNNAKEIGNGCFEFYHKCNDECMESVKNGTY
DYPKYSEESKLNREKIDGVKLESMGVYQILAIYSTVASSLVLLVSLGAIS
FWMCSNGSLQCRICIKN (SEQ ID NO:2)

MKAILVVLLYTFATANADTLCIGYHANNSTDTVDTILEKNVTVTHSVNLL
EDKHNGKLCKLRGVAPLHLGKCNIAGWILGNPECESLSTASSWSYIVETS
SSDNGTCYPGDFIDYEELREQLSSISSFERFEIFPKTSSWPNHDSNKGVT
AACPHAGAKSFYKNLIWLVKKGNSYPKLSKSYINDKGKEVLVLWGIHHPS
TSADQQSLYQNADAYVFVGTSRYSKKFKPEIAIRPKVRDQEGRMNYYWTL
VEPGDKITFEATGNLVVPRYAFAMERNAGSGIIISDTPVHDCNTTCQTPK
GAINTSLPFQNIHPITIGKCPKYVKSTKLRLATGLRNVPSIQSRGLFGAI
AGFIEGGWTGMIDGWYGYHHQNEQGSGYAADLKSTQNAIDEITNKVNSVI
EKMNTQFTAVGKEFNHLEKRIENLNKKVDDGFLDIWTYNAELLVLLENER
TLDYHDSNVKNLYEKVRSQLKNNAKEIGNGCFEFYHKCDNTCMESVKNGT
YDYPKYSEEAKLNREEIDGVKLESTRIYQILAIYSTVASSLVLVVSLGAI
SFWMCSNGSLQCRVCI (SEQ ID NO:3)

MKVKLLVLLCTFTATYADTICIGYHANNSTDTVDTVLEKNVTVTHSVNLL
EDSHNGKLCLLKGIAPLQLGNCSVAGWILGNPECELLISKESWSYIVEKP

Fig. 17A

NPENGTCYPGHFADYEELREQLSSVSSFERFEIFPKTSSWPNHDSNKGVT
AACPHAGAKSFYKNLIWLVKKGNSYPKLSKSYINDKGKEVLVLWGIHHPS
TSADQQSLYQNADAYVFVGTSRYSKKFKPEIAIRPKVRDQEGRMNYYWTL
VEPGDKITFEATGNLVVPRYAFAMERNAGSGIIISDTPVHDCNTTCQTPK
GAINTSLPFQNIHPITIGKCPKYVKSTKLRLATGLRNVPSIQSRGLFGAI
AGFIEGGWTGMVDGWYGYHHQNEQGSGYAADQKSTQNAINGITNKVNSVI
EKMNTQFTAVGKEFNKLERRMENLNKKVDDGFLDIWTYNAELLVLLENER
TLDFHDSNVKNLYEKVKSQLKNNAKEIGNGCFEFYHKCNDECMESVKNGT
YDYPKYSEESKLNREKIDGVKLESMGVYQILAIYSTVASSLVLLVSLGAI
SFWMCSNGSLQCRVCI (SEQ ID NO:4)

MKAILVVLLYTFATANADTLCIGYHANNSTDTVDTILEKNVTVTHSVNLL
EDKHNGKLCKLRGVAPLHLGKCNIAGWILGNPECESLSTASSWSYIVETS
SSDNGTCYPGDFIDYEELREQLSSISSFERFEIFPKESSWPNHTVTGVSA
SCSHNGESSFYRNLLWLTGKNGLYPNLSKSYANNKEKEVLVLWGVHHPPN
IGDQRALYHTENAYVSVVSSHYSRKFTPEIAKRPKVRDQEGRINYYWTLL
EPGDTIIFEANGNLIAPRYAFALSRGFGSGIINSNAPMDKCDAKCQTPQG
AINSSLPFQNVHPVTIGECPKYVRSAKLRMVTGLRNIPSIQSRGLFGAIA
GFIEGGWTGMIDGWYGYHHQNEQGSGYAADLKSTQNAIDEITNKVNSVIE
KMNTQFTAVGKEFNHLEKRIENLNKKVDDGFLDVWTYNAELLVLLENERT
LDYHDSNVKNLYEKVRSQLKNNAKEIGNGCFEFYHKCDNTCMESVKNGTY
DYPKYSEEAKLNREEIDGVKLESTRIYQILAIYSTVASSLVLVVSLGAIS
FWMCSNGSLQCRICIKN (SEQ ID NO:5)

H3 subtype.

MKTIIALSYILCLVFAQKLPGNDNSTATLCLGHHAVPNGTIVKTITNDQI
EVTNATELVQSSSTGEICDSPHQILDGENCTLIDALLGDPQCDGFQNKKW
DLFVERSKAYSNCYPYDVPDYASLRSLVASSGTLEFNNESFNWTGVTQNG
TSSACIRRSNNSFFSRLNWLTHLKFKYPALNVTMPNNEKFDKLYIWGVHH

Fig. 17B

PGTDNDQIFLYAQASGRITVSTKRSQQTVIPNIGSRPRVRNIPSRISIYW

TIVKPGDILLINSTGNLIAPRGYFKIRSGKSSIMRSDAPIGKCNSECITP

NGSIPNDKPFQNVNRITYGACPRYVKQNTLKLATGMRNVPEKQTRGIFGA

IAGFIENGWEGMVDGWYGFRHQNSEGTGQAADLKSTQAAIDQINGKLNRL

IGKTNEKFHQIEKEFSEVEGRIQDLEKYVEDTKIDLWSYNAELLVALENQ

HTIDLTDSEMNKLFERTKKQLRENAEDMGNGCFKIYHKCDNACIGSIRNG

TYDHDVYRDEALNNRFQIKGVELKSGYKDWILWISFAISCFLLCVVLLGF

IMWACQKGNIRCNICI (SEQ ID NO:7)

H2 subtype.

MAIIYLILLFTAVRGDQICIGYHANNSTEKVDTILERNVTVTHAKDILEK

THNGKLCKLNGIPPLELGDCSIAGWLLGNPECDRLLSVPEWSYIMEKENP

RNGLCYPGSFNDYEELKHLLSSVTHFEKVKILPKDRWTQHTTTGGSRACA

VSGNPSFFRNMVWLTKKGSNYPVAKGSYNNTSGEQMLIIWGVHHPNDETE

QRTLYQNVGTYVSVGTSTLNKRSIPEIATRPKVNGQGGRMEFSWTLLETW

DVINFESTGNLIAPEYGFKISKRGSSGIMKTEGTLENCETKCQTPLGAIN

TTLPFHNIHPLTIGECPKYVKSDRLVLATGLRNVPQIESRGLFGAIAGFI

EGGWQGMVDGWYGYHHSNDQGSGYAADKESTQKAIDGITNKVNSVIEKMN

TQFEAVGKEFNNLERRLENLNKKMEDGFLDVWTYNAELLVLMENERTLDF

HDSNVKNLYDKVRMQLRDNAKEIGNGCFEFYHKCDDECMNSVKNGTYDYP

KYEEESKLNRNEIKGVKLSNMGVYQILAIYATVAGSLSLAIMIAGISFWM

CSNGSLQCRICI (SEQ ID NO:6)

H7 subtype.

MNIQILAFIACVLTGAKGDKICLGHHAVANGTKVNTLTERGIEVVNATET

VETANIKKICTQGKRPTDLGQCGLLGTLIGPPQCDQFLEFSSDLIIERRE

GTDVCYPGKFTNEESLRQILRRSGGIGKESMGFTYSGIRTNGATSACRRS

GSSFYAEMKWLLSNSDNAAFPQMTKSYRNPRNKPALIIWGVHHSESVSEQ

Fig. 17C

TKLYGSGNKLITVGSSKYQQSFTPSPGARPQVNGQSGRIDFHWLLLDPND
TVTFTFNGAFIAPDRASFFRGESLGVQSDVPLDSGCEGDCFHSGGTIVSS
LPFQNINPRTVGKCPRYVKQKSLLLATGMRNVPENPKTRGLFGAIAGFIE
NGWEGLIDGWYGFRHQNAQGEGTAADYKSTQSAIDQITGKLNRLIEKTNQ
QFELIDNEFNEIEQQIGNVINWTRDSMTEVWSYNAELLVAMENQHTIDLA
DSEMNKLYERVRKQLRENAEEDGTGCFEIFHKCDDQCMESIRNNTYDHTQ
YRTESLQNRIQIDPVKLSSGYKDIILWFSFGASCFLLLAIAMGLVFICIK
NGNMRCTICI (SEQ ID NO:8)

H9 subtype.

MEVVSLITILLVVTVSNADKICIGYQSTNSTETVDTLTENNVPVTHAKEL
LHTEHNGMLCATNLGHPLILDTCTIEGLIYGNPSCDLLLGGREWSYIVER
PSAVNGLCYPGNVENLEELRSLFSSASSYQRIQIFPDTIWNVSYSGTSKA
CSDSFYRSMRWLTQKNNAYPIQDAQYTNNQEKNILFMWGINHPPTDTAQT
NLYTRTDTTTSVATEEINRTFKPLIGPRPLVNGLQGRIDYYWSVLKPGQT
LRVRSNGNLIAPWYGHILSGESHGRILKTDLNSGNCVVQCQTEKGGLNTT
LPFHNVSKYAFGNCPKYVGVKSLKLAVGLRNVPARSSRGLFGAIAGFIEG
GWSGLVAGWYGFQHSNDQGVGMAADRDSTQKAIDKITSKVNNIVDKMNKQ
YEIIDHEFSEVETRLNMINNKIDDQIQDIWAYNAELLVLLENQKTLDEHD
ANVNNLYNKVKRALGSNAVEDGKGCFELYHKCDDQCMETIRNGTYNRRKY
KEESRLERQKIEGVKLESEGTYKILTIYSTVASSLVIAMGFAAFLFWAMS
NGSCRCNICI (SEQ ID NO:9)

H10 subtype.

MYKIVLVLALLGAVHGLDKICLGHHAVSNGTIVKTLTNEKEEVTNATETV
ESKSLDKLCMKSRNYKDLGNCHPIGMVIGTPACDLHLTGTWDTLIERDNS
IAYCYPGATVNEEALRQKIMESGGIDKISTGFTYGSSINSAGTTKACMRN
GGNSFYAELKWLVSKSKGQNFPQTTNTYRNTDSAEHLIIWGIHHPSSTQE
KNDLYGTQSLSISVGSSTYQNNFVPVVGARPQVNGQSGRIDFHWTMVQPG
DNITFSHNGGLIAPSRVSKLKGRGLGIQSGASVDNDCESKCFWKGGSINT

Fig. 17D

KLPFQNLSPRTVGQCPKYVNKKSLLLATGMRNVPEVVQGRGLFGAIAGFI
ENGWEGMVDGWYGFRHQNAQGTGQAADYKSTQAAIDQITGKLNRLIEKTN
TEFESIESEFSEIEHQIGNVINWTKDSITDIWTYQAELLVAMENQHTIDM
ADSEMLNLYERVRKQLRQNAEEDGKGCFEIYHKCDDNCMESIRNNTYDHT
QYREEALLNRLNINPVKLSSGYKDVILWFSFGASCFVLLAVIMGLVFFCL
KNGNMRCTICI (SEQ ID NO:10)

Influenza B.

MKAIIVLLMVVTSNADRICTGITSSNSPHVVKTATQGEVNVTGVIPLTTT
PTKSHFANLKGTETRGKLCPKCLNCTDLDVALGRPMCVGTTPSAKASILH
EVRPVTSGCFPIMHDRTKIRQLPNLLRGYEHIRLSTHNVINAENAPGGPY
KIGTSGSCPNVTNGNGFFATMAWAVPKNDKNKTATNPLTIEVPYICTEGE
DQITVWGFHSDNETQMAKLYGDSKPQKFTSSANGVTTHYVSQIGGFPNQT
EDGGLPQSGRIVVDYMVQKSGKTGTITYQRGILLPQKVWCASGRSKVIKG
SLPLIGEADCLHEKYGGLNKSKPYYTGEHAKAIGNCPIWVKTPLKLANGT
KYRPPAKLLKERGFFGAIAGFLEGGWEGMIAGWHGYTSHGAHGVAVAADL
KSTQEAINKITKNLNSLSELEVKNLQRLSGAMDELHNEILELDEKVDDLR
ADTISSQIELAVLLSNEGIINSEDEHLLALERKLKKMLGPSAVEIGNGCF
ETKHKCNQTCLDRIAAGTFNAGEFSLPTFDSLNITAASLNDDGLDNHTIL
LYYSTAASSLAVTLMIAIFVVYMVSRDNVSCSICL (SEQ ID NO:11)

*Fig. 17E*

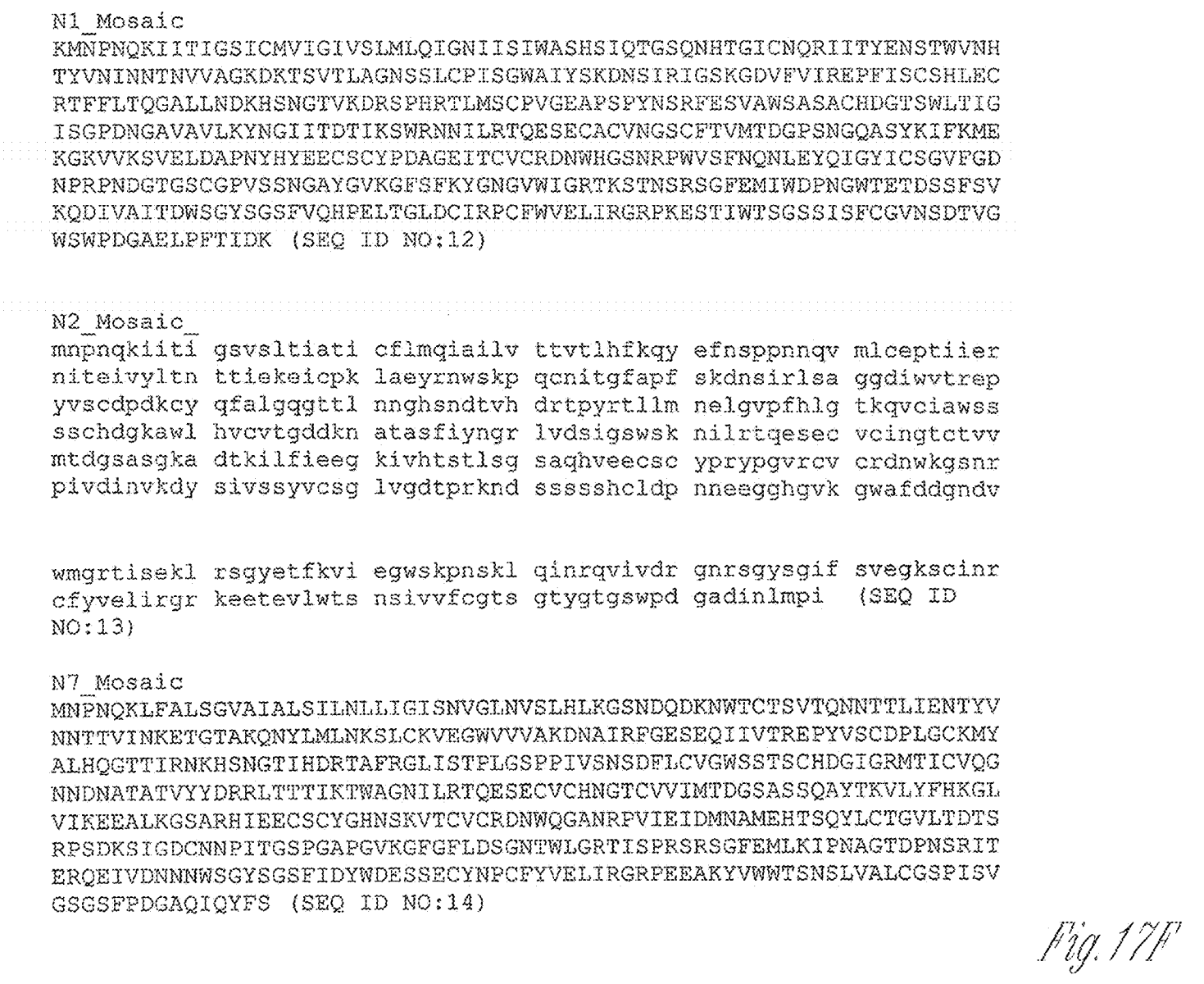

N1_Mosaic
KMNPNQKIITIGSICMVIGIVSLMLQIGNIISIWASHSIQTGSQNHTGICNQRIITYENSTWVNH
TYVNINNTNVVAGKDKTSVTLAGNSSLCPISGWAIYSKDNSIRIGSKGDVFVIREPFISCSHLEC
RTFFLTQGALLNDKHSNGTVKDRSPHRTLMSCPVGEAPSPYNSRFESVAWSASACHDGTSWLTIG
ISGPDNGAVAVLKYNGIITDTIKSWRNNILRTQESECACVNGSCFTVMTDGPSNGQASYKIFKME
KGKVVKSVELDAPNYHYEECSCYPDAGEITCVCRDNWHGSNRPWVSFNQNLEYQIGYICSGVFGD
NPRPNDGTGSCGPVSSNGAYGVKGFSFKYGNGVWIGRTKSTNSRSGFEMIWDPNGWTETDSSFSV
KQDIVAITDWSGYSGSFVQHPELTGLDCIRPCFWVELIRGRPKESTIWTSGSSISFCGVNSDTVG
WSWPDGAELPFTIDK (SEQ ID NO:12)

N2_Mosaic_
mnpnqkiiti gsvsltiati cflmqiailv ttvtlhfkqy efnsppnnqv mlceptiier
niteivyltn ttiekeicpk laeyrnwskp qcnitgfapf skdnsirlsa ggdiwvtrep
yvscdpdkcy qfalgqgttl nnghsndtvh drtpyrtllm nelgvpfhlg tkqvciawss
sschdgkawl hvcvtgddkn atasfiyngr lvdsigswsk nilrtqesec vcingtctvv
mtdgsasgka dtkilfieeg kivhtstlsg saqhveecsc yprypgvrcv crdnwkgsnr
pivdinvkdy sivssyvcsg lvgdtprknd sssshcldp nneegghgvk gwafddgndv wmgrtisekl rsgyetfkvi egwskpnskl qinrqvivdr gnrsgysgif svegkscinr
cfyvelirgr keetevlwts nsivvfcgts gtygtgswpd gadinlmpi (SEQ ID
NO:13)

N7_Mosaic
MNPNQKLFALSGVAIALSILNLLIGISNVGLNVSLHLKGSNDQDKNWTCTSVTQNNTTLIENTYV
NNTTVINKETGTAKQNYLMLNKSLCKVEGWVVVAKDNAIRFGESEQIIVTREPYVSCDPLGCKMY
ALHQGTTIRNKHSNGTIHDRTAFRGLISTPLGSPPIVSNSDFLCVGWSSTSCHDGIGRMTICVQG
NNDNATATVYYDRRLTTTIKTWAGNILRTQESECVCHNGTCVVIMTDGSASSQAYTKVLYFHKGL
VIKEEALKGSARHIEECSCYGHNSKVTCVCRDNWQGANRPVIEIDMNAMEHTSQYLCTGVLTDTS
RPSDKSIGDCNNPITGSPGAPGVKGFGFLDSGNTWLGRTISPRSRSGFEMLKIPNAGTDPNSRIT
ERQEIVDNNNWSGYSGSFIDYWDESSECYNPCFYVELIRGRPEEAKYVWWTSNSLVALCGSPISV
GSGSFPDGAQIQYFS (SEQ ID NO:14)

Fig. 17F

Codon usage table for Chicken

| 1st \ 2nd | T | | C | | A | | G | |
|---|---|---|---|---|---|---|---|---|
| T | TTT 0.41 | Phe | TCT 0.18 | Ser | TAT 0.37 | Tyr | TGT 0.36 | Cys |
| | TTC 0.59 | | TCC 0.22 | | TAC 0.63 | | TGC 0.64 | |
| | TTA 0.05 | Leu | TCA 0.15 | | TAA 0.26 | TERM | TGA 0.61 | TERM |
| | TTG 0.13 | | TCG 0.07 | | TAG 0.13 | | TGG 1.00 | Trp |
| C | CTT 0.13 | Leu | CCT 0.27 | Pro | CAT 0.40 | His | CGT 0.13 | Arg |
| | CTC 0.18 | | CCC 0.32 | | CAC 0.60 | | CGC 0.20 | |
| | CTA 0.07 | | CCA 0.29 | | CAA 0.29 | Gln | CGA 0.09 | |
| | CTG 0.43 | | CCG 0.12 | | CAG 0.71 | | CGG 0.15 | |
| A | ATT 0.34 | Ile | ACT 0.24 | Thr | AAT 0.41 | Asn | AGT 0.12 | Ser |
| | ATC 0.51 | | ACC 0.34 | | AAC 0.59 | | AGC 0.27 | |
| | ATA 0.15 | | ACA 0.29 | | AAA 0.38 | Lys | AGA 0.22 | Arg |
| | ATG 1.00 | Met | ACG 0.13 | | AAG 0.62 | | AGG 0.21 | |
| G | GTT 0.20 | Val | GCT 0.32 | Ala | GAT 0.48 | Asp | GGT 0.21 | Gly |
| | GTC 0.24 | | GCC 0.33 | | GAC 0.52 | | GGC 0.31 | |
| | GTA 0.12 | | GCA 0.25 | | GAA 0.40 | Glu | GGA 0.27 | |
| | GTG 0.45 | | GCG 0.10 | | GAG 0.60 | | GGG 0.22 | |

*Fig. 19A*

Codon usage table for Human

| 1st \ 2nd | T | | C | | A | | G | |
|---|---|---|---|---|---|---|---|---|
| T | TTT 0.43 | Phe | TCT 0.18 | Ser | TAT 0.42 | Tyr | TGT 0.42 | Cys |
| | TTC 0.57 | | TCC 0.23 | | TAC 0.58 | | TGC 0.58 | |
| | TTA 0.06 | Leu | TCA 0.15 | | TAA 0.22 | TERM | TGA 0.61 | TERM |
| | TTG 0.12 | | TCG 0.06 | | TAG 0.17 | | TGG 1.00 | Trp |
| C | CTT 0.12 | Leu | CCT 0.28 | Pro | CAT 0.41 | His | CGT 0.09 | Arg |
| | CTC 0.20 | | CCC 0.33 | | CAC 0.59 | | CGC 0.19 | |
| | CTA 0.07 | | CCA 0.27 | | CAA 0.27 | Gln | CGA 0.10 | |
| | CTG 0.43 | | CCG 0.11 | | CAG 0.73 | | CGG 0.19 | |
| A | ATT 0.35 | Ile | ACT 0.23 | Thr | AAT 0.44 | Asn | AGT 0.14 | Ser |
| | ATC 0.52 | | ACC 0.38 | | AAC 0.56 | | AGC 0.25 | |
| | ATA 0.14 | | ACA 0.27 | | AAA 0.40 | Lys | AGA 0.21 | Arg |
| | ATG 1.00 | Met | ACG 0.12 | | AAG 0.60 | | AGG 0.22 | |
| G | GTT 0.17 | Val | GCT 0.28 | Ala | GAT 0.44 | Asp | GGT 0.18 | Gly |
| | GTC 0.25 | | GCC 0.40 | | GAC 0.56 | | GGC 0.33 | |
| | GTA 0.10 | | GCA 0.22 | | GAA 0.41 | Glu | GGA 0.26 | |
| | GTG 0.48 | | GCG 0.10 | | GAG 0.59 | | GGG 0.23 | |

*Fig. 19B*

Codon usage table for pig

| | T | | C | | A | | G | |
|---|---|---|---|---|---|---|---|---|
| T | TTT 0.38 | Phe | TCT 0.15 | Ser | TAT 0.35 | Tyr | TGT 0.39 | Cys |
| | TTC 0.62 | | TCC 0.26 | | TAC 0.65 | | TGC 0.61 | |
| | TTA 0.06 | Leu | TCA 0.15 | | TAA 0.13 | TERM | TGA 0.79 | TERM |
| | TTG 0.1 | | TCG 0.06 | | TAG 0.08 | | TGG 1 | Trp |
| C | CTT 0.1 | Leu | CCT 0.24 | Pro | CAT 0.34 | His | CGT 0.07 | Arg |
| | CTC 0.21 | | CCC 0.35 | | CAC 0.66 | | CGC 0.22 | |
| | CTA 0.13 | | CCA 0.27 | | CAA 0.25 | Gln | CGA 0.12 | |
| | CTG 0.4 | | CCG 0.13 | | CAG 0.75 | | CGG 0.2 | |
| A | ATT 0.3 | Ile | ACT 0.19 | Thr | AAT 0.37 | Asn | AGT 0.12 | Ser |
| | ATC 0.53 | | ACC 0.41 | | AAC 0.63 | | AGC 0.26 | |
| | ATA 0.18 | | ACA 0.26 | | AAA 0.4 | Lys | AGA 0.19 | Arg |
| | ATG 1 | Met | ACG 0.13 | | AAG 0.6 | | AGG 0.2 | |
| G | GTT 0.14 | Val | GCT 0.24 | Ala | GAT 0.38 | Asp | GGT 0.14 | Gly |
| | GTC 0.27 | | GCC 0.45 | | GAC 0.62 | | GGC 0.36 | |
| | GTA 0.12 | | GCA 0.2 | | GAA 0.38 | Glu | GGA 0.26 | |
| | GTG 0.48 | | GCG 0.11 | | GAG 0.62 | | GGG 0.24 | |

TERM= Termination

Fig. 19C

BROADLY REACTIVE MOSAIC PEPTIDE FOR INFLUENZA VACCINE

CROSS-REFERENCE TO RELATED APPLICATIONS

This application is a continuation of U.S. application Ser. No. 14/207,123, filed on Mar. 12, 2014, which claims the benefit of the filing date of U.S. application Ser. No. 61/785,071, field on Mar. 14, 2013, the disclosure of which is incorporated by reference herein.

STATEMENT OF GOVERNMENT RIGHTS

This invention was made with government support under 2008-55620-19132 awarded by the USDA/NIFA. The government has certain rights in the invention.

BACKGROUND

Influenza viruses are a significant health concern for animals and humans. The World Health Organization (WHO) estimates that every year influenza virus infects up to 1 billion people, with 3-5 million cases of severe disease and 300,000-500,000 deaths annually (Meltzer et al., 1999). The traditional approach to controlling influenza A virus is based on diagnosis, treatment and prevention through vaccination. Each of these approaches, however, has flaws (e.g., antiviral resistance, incomplete protection, and improper vaccine distribution), e.g., treating every case with antiviral drugs is not a viable option because it is often ineffective and leads to viral resistance.

Highly pathogenic avian influenza (HPAI) H5N1 viruses have spread as far as Eurasia and Africa since their first emergence in 1996. These viruses infect a range of domestic and wild avian species as well as mammals (Pollack et al., 1998; Lazzari and Stohr, 2004), and pose a pandemic threat (Allen, 2006; Anonymous, 2005; Conly and Johmston, 2004). Current prevention and treatment strategies for H5N1 virus are antiviral, vaccine-based, or involve non-pharmaceutical measures, such as patient isolation or hand sanitation (Alexander et al., 2007; Ferguson et al., 2005; Ferguson et al., 2006; Iwami et al., 2008; Lipsitch et al., 2007; Stilanakis et al., 1998). However, these approaches have flaws (Iwami et al., 2008; Lipsitch et al., 2007; Lipsitch et al., 2009; Gandon et al., 2001).

Generation of inactivated vaccines (INV) has been optimized for seasonal flu, but presents several challenges for H5N1 viruses, including: 1) continual evolution of the viruses makes predicting a vaccine strain difficult; 2) egg propagation of vaccine stock is hindered due to the high lethality of H5N1 viruses to eggs and the poultry that provide them; and 3) the six to nine month time-period required to produce INV may be too long to protect large populations during a pandemic. In addition, initial studies in mice, ferrets and phase 1 human clinical trials have demonstrated that INV and other split-virion vaccines may require higher doses of antigen than traditional INV, with more than one administration needed to provide protective immunity (Cox et al., 2004; Ehrlich et al., 2008; Wright, 2008). Live vaccines elicit both humoral and cellular immune responses. However, they are not recommended in infants, elderly, or immuno-compromised individuals because they can cause pathogenic reactions (Jefferson et al., 2005; Kunisaki and Janoff, 2009; Mostow et al., 1969; Peck, 1968). Moreover, live vaccines can revert to wild-type viruses, potentially leading to vaccine failure and disease outbreaks (Mostow et al., 1979).

Current vaccines need to be improved to overcome limited cross protection, short duration of immunity and/or lack of robust protection. For instance, a critical failure in preparation for influenza pandemics and seasonal epidemics is the absence of a universal vaccine. This is due in part to the extraordinary genetic and antigenic variation of the virus, a consequence of rapid evolution in the form of antigenic drift and shift. Indeed, influenza strains vary by 1-2% per year, and vaccines generally do not elicit protection from one year to the next, necessitating frequent vaccine updates. This diversity represents a significant challenge to the development of a broadly effective vaccine, as no single viral variant can induce immunity across observed field strains, and incorporating all circulating variants into one multivalent vaccine isn't feasible.

Multiple approaches have been studied to develop a universal influenza vaccine that could be applied to H5N1 viruses. One approach is to use conserved sequences such as the stalk region of HA or the internal NP or M1 proteins. Another approach involves consensus sequences that combine many H5N1 hemagglutinin sequences into a single gene. Of these approaches, only the consensus approach has shown partial protection against a diverse panel of H5N1 isolates. Nevertheless, a broadly effective strategy for H5N1, or other pandemic viruses, control remains elusive.

SUMMARY OF THE INVENTION

A mosaic influenza virus sequence is generated in silico from natural sequences with an emphasis on current strains and is optimized for maximum T cell epitope coverage (e.g., maintaining contiguous epitope sequences) rather than on consensus residues. A mosaic sequence having a linear string of primarily natural occurring influenza virus T cell epitopes, optionally including B cell epitopes and/or T cytotoxic lymphocyte (TCL) epitopes, would likely provide robust and broad protection against challenge. That is because an objective scoring mechanism is employed that optimizes for maximum T cell epitope coverage of the known diversity of wild-type influenza. Consequently, the synthetic protein that is generated is less subject to the inherent biases in the body of publically-available data. Moreover, the mosaic sequence is more likely to be functional and properly folded.

As described below, a modified vaccinia Ankara (MVA) vector was used to express a mosaic H5 HA gene (H5M). The MVA vector offers several advantages such as 1) safety, 2) stability, 3) rapid induction of humoral and cellular responses, and 4) multiple routes of inoculation. In mice, a single dose of MVA-H5M construct provided sterilizing immunity (no detectable virus in lung tissues post challenge) against H5N1 HPAI clades 0, 1 and 2 viruses. Furthermore, MVA-H5M provided full protection as early as 10 days post exposure and as long as 6 months post-vaccination. Both neutralizing antibodies and antigen-specific $CD4^+$ and $CD8^+$ T cells were detected at 5 months post-vaccination. In addition, MVA-H5M also provided cross subtype protection against H1N1 virus (PR8) challenged. These results indicate that the mosaic vaccine approach has great potential for broadening the efficacy of influenza vaccines, perhaps including protection against all influenza subtypes.

The invention thus provides a universal influenza vaccine with a mosaic (synthetic) antigen. In one embodiment, the invention provides an isolated polynucleotide comprising a nucleic acid segment for an influenza virus HA having SEQ ID NO:1 or a polypeptide having at least 95%, e.g., at least 99%, amino acid sequence identity thereto, an influenza virus HA having SEQ ID NO:2 or a polypeptide having at least 95%, e.g., at least 99%, amino acid sequence identity thereto, an influenza virus HA having SEQ ID NO:3 or a polypeptide having at least 95%, e.g., at least 99%, amino acid sequence identity thereto, an influenza virus HA having SEQ ID NO:4 or a polypeptide having at least 95%, e.g., at least 99%, amino acid sequence identity thereto, an influenza virus HA having SEQ ID NO:5 or a polypeptide having at least 95%, e.g., at least 99%, amino acid sequence identity thereto, an influenza virus HA having SEQ ID NO:6 or a polypeptide having at least 95%, e.g., at least 99%, amino acid sequence identity thereto, an influenza virus HA having SEQ ID NO:7 or a polypeptide having at least 95%, e.g., at least 99%, amino acid sequence identity thereto, an influenza virus HA having SEQ ID NO:8 or a polypeptide having at least 95%, e.g., at least 99%, amino acid sequence identity thereto, an influenza virus HA having SEQ ID NO:9 or a polypeptide having at least 95%, e.g., at least 99%, amino acid sequence identity thereto, an influenza virus HA having SEQ ID NO:10 or a polypeptide having at least 95%, e.g., at least 99%, amino acid sequence identity thereto, an influenza virus HA having SEQ ID NO:11 or a polypeptide having at least 95%, e.g., at least 99%, amino acid sequence identity thereto, an influenza virus NA having SEQ ID NO:12 or a polypeptide having at least 95%, e.g., at least 99%, amino acid sequence identity thereto, an influenza virus NA having SEQ ID NO:13 or a polypeptide having at least 95%, e.g., at least 99%, amino acid sequence identity thereto, or an influenza virus NA having SEQ ID NO:14 or a polypeptide having at least 95%, e.g., at least 99%, amino acid sequence identity thereto, or the complement of the nucleic acid segment, which polypeptide is immunogenic, e.g., providing subtype protection against two or more distinct viruses, e.g., from different clades (cross clade is two or more clades). Sequences included are those with one or a few amino acid insertions, so long as the resulting sequences result in the immunogenicity, e.g., providing subtype protection against two or more distinct viruses, e.g., from different clades. In one embodiment, the nucleic acid segment is operably linked to a promoter and/or a transcription termination sequence.

To generate the synthetic antigens of the invention, which include epitopes representing a large number of primary influenza virus isolates, e.g., from circulating strains, influenza HA subtype and NA subtype sequences were compiled. For example, a sequence for a mosaic H5 antigen was generated in silico using over two thousand published influenza virus H5 sequences from the Influenza Research Database that represent (nonduplicated) sequences of primary isolates and/or circulating isolates. In one embodiment, the sequences represent circulating viruses from clades 1, 2.1.3, 2.2, 2.2.1, 2.3.2, 2.3.4 and/or 7, or from clades 0 1, 2.1.1, 2.1.2, 2.1.3, 2.2, 2.2.1, 2.3.1, 2.3.2, 2.3.3 2.3.4, 2.4, 2.6, 3, 4, 5, 6, 7, 8 and/or 9. The efficacy of one of the generated sequences (SEQ ID NO:1) was tested in a highly pathogenic avian influenza (HPAI) model in mice using a recombinant poxvirus (the attenuated MVA vector). The mosaic H5 (H5M) sequence was found to be quite effective and provided broad protection against viruses from different clades, including protection against Clade 0, Clade 1, and Clade 2 viruses. Thus, a mosaic influenza virus antigen may be employed as a vaccine that is administered as isolated protein, isolated nucleic acid or via a delivery vehicle, including a viral vector or virus like particle. The viral vector may be a heterologous viral vector, e.g., a vector from poxvirus, avipoxviruses such as fowlpox (FPV) or canarypox viruses, Newcastle Disease virus, adenovirus, alphaviruses, or other viruses, or an influenza virus such as a live attenuated influenza virus. The present invention thus relates to new influenza vaccine constructs, and methods of making and using those constructs.

In one embodiment, to generate a mosaic sequence, a genetic algorithm is employed to generate, select and recombine in silico potential T-cell epitopes and/or B-cell epitopes, into "mosaic" protein sequences that are antigenic and can provide greater coverage of global viral variants than any single wild-type protein. T-cell epitopes are generally from about 8 to about 15 amino acid residues in length, and B cell epitopes are generally from about 12 up to about 35 amino acid residues in length. The combination of epitopes in a full length mosaic HA or NA sequence may be employed in nucleic acid vectors for administration or for protein expression, or a fragment of the sequence which is immunogenic may also be employed. An "immunogenic portion" of a full length sequence may be as few as 8 amino acids in length and up to one or more residues shorter than a full length polypeptide, e.g., a full length HA-1. For instance, an immunogenic portion of a polypeptide is a polypeptide that is about 50%, 60%, 70%, 80%, 85%, 90%, 95% or 99% of the length of a corresponding full length polypeptide, such as a full length HA or HA-1, or NA, and elicits an immunogenic response that is at least 30%, 40%, 50%, or more, of the immunogenic response of the corresponding full-length polypeptide. As described herein, mosaic sequences may include characteristic residues at one or more positions, and in one embodiment, immunogenic portions of the mosaic sequences also have those characteristic residue(s).

The genetic algorithm based approach to mosaic sequence generation has been employed with other HA A subtypes, e.g., H1, H3, H7, H9, and H10, HA B, and other influenza virus proteins, e.g., NA subtypes N1, N2 and N7. Because the approach incorporates a plurality of influenza epitopes into a mosaic sequence, the resulting sequences are likely useful in a subtype specific universal influenza vaccine that can provide both domesticated animals and humans, and/or avians, the maximum possible protection against this devastating respiratory disease.

Thus, the invention provides a composition comprising a recombinant nucleic acid molecule having a nucleotide sequence, e.g., in a viral vector such as live recombinant poxvirus, that encodes a mosaic influenza virus antigen as described herein. In one embodiment, the viral vector genome comprises at least one expression cassette having a promoter operably linked to a heterologous open reading frame comprising the nucleotide sequence that elicits neutralizing antibodies and/or a cytotoxic T cell response. In one embodiment, the composition includes more than one nucleotide sequence, each encoding a different antigen, at least one of which is a mosaic antigen, e.g., a mosaic HA or NA polypeptide. For example, the composition may include more than one live recombinant poxvirus, e.g., different isolates having different antigens or one virus encoding more than one influenza virus antigen. Once the recombinant virus infects cells of a host animal, the antigen(s) is expressed in an amount effective to induce an immune response. In one embodiment, a live recombinant virus may be obtained from a culture of isolated mammalian cells transfected or transformed with a recombinant virus genome comprising the at least one expression cassette. Any cell, e.g., any avian or mammalian cell, such as a human, canine, bovine, equine, feline, swine, ovine, mink, or non-human primate cell, including mutant cells, which supports efficient replication of virus can be employed to isolate and/or propagate the viruses. In another embodiment, host cells are continuous mammalian or avian cell lines or cell strains. Viral vectors useful in the invention include but are not limited to recombinant adenovirus, retrovirus, lentivirus, herpesvirus, poxvirus, papilloma virus, or adeno-associated virus. Viral and non-viral vectors may be present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes.

The recombinant nucleic acid, viral vector or mosaic protein of the invention may be administered via any route including, but not limited to, intramuscular, subcutaneous, intranasal, buccal, rectal, intravenous or intracoronary administration, and transfer to host cells may be enhanced using electroporation and/or iontophoresis.

In one embodiment, a composition of the invention, such as a vaccine, e.g., for in ovo, mucosal, or parenteral administration, having a recombinant virus may include doses ranging from $1 \times 10^4$ to $1 \times 10^8$ plaque forming units (PFU) or $TCID_{50}$, e.g., from $1 \times 10^4$ to $1 \times 10^8$ PFU or $TCID_{50}$, which may be administered as a single dose or in two or more doses, or each dose may include from $1 \times 10^4$ to $1 \times 10^8$ PFU or $TCID_{50}$, e.g., from $1 \times 10^4$ to $1 \times 10^8$ PFU or $TCID_{50}$, of recombinant virus, such as poxvirus. For instance, each dose may have the same number of PFU or $TCID_{50}$, or the booster dose(s) may have higher or lower amounts relative to the initial (priming) dose. The priming dose and/or booster dose(s) may include an adjuvant. Additionally, the vector used for prime and boost may be different. For example, a pox virus expressing the mosaic antigen may be used for a primary dose, while another viral vector, DNA vector, RNA vector, or protein is used for the secondary dose, or vice versa.

In one embodiment, a composition of the invention encodes or comprises an influenza virus HA and/or NA, which may induce a humoral response, a cellular response, or both, and so likely provides cross-protection. In one embodiment, the vaccine confers from 50 to 100% protection against heterologous challenge (cross protection). In one embodiment, the administration of a composition of the invention to avians or mammals provides for enhanced survival, e.g., after exposure to influenza virus, including survival rates of at least 35% or greater, for instance, survival rates of 50%, 60%, 70%, 75%, 80%, 85%, 90% or greater, relative to survival rates in the absence of the administration of that composition or any other prophylactic or therapeutic agent. The compositions of the invention are useful prophylactically or therapeutically, e.g., against seasonal flu.

BRIEF DESCRIPTION OF THE FIGURES

FIGS. 17A-F. Other exemplary mosaic influenza antigen sequences H1M (SEQ ID NO:2), H1M (SEQ ID NO:3), H1M (SEQ ID NO:4), H1M (SEQ ID NO:5), H2M (SEQ ID NO:6), H3M (SEQ ID NO:7), H7M (SEQ ID NO:8), H9M (SEQ ID NO:9), H10M (SEQ ID NO:10), HBM (SEQ ID NO:11), N1 (SEQ ID NO:12), N2 (SEQ ID NO:13), and N7 (SEQ ID NO:14).

FIGS. 19A-C. Codon usage tables for exemplary organisms.

DETAILED DESCRIPTION

Definitions

Figure 1:
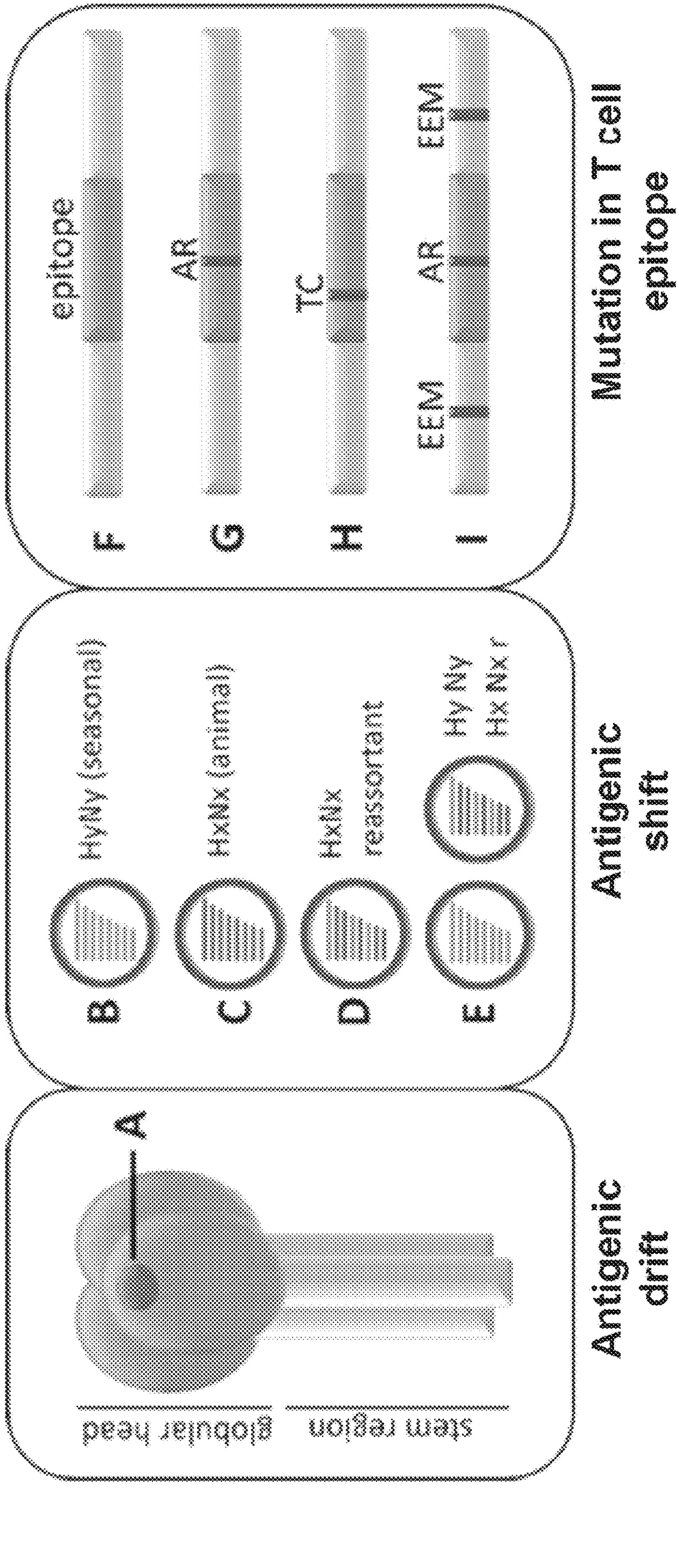
FIG. 1. Schematic mechanisms for immune response evasion by influenza virus. Left panel, antigenic drift; middle panel, antigenic shift; right panel mutation in T cell epitope. AR, TC, EEM are abbreviations for amino acids.

As used herein, the term “isolated” refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and is substantially free from other infectious agents.

A “recombinant” virus is one which has been manipulated in vitro, e.g., using recombinant DNA techniques, to introduce changes to the viral genome.

As used herein, the term “recombinant nucleic acid” or “recombinant DNA sequence or segment” refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA “derived” from a source, would be a DNA sequence that is identified as a useful fragment, and which is then chemically synthesized in essentially pure form. An example of such DNA “isolated” from a source would be a useful DNA sequence that is excised or removed from said source by chemical means, e.g., by the use of restriction endonucleases, so that it can be further manipulated, e.g., amplified, for use in the invention, by the methodology of genetic engineering.

Conserved or Consensus Influenza Virus Sequences Versus Mosaic Influenza Virus Sequences In an effort to develop vaccines that maximize the representation of antigenic features present in diverse vial populations, a series of strategies have been proposed. The approaches have included concatenating commonly recognized T-cell epitopes (Palker et al., 1989), creating psuedo-protein strings of T-cell epitopes (De Groot et al., 2005) and generating consensus overlapping peptide sets from proteins (Thomson et al., 2005). Evolutionary approaches such as the use of consensus sequences (Gao et al., 2004, 2005; Gaschen et al., 2002), and the most recent common ancestor (MRCA) of viral populations, have also been proposed with the assumption that these approaches capture viral diversity (Gaschen et al., 2002). Unfortunately, experimental studies in animal models using these strategies have documented underwhelming humoral immune responses (Doria-Rose et al., 2005; Gao et al., 2005).

Because of antigenic drift of influenza viruses, the components of an influenza virus vaccine are tailored annually to match the strains that would most likely be dominant in the population for the upcoming influenza season. Yearly vaccinations are required because each seasonal vaccine elicits neutralizing antibodies that are specific only for the vaccine strains and closely related isolates. In case of a new pandemic strain, it takes several months to reformulate the vaccine that matches to the new strain.

To overcome these problems and to stop the spread of influenza indefinitely, a single broadly protective vaccine or universal vaccine is needed. Thus, conserved influenza virus sequences from different strains, or consensus sequences, have been employed to provide an antigen with broad protective properties. For example, conserved influenza virus proteins include NP and M1, which are targets for cellular immunity. There is a certain immunogenic region of M1 (M58-66: GILGFVFTL) that is evolutionarily conserved (Thomas et al., 2006) and is 100% conserved in almost all the strains of influenza virus including H1N1, H5N1, H3N2 and pandemic H1N1, and the extracellular N-terminal domain of M2 protein (eM2), a 23 amino acid peptide, is highly conserved in all human influenza A strains. Universal neutralizing antibodies have been isolated against the conserved HA2 region of hemagglutinin (HA) (Ekiert et al., 2009; Steel et al., 2010). However, universal neutralizing antibodies are rare, have low affinity, and cannot be induced in large quantities during infection or vaccination.

Sequence alignments are relied on to yield a “consensus” sequence, where many genetic sequences are incorporated into a single sequence. A consensus sequence may thus minimize the genetic distance between vaccine strains and viruses and so may elicit more cross-reactive immune responses than an immunogen derived from any single influenza virus.

The consensus sequence approach is limited because the consensus sequence is dependent on the input sequences, which are usually heavily biased databases (e.g., temporal and spatial collection biases) based on how sequences are reported to a database, such as the National Center for Biotechnology Information (NCBI). The sequences that are most reported to NCBI are not necessarily representative of circulating strains. Consequently, the synthetic consensus sequence does not necessarily represent currently circulating diversity. Moreover, since a consensus sequence is 100% synthetic, it might not be functional or conformationally “correct”.

In contrast, the mosaic protein sequences disclosed herein were generated using an objective scoring mechanism that optimizes for maximum T cell epitope coverage of the known diversity of wild-type influenza. Consequently, the synthetic protein that is generated is less subject to the inherent biases in the data. The utility of the mosaic antigen approach, and its superiority to a consensus sequence approach, was demonstrated in vivo for a mosaic H5 HA antigen (H5M). The H5M vaccine can elicit protection against H5N1 HPAI clades 0, clade 1 and clade 2. Even recent consensus approaches that have tried to control for the most diversity of input sequence have failed to simultaneously elicit immune responses against all of these clades (see, e.g., Hessel et al., 2011).

Exemplary Compositions and Methods of the Invention

The present invention relates to compositions and methods which employ recombinant nucleic acid sequence or vectors, or isolated protein, e.g., HA or NA having at least 80%, 85%, 90%, 92%, 95%, 97%, 98%, or 99% amino acid sequence identity to one of SEQ ID NOs:1-14, e.g., a recombinant virus or recombinant cell which expresses one or more of the recombinant gene products, or extracts of those cells, or inactivated recombinant virus, e.g., inactivated via chemical or heat treatment, which expresses one or more of the protein(s). In one embodiment, the recombinant virus or isolated protein may be obtained from a recombinant bacterial cell, avian cell or mammalian cell.

The compositions and methods are useful for preventing, inhibiting or treating influenza virus infection in animals including avians and mammals. The compositions of the invention, for example, a single dose thereof, are broad spectrum immunotherapeutics and provide for prophylactic and/or therapeutic activity against a variety of influenza virus isolates. In one embodiment, the method includes administering a composition of the invention to a mammal having or suspected of having an influenza virus infection. In one embodiment, a composition comprises an effective amount of recombinant isolated protein e.g., a protein having at least 80%, 85%, 90%, 92%, 95%, 97%, 98%, or 99% amino acid sequence identity to one of SEQ ID NOs:1-14, or an immunogenic portion thereof, or a recombinant virus or cell, such as an attenuated or avirulent virus, which expresses one or more recombinant gene products one of which is a mosaic protein of the invention, or soluble extracts of those cells. In one embodiment, the composition or method employs a recombinant vector that express a protein having at least 80%, 85%, 90%, 92%, 95%, 97%, 98%, or 99% amino acid sequence identity to SEQ ID NO:1.

In one embodiment, the composition further comprises a pharmaceutically acceptable carrier. In one embodiment, the composition is administered orally, for instance, in a formulation suitable to deliver protein(s). In another embodiment, the composition is administered through various other acceptable delivery routes, for example, through parenteral injection, intranasally, or via an intra-muscular injection. In one embodiment, the composition is administered to the animal one or more times, at times including but not limited to 1 to 7 days, 1 to 3 weeks or about 1, 2, 3, 4 or more, e.g., up to 6, months, before the mammal or avian is exposed to influenza virus. In one embodiment, the composition is administered to the mammal or avian one or more times after exposure to the virus, e.g., at 1 hour, 6 hours, 12 hours, 1 day, 2 days, 4 days or more, e.g., up to about 2 weeks, after exposure.

In one embodiment, the invention provides a recombinant nucleic acid molecule having a nucleotide sequence encoding an immunogenic influenza virus HA polypeptide having one of SEQ ID NOs:1-11, a sequence with at least 99% amino acid sequence identity thereto, or a portion thereof, which provides cross-clade reactivity. In one embodiment, the invention provides a recombinant nucleic acid molecule having a nucleotide sequence encoding an immunogenic H5 HA polypeptide having SEQ ID NO:1, or a sequence with at least 95% amino acid sequence identity thereto or an immunogenic portion thereof, wherein the HA has Ile at position 87, Thr at position 172, Val at position 226 or Thr at position 279, or a combination thereof. Further provided is a recombinant nucleic acid molecule having a nucleotide sequence encoding an immunogenic H1 HA polypeptide having SEQ ID NO:2, 3, 4, or 5, a sequence with at least 95% amino acid sequence identity thereto or an immunogenic portion thereof, wherein the HA i) has Arg at position 206, Leu at position 432, or Val at position 434, or a combination hereof; ii) has Ile at position 125 and Val at position 564; or iii) has Lys at position 62, Ile at position 64, Gln at position 68, Asn at position 71, Ser at position 73, Val at position 74, Leu at position 86, Ile at position 88, Ser at position 89, Lys at position 90, Glu at position 91, Lys at position 99, Pro at position 100, Asn at position 101, Pro at position 102, Glu at position 103, His at position 111, or Ala at position 113, or a combination thereof. In addition, the invention provides a recombinant nucleic acid molecule having a nucleotide sequence encoding an immunogenic H2 HA polypeptide having SEQ ID NO:6, a sequence with at least 95% amino acid sequence identity thereto or an immunogenic portion thereof, wherein the HA has Ala at position 24, Lys at position 45, Ser at position 87, Thr at position 258, Asn at position 260, or Leu at position 261, or a combination thereof. The invention also provides a recombinant nucleic acid molecule having a nucleotide sequence encoding an immunogenic H7 HA polypeptide having SEQ ID NO:8, a sequence with at least 95% amino acid sequence identity thereto or an immunogenic portion thereof, wherein the HA has Ser at position 91, Ser at position 92, Arg at position 122, Gly at position 127, Glu at position 195, Val at position 197, or Ser at position 198, or a combination thereof, a recombinant nucleic acid molecule having a nucleotide sequence encoding an immunogenic H9 HA polypeptide having SEQ ID NO:9, a sequence with at least 95% amino acid sequence identity thereto or an immunogenic portion thereof, wherein the HA has Gln at position 180, Glu at position 215, or Tyr at position 240, or a combination thereof, a recombinant nucleic acid molecule having a nucleotide sequence encoding an influenza B HA polypeptide having SEQ ID NO:11, a sequence with at least 95% amino acid sequence identity thereto or an immunogenic portion thereof, wherein the HA has Met at position 86, Val at position 88, Thr at position 90, Thr at position 91, Lys at position 95, Ala at position 96, or Val at position 161, or a combination thereof, or a recombinant nucleic acid molecule having a nucleotide sequence encoding a H3 HA polypeptide having SEQ ID NO:7, and/or a recombinant nucleic acid molecule having a nucleotide sequence encoding a H10 HA polypeptide having having SEQ ID NO:10.

In one embodiment, the invention provides a recombinant nucleic acid molecule having a nucleotide sequence encoding an immunogenic influenza virus NA polypeptide having one of SEQ ID NOs:12-14, a sequence with at least 95% amino acid sequence identity to SEQ ID NO:12 having Ala at position 35, Ser at position 42, Asn at position 44, His at position 45, Thr at position 46, Gly at position 47, Ile at position 48, Arg at position 52, Ser at position 59, His at position 64, Asn at position 70, Val at position 74, Val at position 75, Ala at position 76, Gly at position 77, Asp at position 79, Lys at position 80, Thr at position 81, Ile at position 99, or Ser at position 105, or a combination thereof; a sequence with at least 99% amino acid sequence identity to SEQ ID NO:13 having Lys at position 199, Asn at position 221, or Gln at position 433, or a combination thereof; or a sequence with at least 99% amino acid sequence identity to SEQ ID NO:14 having Ile at position 353; or an immunogenic portion thereof.

The recombinant nucleic acid molecule may be in the form of an expression vector, such as a recombinant virus, linked to the nucleotide sequence of the invention, e.g., forming a promoter operable in avian or mammalian cells, A recombinant poxvirus may include a nucleotide sequence encoding an immunogenic polypeptide having one of SEQ ID NOs. 1-14, a sequence with at least 95% amino acid sequence identity thereto or a portion thereof that provides cross-clade reactivity.

The invention provides an isolated immunogenic influenza virus HA polypeptide having one of SEQ ID NOs:1-11, a sequence with at least 95% amino acid sequence identity thereto or a portion thereof, which provides cross-clade reactivity, e.g., the HA polypeptide has at least or has greater than 99% amino acid sequence identity to one of SEQ ID NOs:1-11. In one embodiment, the polypeptide having SEQ ID NO:1, the sequence with at least 95% amino acid sequence identity thereto or the portion thereof, has Ile at position 87, Thr at position 172, Val at position 226 or Thr at position 279, or a combination thereof. In one embodiment, the polypeptide having SEQ ID NO:2, 3, 4, or 5, the sequence with at least 95% amino acid sequence identity thereto or the portion thereof, i) has Arg at position 206, Leu at position 432, or Val at position 434, or a combination hereof; ii) has Ile at position 125 and Val at position 564: or iii) has Lys at position 62, Ile at position 64, Gln at position 68, Asn at position 71, Ser at position 73, Val at position 74, Leu at position 86, Ile at position 88, Ser at position 89, Lys at position 90, Glu at position 91, Lys at position 99, Pro at position 100, Asn at position 101, Pro at position 102, Glu at position 103, His at position 111, or Ala at position 113, or a combination thereof. In one embodiment, the polypeptide having SEQ ID NO:6, a sequence with at least 95% amino acid sequence identity thereto or an immunogenic portion thereof has Ala at position 24, Lys at position 45, Ser at position 86, Thr at position 258, Asn at position 260, or Leu at position 261, or a combination thereof. In one embodiment, the polypeptide having SEQ ID NO:8, the sequence with at least 95% amino acid sequence identity thereto or the portion thereof, has Ser at position 91, Ser at position 92, Arg at position 122, Gly at position 127, Glu at position 195, Val at position 197, or Ser at position 198, or a combination thereof. In another embodiment, the polypeptide having SEQ ID NO:9, the sequence with at least 95% amino acid sequence identity thereto or the portion thereof has Gln at position 180, Glu at position 215, or Tyr at position 240, or a combination thereof. In yet another embodiment, the polypeptide having SEQ ID NO:11, the sequence with at least 95% amino acid sequence identity thereto or the portion thereof has Met at position 86, Val at position 88, Thr at position 90, Thr at position 91, Lys at position 95, Ala at position 96, or Val at position 161, or a combination thereof. The invention also provides an isolated immunogenic influenza virus NA polypeptide having one of SEQ ID NOs:12-14, a sequence with at least 95% amino acid sequence identity to SEQ ID NO: 12 or at least 99% amino acid sequence identity to one of SEQ ID NOs. 13-14, thereto or an immunogenic portion thereof. For example, the sequence with at least 95% amino acid sequence identity to SEQ ID NO:12 has Ala at position 35, Ser at position 42, Asn at position 44, His at position 45, Thr at position 46, Gly at position 47, Ile at position 48, Arg at position 52, Ser at position 59, His a position 64, Asn at position 70, Val at position 74, Val at position 75, Ala at position 76, Gly at position 77, Asp at position 79, Lys at position 80, Thr at position 81, Ile at position 99, or Ser at position 105, or a combination thereof; the sequence with at least 99% amino acid sequences identity to SEQ ID NO:13 has Lys at position 199, Asn at position 221, or Gln at position 433, or a combination thereof; or the sequence with at least 99% amino acid sequence identity to SEQ ID NO:14 has Ile at position 353; or an immunogenic portion thereof.

The recombinant nucleic acid, e.g., a recombinant virus or recombinant polypeptide may be employed as vaccine. In one embodiment, the invention provides a vaccine comprising a recombinant virus, the genome of which comprises at least one expression cassette having a promoter operably linked to a heterologous open reading frame comprising a nucleotide sequence for an influenza virus polypeptide having one of SEQ ID NOs: 1-14, a polypeptide with at least 95% amino acid sequence thereto or an immunogenic portion thereof, or a combination thereof, which provides cross-clade reactivity. In one embodiment, the vaccine further comprises an adjuvant. In one embodiment, the vaccine further comprises a different virus. In one embodiment, the vaccine further comprises a pharmaceutically acceptable carrier, e.g., wherein the carrier is suitable for intranasal or intramuscular administration. In one embodiment, the vaccine is in freeze-dried form. In one embodiment, the vaccine is adapted for mucosal, intramuscular or intradermal delivery.

Also provided is a method to prevent, inhibit or treat influenza virus infection comprising administering to an avian or a mammal an effective amount of a composition comprising the recombinant nucleic acid molecule, the recombinant virus, or the recombinant polypeptide of the invention. Also provided is a recombinant method to immunize an animal against influenza infection, comprising: administering to an animal or an egg thereof, a composition comprising an amount of at least one recombinant virus comprising a recombinant nucleic acid molecule of the invention effective to induce an adaptive immune response to influenza virus. In one embodiment, the animal is an avian or a mammal. In one embodiment, the composition is intradermally administered. In one embodiment, the composition is intramuscularly, or mucosally, administered. In one embodiment, the effective amount is administered in more than one dose. In one embodiment, the composition further comprises an adjuvant. In one embodiment, the composition is parenterally administered. In one embodiment, the composition is administered intranasally or is administered orally.

In one embodiment, the invention provides a method to prevent influenza virus infection of an animal. The method includes administering to a mammal an effective amount of a live recombinant virus, the genome of which comprises at least one expression cassette having a promoter operably linked to a heterologous open reading frame comprising a nucleotide sequence for a mosaic antigen of an influenza virus protein that elicits neutralizing antibodies and/or a cellular immune response. In one embodiment, the method includes administering to the mucosa of an animal, e.g., orally administering, an effective amount of one or more live recombinant poxviruses, the genome of at least one of which comprises at least one expression cassette having a promoter operably linked to a heterologous open reading frame comprising a nucleotide sequence for a mosaic antigen that elicits neutralizing antibodies and/or a cellular immune response. For example, the effective amount may be from $1\times10^4$ to $1\times10^8$ PFU or $TCID_{50}$, e.g., from $1\times10^6$ to $1\times10^7$ PFU or $TCID_{50}$, which may be administered as a single dose or in two or more doses, or each dose may include from $1\times10^4$ to $1\times10^8$ PFU or $TCID_{50}$, e.g., from $1\times10^6$ to $1\times10^7$ PFU or $TCID_{50}$. For instance, each dose may have the same number of PFU, or the booster dose(s) may have higher or lower amounts relative to the initial dose. The initial booster may be administered from 2 to 8 weeks after the priming dose, for instance 3 to 4 weeks after the priming dose. The priming dose and/or booster dose(s) may include an adjuvant. In one embodiment, mucosal delivery of the recombinant virus and adjuvant is employed.

Also provided is a method to immunize an avian or an egg thereof against influenza virus. The method includes administering to the avian or an egg thereof an effective amount of isolated mosaic influenza virus protein or a live recombinant virus, the genome of which comprises at least one expression cassette having a promoter operably linked to a heterologous open reading frame comprising a nucleotide sequence for a mosaic influenza virus protein that elicits neutralizing antibodies and/or a cellular immune response. The immunized avian may be one of a population of avians, e.g., a flock of chickens, where at least one of the population has symptoms of infection or anti-influenza virus antibodies. In one embodiment, the antigen is a mosaic HA polypeptide.

In one embodiment, the method includes administering to the mucosa of an avian or mammal, e.g., orally or nasally administering, an effective amount of one or more recombinant viruses, the genome of at least one of which comprises at least one expression cassette having a promoter operably linked to a heterologous open reading frame comprising a nucleotide sequence for a mosaic influenza virus antigen that elicits neutralizing antibodies and/or a cellular immune response. For example, the effective amount may be from $1\times10^4$ to $1\times10^8$ PFU or $TCID_{50}$, e.g., from $1\times10^6$ to $1\times10^7$ PFU or $TCID_{50}$, which may be administered as a single dose or in two or more doses, or each dose may include from $1\times10^4$ to $1\times10^8$ PFU or $TCID_{50}$, e.g., from $1\times10^6$ to $1\times10^7$ PFU or $TCID_{50}$. For instance, each dose may have the same number of PFU, or the booster dose(s) may have higher or lower amounts relative to the initial dose. The initial booster may be administered from 2 to 8 weeks after the priming dose, for instance 3 to 4 weeks after the priming dose. The priming dose and/or booster dose(s) may include an adjuvant. In one embodiment, mucosal delivery of the recombinant virus and adjuvant is employed, e.g., a recombinant virus encoding influenza HA and an adjuvant, which adjuvant may be delivered via a recombinant virus.

In one embodiment, the invention provides a mosaic H5 polypeptide sequence with characteristic residues at positions 87, 172, 226 or 279, or a combination thereof, of HA (numbering of positions is that in a protein having SEQ ID NO:1; in a HA sequence a signal peptide may be from 15 to 20 residues in length, and the signal peptide in SEQ ID NO:1 is 17 residues in length). For example, SEQ ID NO:1 has a 17 amino acid signal peptide), e.g., the residue at position 87 of HA is not threonine, the residue at position 172 is not alanine, the residue at position 226 is not alanine, and/or the residue at position 279 is not alanine, or a combination thereof. In one embodiment, the isolated H5M of the invention has a residue at position 87 with an aliphatic side chain, e.g., Ile, a residue at position 172 with a hydroxyl side chain, e.g., Thr, a residue at position 226 with an aliphatic side chain, e.g., Val, and/or a residue at position 279 with a hydroxyl side chain, e.g., Thr. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine.

In one embodiment, the recombinant nucleic acid molecule or virus of the invention encodes one or more influenza viral proteins (polypeptides) having at least 95%, e.g., 96%, 97%, 98% or 99%, amino acid sequence identity to one of SEQ ID NOs:1-14, so long as the polypeptide is immunogenic. An amino acid sequence having at least 95%, e.g., 96%, 97%, 98% or 99%, amino acid sequence identity includes sequences with deletions or insertions, and/or substitutions, e.g., conservative substitutions, so long as the polypeptide is immunogenic. In one embodiment, the one or more residues which are not identical may be nonconservative substitutions. In one embodiment, the polypeptide has one or more, for instance, 2, 5, 10, 15, 20 or more, amino acid substitutions, e.g., conservative substitutions of up to 5% of the residues of the full-length, mature form of a polypeptide having SEQ ID NOs:1-14. In one embodiment, the isolated recombinant nucleic acid molecule includes a nucleic acid sequence for the mosaic antigen that has codon optimized sequences, a reduced number of RNA secondary structures, a reduced number of RNA destabilization sequences, and/or a reduced number of or no transcription terminator sequences, relative to an unmodified nucleotide sequence. The isolated recombinant nucleic acid molecule or virus, or isolated mosaic polypeptide, of the invention may be employed alone or with one or more other immunogenic agents, such as other virus in a vaccine, to raise virus-specific antisera, in gene therapy, and/or in diagnostics.

The isolated recombinant nucleic acid molecule of the invention may be employed in a vector to express influenza proteins, e.g., for recombinant protein vaccine production or to raise antisera, as a nucleic acid vaccine, for use in diagnostics or, for vRNA production, to prepare chimeric genes, e.g., with other viral genes including other influenza virus genes, and/or to prepare recombinant virus. Thus, the invention also provides isolated viral polypeptides, recombinant virus, and host cells contacted (e.g., infected or transfected) with the nucleic acid molecule(s) and/or recombinant virus of the invention, as well as isolated virus-specific antibodies, for instance, obtained from mammals infected with the virus or immunized with an isolated viral polypeptide or polynucleotide encoding one or more viral polypeptides.

The invention also provides a method to induce an immune response in a mammal, e.g., to immunize a mammal, or an avian against one more influenza virus isolates. An immunological response to a composition or vaccine is the development in the host organism of a cellular and/or antibody-mediated immune response to a viral polypeptide, e.g., an administered viral preparation, polypeptide or one encoded by an administered nucleic acid molecule, which can prevent or inhibit infection to closely structurally related viruses as well as more distantly related viruses. Usually, such a response consists of the subject producing antibodies, B cells, helper T cells, suppressor T cells, and/or cytotoxic T cells directed specifically to an antigen or antigens included in the composition or vaccine of interest. The method includes administering to the host organism, e.g., a mammal, an effective amount of the recombinant nucleic acid molecule, protein or virus of the invention, e.g., an attenuated live virus, optionally in combination with an adjuvant and/or a carrier, e.g., in an amount effective to prevent or ameliorate infection of an animal, such as a mammal, by a plurality of different influenza viruses, e.g., from different clades and/or subtypes. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other recombinant viruses, other antigens, additional biological agents or microbial components.

In one embodiment, a composition of the invention comprises one or more isolated proteins, or recombinant virus or cells expressing one or more proteins, including a protein of the invention, in an amount effective to elicit an anti-influenza virus response. For instance, recombinant protein may be isolated from a suitable expression system, such as bacteria, insect cells or yeast, e.g., *E. coli, L. lactis, Pichia* or *S. cerevisiae* or other bacterial, insect or yeast expression systems, or mammalian expression systems such as T-REx™ (Invitrogen). For example, to prepare isolated recombinant proteins, any suitable host cell may be employed, e.g., *E. coli* or yeast, or infected host cells, to express those proteins. Those cellular expression systems may also be employed as delivery systems, e.g., where the protein is one expressed on the cell surface or in a secreted form. A suitable cellular delivery system may be one for oral delivery. A recombinant protein useful in the compositions and methods of the invention may be expressed on the surface of a prokaryotic or eukaryotic cell, or may be secreted by that cell, and may be expressed as a fusion or may be linked to a molecule that alters solubility (e.g., prevents aggregation) or half-life, e.g., a PEGylated molecule, of the resulting chimeric molecule. In one embodiment, the composition of the invention may comprise a recombinant cell expressing one or more recombinant proteins, e.g., on the cell surface or as a secreted protein.

Optimized Sequences

Also provided is an isolated nucleic acid molecule (polynucleotide) comprising a nucleic acid sequence which is optimized for expression in at least one selected host. Optimized sequences include sequences which are codon optimized, i.e., codons which are employed more frequently in one organism relative to another organism, e.g., a distantly related organism, or balance the usage of codons so that the most frequently used codon is not used to exhaustion. Other modifications can include addition or modification of Kozak sequences and/or introns, and/or to remove undesirable sequences, for instance, potential transcription factor binding sites.

In one embodiment, the polynucleotide includes a nucleic acid sequence encoding a mosaic antigen of the invention, which nucleic acid sequence is optimized for expression in a mammalian host cell. In one embodiment, an optimized polynucleotide no longer hybridizes to a corresponding non-optimized (wild-type) sequence, e.g., does not hybridize to the non-optimized sequence under medium or high stringency conditions. The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids that are not completely complementary to one another be hybridized or annealed together. The art knows well that numerous equivalent conditions can be employed to comprise medium or low stringency conditions. Exemplary "high stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed. Exemplary "medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0× SSPE, 1.0% SDS at 42° C. when a probe of about 500 nucleotides in length is employed.

In another embodiment, the polynucleotide has less than 90%, e.g., less than 80%, nucleic acid sequence identity to a corresponding non-optimized (wild-type) sequence. Constructs, e.g., expression cassettes, and vectors comprising the isolated nucleic acid molecule, e.g., with optimized nucleic acid sequence, as well as kits comprising the isolated nucleic acid molecule, construct or vector are also provided.

A nucleic acid molecule comprising a nucleic acid sequence encoding a mosaic antigen of the invention is optionally optimized for expression in a particular host cell and also optionally operably linked to transcription regulatory sequences, e.g., one or more enhancers, a promoter, a transcription termination sequence or a combination thereof, to form an expression cassette.

In one embodiment, a nucleic acid sequence encoding a mosaic antigen of the invention is optimized by replacing codons, e.g., at least 25% of the codons, in a wild type sequence with codons which are preferentially employed in a particular (selected) cell. Preferred codons have a relatively high codon usage frequency in a selected cell, and their introduction results in the introduction of relatively few undesirable structural attributes. Thus, the optimized nucleic acid product may have an improved level of expression due to improved codon usage frequency, and a reduced number of undesirable transcription regulatory sequences.

An isolated and optimized nucleic acid molecule may have a codon composition that differs from that of the corresponding wild-type nucleic acid sequence at more than 30%, 35%, 40% or more than 45%, e.g., 50%, 55%, 60% or more of the codons. Exemplary codons for use in the invention are those which are employed more frequently than at least one other codon for the same amino acid in a particular organism and, in one embodiment, are also not low-usage codons in that organism and are not low-usage codons in the organism used to clone or screen for the expression of the nucleic acid molecule. Moreover, codons for certain amino acids (i.e., those amino acids that have three or more codons), may include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild type or parent nucleic acid sequence in those cells.

In one embodiment of the invention, the codons that are different are those employed more frequently in a mammal. Codons for different organisms are known to the art, e.g., see www.kazusa.or.jp./codon/. A particular type of mammal, e.g., a human, may have a different set of more frequently employed codons than another type of mammal. In one embodiment of the invention, at least a majority of the codons are codons employed in mammals (e.g., humans). For example, codons employed more frequently in humans include, but are not limited to, CGC (Arg), CTG (Leu), TCT (Ser), AGC (Ser), ACC (Thr), CCA (Pro), CCT (Pro), GCC (Ala), GGC (Gly), GTG (Val), ATC (Ile), ATT (Ile), AAG (Lys), AAC (Asn), CAG (Gln), CAC (His), GAG (Glu), GAC (Asp), TAC (Tyr), TGC (Cys) and TTC (Phe). Thus, in one embodiment, nucleic acid molecules of the invention have a codon composition where at least a majority of codons are frequently employed codons in humans, e.g., CGC, CTG, TCT, AGC, ACC, CCA, CCT, GCC, GGC, GTG, ATC, ATT, AAG, AAC, CAG, CAC, GAG, GAC, TAC, TGC, TTC, or any combination thereof. For example, the nucleic acid molecule of the invention may CTG or TTG leucine-encoding codons, GTG or GTC valine-encoding codons, GGC or GGT glycine-encoding codons, ATC or ATT isoleucine-encoding codons, CCA or CCT proline-encoding codons, CGC or CGT arginine-encoding codons, AGC or TCT serine-encoding codons, ACC or ACT threonine-encoding codon, GCC or GCT alanine-encoding codons, or any combination thereof. See FIG. 13 for codon usage tables for four different organisms.

Pharmaceutical Formulations

The compositions of this invention may be formulated with conventional carriers and excipients, which will be selected in accord with ordinary practice. Aqueous formulations are prepared in sterile form, and when intended for delivery by other than oral administration, will generally be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10 or about 8 to 9, e.g., for poxviruses.

While it is possible for the active ingredients to be administered alone they may be present as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

Pharmaceutical formulations according to the present invention may include one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for intrapulmonary or nasal administration may have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of a given condition.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Exemplary unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Pharmaceutical Compositions

Pharmaceutical compositions of the present invention, suitable for inoculation, e.g., nasal, ocular, parenteral or oral administration, comprise one or more recombinant nucleic acid molecules, virus isolates, and/or isolated protein of the invention, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

For example, for influenza virus vaccines, conventional vaccines generally contain about 0.1 to 200 μg, e.g., 30 to 100 μg or 15 to about 100 ug, of influenza virus HA from each of the strains entering into their composition. The vaccine forming the main constituent of the vaccine composition of the invention may comprise a single virus encoding an influenza virus mosaic antigen, or one or more viruses encoding antigens from a combination of subtypes or combination of antigens, for example, at least two or three different influenza virus antigens, one of which is a mosaic antigen.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

As will be apparent to one skilled in the art, the optimal concentration of the active agent in a composition of the invention will necessarily depend upon the specific agent(s) used, the characteristics of the avian or mammal, the type and amount of adjuvant, if any, and/or the nature of the infection. These factors can be determined by those of skill in the medical and pharmaceutical arts in view of the present disclosure.

Specific dosages may be adjusted depending on conditions of disease, the age, body weight, ethnic background, general health conditions, sex, diet, lifestyle and/or current therapeutic regimen of the mammal, as well as for intended dose intervals, administration routes, excretion rate, and combinations of drugs. Any of the dosage forms described herein containing effective amounts are well within the bounds of routine experimentation and therefore, well within the scope of the instant disclosure.

In addition to the recombinant virus, recombinant cells or isolated protein, or combinations thereof, the composition of the invention may further comprise one or more suitable pharmaceutically acceptable carriers. As used herein, the term "pharmaceutically acceptable carrier" refers to an acceptable vehicle for administering a composition to mammals comprising one or more non-toxic excipients which do not react with or reduce the effectiveness of the pharmacologically active agents contained therein. The proportion and type of pharmaceutically acceptable carrier in the composition may vary, depending on the chosen route of administration. Suitable pharmaceutically acceptable carriers for the compositions of the present disclosure are described in the standard pharmaceutical texts. See, e.g., "Remington's Pharmaceutical Sciences", 18$^{th}$ Ed., Mack Publishing Company, Easton, Pa. (1990). Specific non-limiting examples of suitable pharmaceutically acceptable carriers include water, saline, dextrose, glycerol, ethanol, or the like and combinations thereof.

Optionally, the composition may further comprise minor amounts of auxiliary substances such as agents that enhance the effectiveness of the preparation, stabilizers, preservatives, and the like.

In one embodiment, the composition may also comprise a bile acid or a derivative thereof, in particular in the form of a salt. These include derivatives of cholic acid and salts thereof, in particular sodium salts of cholic acid or cholic acid derivatives. Examples of bile acids and derivatives thereof include cholic acid, deoxycholic acid, chenodeoxycholic acid, lithocholic acid, ursodeoxycholic acid, hyodeoxycholic acid and derivatives such as glyco-, tauro-, amidopropyl-1-propanesulfonic-, amidopropyl-2-hydroxy-1-propanesulfonic derivatives of the aforementioned bile acids, or N,N-bis(3Dgluconoamidopropyl) deoxycholamide. A particular example is sodium deoxycholate (NaDOC).

Examples of suitable stabilizers include protease inhibitors, sugars such as sucrose and glycerol, encapsulating polymers, chelating agents such as ethylene-diaminetetracetic acid (EDTA), proteins and polypeptides such as gelatin and polyglycine and combinations thereof.

Optionally, the composition may further comprise an adjuvant in addition to the recombinant virus, recombinant cells or isolated protein described herein. Suitable adjuvants for inclusion in the compositions of the present disclosure include those that are well known in the art, such as complete Freund's adjuvant (CFA) that is not used in humans, incomplete Freund's adjuvant (IFA), squalene, squalane, alum, and various oils, all of which are well known in the art, and are available commercially from several sources, such as Novartis (e.g., Novartis' MF59 adjuvant).

Depending on the route of administration, the compositions may take the form of a solution, suspension, emulsion, or the like. A composition of the invention can be administered intranasally or through enteral administration, such as orally, or through subcutaneous injection, intra-muscular injection, intravenous injection, intraperitoneal injection, or intra-dermal injection to a mammal, e.g., humans, horses, other mammals, etc. Compositions may be formulated for a particular route of delivery, e.g., formulated for oral delivery.

For parenteral administration, the composition of the invention may be administered by intravenous, subcutaneous, intramuscular, intraperitoneal, or intradermal injection, and may further comprise pharmaceutically accepted carriers. For administration by injection, the composition may be in a solution in a sterile aqueous vehicle which may also contain other solutes such as buffers or preservatives as well as sufficient quantities of pharmaceutically acceptable salts or of glucose to make the solution isotonic.

The composition may be delivered to the respiratory system, for example to the nose, sinus cavities, sinus membranes or lungs, in any suitable manner, such as by inhalation via the mouth or intranasally. The composition may be dispensed as a powdered or liquid nasal spray, suspension, nose drops, a gel or ointment, through a tube or catheter, by syringe, by packtail, by pledget, or by submucosal infusion. The composition may be conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the composition and a suitable powder base such as lactose or starch. Examples of intranasal formulations and methods of administration can be found in PCT publications WO 01/41782, WO 00/33813, and U.S. Pat. Nos. 6,180,603; 6,313,093; and 5,624,898, all of which are incorporated herein by reference and for all purposes. A propellant for an aerosol formulation may include compressed air, nitrogen, carbon dioxide, or a hydrocarbon based low boiling solvent. The composition of the invention may be conveniently delivered in the form of an aerosol spray presentation from a nebulizer or the like. In some aspects, the active ingredients are suitably micronized so as to permit inhalation of substantially all of the active ingredients into the lungs upon administration of the dry powder formulation, thus the active ingredients will have a particle size of less than 100 microns, desirably less than 20 microns, such as in the range 1 to 10 microns or 0.2 to 0.4 microns. In one embodiment, the composition is packaged into a device that can deliver a predetermined, and generally effective, amount of the composition via inhalation, for example a nasal spray or inhaler.

The vaccines of the present disclosure may further comprise one or more suitable pharmaceutically acceptable carriers. As used herein, the term "pharmaceutically acceptable carrier" refers to an acceptable vehicle for administering a vaccine to mammals comprising one or more non-toxic excipients which do not react with or reduce the effectiveness of the pharmacologically active agents contained therein. The proportion and type of pharmaceutically acceptable carrier in the vaccine may vary, depending on the chosen route of administration. Suitable pharmaceutically acceptable carriers for the vaccines of the present disclosure are described in the standard pharmaceutical texts. See, e.g., "Remington's Pharmaceutical Sciences", $18^{th}$ Ed., Mack Publishing Company, Easton, Pa. (1990). Specific non-limiting examples of suitable pharmaceutically acceptable carriers include saline (e.g., PBS), dextrose, glycerol, or the like and combinations thereof.

In addition, if desired, the vaccine can further contain minor amounts of auxiliary substances such as agents that enhance the antiviral effectiveness of the composition, stabilizers, preservatives, and the like.

Depending on the route of administration, the vaccine may take the form of a solution, suspension, emulsion, or the like. A vaccine of the present disclosure can be administered orally, intranasally, or through parenteral administration, such as through sub-cutaneous injection, intra-muscular injection, intravenous injection, intraperitoneal injection, or intra-dermal injection to a mammal, e.g., humans, horses, other mammals, etc. Typically, the vaccine is administered through intramuscular or intradermal injection, or orally.

For parenteral administration, the vaccines of the present disclosure may be administered by intravenous, subcutaneous, intramuscular, intraperitoneal, or intradermal injection, which optionally may further comprise pharmaceutically accepted carriers. For administration by injection, the vaccine may be a solution in a sterile aqueous vehicle which may also contain other solutes such as buffers or preservatives as well as sufficient quantities of pharmaceutically acceptable salts or of glucose to make the solution isotonic.

The vaccine may be delivered locally to the respiratory system, for example to the nose, sinus cavities, sinus membranes or lungs, in any suitable manner, such as by inhalation via the mouth or intranasally. The vaccines can be dispensed as a powdered or liquid nasal spray, suspension, nose drops, a gel or ointment, through a tube or catheter, by syringe, by packtail, by pledget, or by submucosal infusion. The vaccines may be conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the vaccine and a suitable powder base such as lactose or starch. Examples of intranasal formulations and methods of administration can be found in PCT publications WO 01/41782, WO 00/33813, and U.S. Pat. Nos. 6,180,603; 6,313,093; and 5,624,898, all of which are incorporated herein by reference and for all purposes. A propellant for an aerosol formulation may include compressed air, nitrogen, carbon dioxide, or a hydrocarbon based low boiling solvent. The vaccines of the present disclosure can be conveniently delivered in the form of an aerosol spray presentation from a nebulizer or the like. In some aspects, the active ingredients are suitably micronized so as to permit inhalation of substantially all of the active ingredients into the lungs upon administration of the dry powder formulation, thus the active ingredients will have a particle size of less than 100 microns, desirably less than 20 microns, and preferably in the range 1 to 10 microns or 0.2 to 0.4 microns. In one embodiment, the vaccine is packaged into a device that can deliver a predetermined, and generally effective, amount of the vaccine via inhalation, for example a nasal spray or inhaler.

The vaccines of the present disclosure are administered prophylactically. For instance, administration of the vaccine may be commenced before or at the time of infection. In particular, the vaccines may be administered up to about 1 month or more, or more particularly up to about 4 months or more before the mammal is exposed to the microbe. Optionally, the vaccines may be administered as soon as 1 week before infection, or more particularly 1 to 5 days before infection.

The desired vaccine dose may be presented in a single dose or as divided doses administered at appropriate intervals, for example as two, three, four or more sub-doses per day. Optionally, a dose of vaccine may be administered on one day, followed by one or more booster doses spaced as desired thereinafter. In one exemplary embodiment, an initial vaccination is given, followed by a boost of the same vaccine approximately one week to 15 days later.

The dosage of a live virus vaccine for an animal such as a mammalian adult organism can be from about $10^2$-$10^{15}$, e.g., $10^3$-$10^{12}$, plaque forming units (PFU)/kg, or any range or value therein. For poxviruses that express influenza virus HA, the dosage of PFU or immunoreactive HA in each dose of replicated virus vaccine may be standardized to contain a suitable amount, e.g., 30 to 100 μg, such as 15 to 100 ug, or any range or value therein, or the amount recommended by government agencies or recognized professional organizations. If the poxvirus expresses a different influenza virus protein, that protein may be standardized. For example, the quantity of NA may also be standardized, however, this glycoprotein may be labile during purification and storage.

The invention will be further described by the following non-limiting examples.

Example I

Materials and Methods

Cells and Viruses

Chicken embryo fibroblasts (CEFs) and Mardin-Darby canine kidney (MDCK) cells were obtained from Charles River Laboratories, Inc. (Wilmington, Wash.) and the American Type Culture Collection (ATCC, Manassas, Va.), respectively. Cells were cultured in Dulbecco's Modified Eagle's Medium (DMEM) supplemented with 10% fetal bovine serum (FBS) and antibiotics. CEFs were used for propagating MVA virus. Highly pathogenic avian influenza (H5N1) virus A/Vietnam/1203/04 was kindly provided by Dr. Yoshihiro Kawaoka (University of Wisconsin-Madison, Wis., USA). Highly pathogenic avian influenza (H5N1) viruses, A/Hongkong/483/97, A/Mongolia/Whooper swan/244/05 and A/Egypt/1/08 and seasonal influenza viruses including A/Puerto Rico/8/34 (PR8, H1N1) and A/Aichi/2/1968 (H3N2) were kindly provided by Dr. Stacey Schultz-Cherry and Dr. Ghazi Kayali (St. Jude children's research hospital, Memphis, Tenn.). All viruses were propagated and titrated in MDCK cells with DMEM that contained 1% bovine serum albumin and 20 Mm HEPES. Viruses were stored at −80° C. until use. Viral titers were determined and expressed as 50% tissue culture infective dose ($TCID_{50}$). All experimental studies with HPAI H5N1 viruses were conducted in a BSL3+ facility in compliance with the UW Madison Office of Biological Safety.

Plasmid and MVA Recombinant Vaccine Construction.

A total of 3,069 HA protein sequences from H5N1 viruses available in National Center for Biotechnology Information (NCBI) database were downloaded and screened to exclude incomplete and redundant sequences. The resulting 2,145 HA sequences were selected to generate one mosaic protein sequence as previously described (Fischer et al., 2007). T cell epitopes were set to 12 amino acid length (12-mer) in an attempt to match the length of natural T helper cell epitopes (Goglak et al., 2000). The resulting mosaic H5N1 sequence (H5M) was back-translated and codon optimized for mice. The optimized H5M sequence was then synthesized commercially (GenScript USA Inc.) and cloned into MVA-shuttle vector (Brewoo et al., 2013). Recombinant MVA expressing a mosaic H5 (MVA-H5M) was generated in CEF cells as described elsewhere (Earl et al., 2001a; Earl et al., 2001b). MVA expressing wild type HA from avian influenza A/VN/1203/04 (MVA-HA) was constructed as described in Brewor et al. (2013) and kindly provided by Inviragen, Inc.

Analysis of HA Expressed by H5M

The hemagglutin expressed by MVA-H5M was analyzed by western blot analysis. CEF cells were infected with 1 multiplicity of infection (MOI) of 1 PFU/cell of MVA-H5M, MVA-HA and MVA-LUC constructs. Infected cell pellets were harvested 48 hours post-infection and lysed with Laemmli sample buffer (BioRad). Protein was fractionated via SDS PAGE and proteins were transferred onto nitrocellulose membrane for hemaggutinin detection by specific anti-HA antibody. 3,3',5,5'-tetramethylbenzidine (TMB) was used to visualized HA protein in the membranes.

Functional analysis of H5M was done by hemagglutination assay (Killian (2008)). CEF cells were infected with 1 MOI of 1 PFU/cell of MVA-H5M, MVA-HA and MVA-LUC. After 48 hours post-infection, cells were harvested and 2-fold dilutions with PBS were made in round bottom 96 well plates. Chicken red blood cells were added into each well and incubated for 30 minutes. Lattice formations were observed in positive wells which is indicative of the ability of HA to agglutinate RBC.

Animal Studies

All mouse studies were conducted at University of Wisconsin-Madison animal facilities and were approved by the Inter-institutional Animal Care and Use Committee (IACUC). Challenge experiments involving H5N1 viruses were conducted at ABSL3+ facilities. Challenge studies for seasonal influenza, A/Puerto Rico/8/34 (PR8, H1N1), and A/Aichi/2/1968 (H3N2) were conducted under the BSL2 conditions to facilitate animal monitoring.

Vaccine Efficacies

Groups of 5 week-old BALB/c mice were vaccinated with $1\times10^7$ plaque forming unit (pfu) of either recombinant MVA-H5M, or MVA-expressing luciferase (MVA-LUC) via the intradermal (ID) route. Intradermal inoculations were done by injecting 50 μL of PBS-containing virus into footpads. Four weeks after vaccination, blood samples were collected for serological analysis. At week five post vaccination, mice were challenged by intranasal (IN) instillation under isoflurane anesthesia with 100 $LD_{50}$ of A/Vietnam/1203/04 ($1\times10^4$ $TCID_{50}$), A/Hongkong/483/97 ($4\times10^3$ $TCID_{50}$), A/Mongolia/Whooper swan/244/05 virus ($1\times10^3$ $TCID_{50}$) or A/Egypt/1/08 ($3.56\times10^4$ $TCID_{50}$) contained in 20 μL of PBS. Two mice from each group were euthanized at day five post-challenge and lung tissues were collected for viral titrations and histopathology. For isolation of virus, lung tissues were minced in PBS using a mechanical homogenizer (MP Biochemicals, Solon, Ohio), and viral titers in homogenates were quantified by plaque assay on MDCK cells. The remaining lung tissue was fixed in 10% formalin. The remaining animals in each group were observed daily for 14 days, and survival and clinical parameters including clinical score and body weight were recorded. Mice showing at least 20% body weight loss were humanely euthanized.

A second study evaluated the protective efficacies of the MVA-H5M vaccine against seasonal influenza virus, PR8 (H1N1) or A/Aichi/2/1968 (H3N2). Groups of 5 week-old BALB/c mice were vaccinated with MVA-H5M or MVA-LUC as above. Four weeks after vaccination, blood samples were collected for serological analysis. At week five post vaccination, mice were challenged by intranasal (IN) instillation under isofluorane anesthesia with 50 μL of PBS containing 100 $LD_{50}$ of PR8 ($6.15\times10^3$ $TCID_{50}$) or A/Aichi/2/1968 ($5\times10^6$ $TCID_{50}$). Two mice from each group were euthanized at day three post-challenge and lung tissues were collected as above. The remaining animals in each group were observed daily for 14 days as described above.

Serology

Serum antibody titers were determined by microneutralization assay. Briefly, serum was incubated at 56° C. for 30 minutes to inactivate complement and then serially diluted two fold in microtiter plates. 200 $TCID_{50}$ units of virus were added to each well and incubated at 37° C. for 1 hour. The virus-serum mixture was added to duplicate wells of MDCK cell in 96-well plates, incubated at 37° C. for 72 hours, then fixed and stained with 10% (W/V) crystal violet in 10% (V/V) formalin to determine the $TCID_{50}$. The titer was determined as the serum dilution resulting in the complete neutralization of the virus.

Histopathology and Immunohistochemistry

Lung samples for histological analysis were processed by the histopathology laboratory at The School of Veterinary Medicine, (UW-Madison, Wis.) and stained with H&E. For immunohistochemistry, tissue sections were deparaffinized and rehydrated as previously described (Brown et al., 1992; Chamnanpood et al., 2011). Slides were treated with antigen retrieval buffer followed up with 3% $H_2O_2$. Slides were placed in blocking solution and incubated in goat-anti-HA (BEI resource # NR-2705) (1/300 dilution) avian influenza polyclonal antibody for 24 hours. Secondary HRP-conjugated anti-goat antibody at 1/5000 diluted were added onto slides and incubated for 1 hour. Then, slides were stained with 0.05% 3,3'-diaminobenzidine (DAB) substrate to visualize the presence of avian influenza antigens.

T Cell Responses

At five months post-vaccination, two MVA-H5M vaccinated mice were euthanized and spleens were aseptically removed. Splenocytes from individual animals were suspended in RPMI-1640 medium supplemented with 10% heat-inactivated fetal calf serum, 100 I.U./mL penicillin, 100 μg/mL streptomycin and 0.14 mM β-mercaptoethanol. Red blood cells were lysed with 1×BD Pharm Lyse™ buffer. Following washing with RPMI medium, cells were resuspended in the same medium and $1\times10^6$ splenocytes were surface stained with anti-mouse CD4 FITC (RM4-5) and anti-mouse CD8a PerCP (53-6.7) mAbs. In order to study intracellular cytokine responses, $1\times10^6$ splenocytes were plated onto a 96-well flat-bottom plate and stimulated with diverse H5N1 HA peptide pools (5 μg/mL) in 200 μl total volume for 16 hours. Bredfeldin A (BD GolgiPlug) was added at a final concentration of 1 μg/ml for the last 5 hrs of incubation to block protein transport. Cells were stained intracellularly for IFN-γ APC (XMG1.2) and IL-2 PE (JES6-5H4) after surface staining for CD4 and CD8a. All antibodies were from BD Bioscience except where noted. The samples were acquired on BD FACSCalibur and analyzed with FlowJo v10.0.6 (Tree star). The cytokine background from medium-treated groups was subtracted from each sample. The frequency of cytokine-positive T cells was presented as the percentage of gated $CD4^+$ or $CD8^+$ T cells.

Statistical Analysis

Student's T-tests were used to evaluate viral lung titers and antibody titers between groups. Survival analyses were performed to assess vaccine effectiveness against challenge viruses. Probability values $<0.05$ were considered significant. GraphPad Prism 6 software (La jolla, CA) was used for all statistical analyses.

Results

The use of a "genetic algorithm" (e.g., "Mosaic Vaccine Tool Suite," developed by Los Alamos National Labs for HIV work) to generate, select, and "recombine" (in silico) potential T and B cell epitopes (about 9-12 amino acids in length) into "mosaic" proteins, can provide greater coverage of global viral variants, and thus optimized immunogenicity, than any single wild-type protein. The mosaic sequence accounts for the complete or full-length sequence of the protein and/or regions of interest, as well as the full diversity of the 'core' sequences provided. The use of a mosaic sequence for an HIV-1 vaccine, which recombined potential T cell epitopes into Gag, Pol and Env proteins, has been reported (Fischer et al., 2007). Mosaic HIV-1 vaccines expanded the breadth and depth of cellular immune responses in rhesus monkeys compared to consensus sequences (Barouch et al., 2010).

Figure 2A:
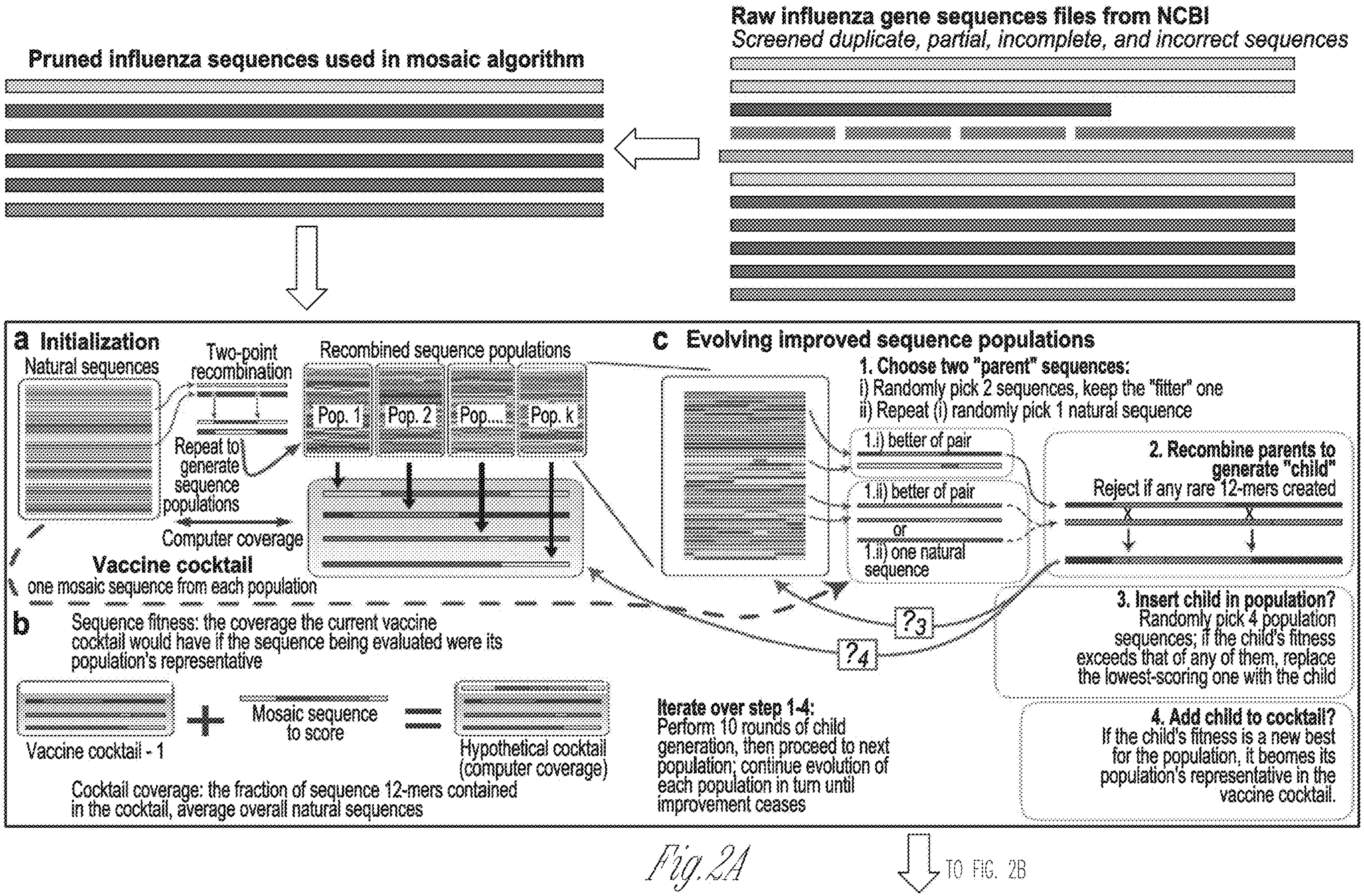
FIGS. 2A-B. Exemplary mosaic vaccine approach.
Figure 2B:
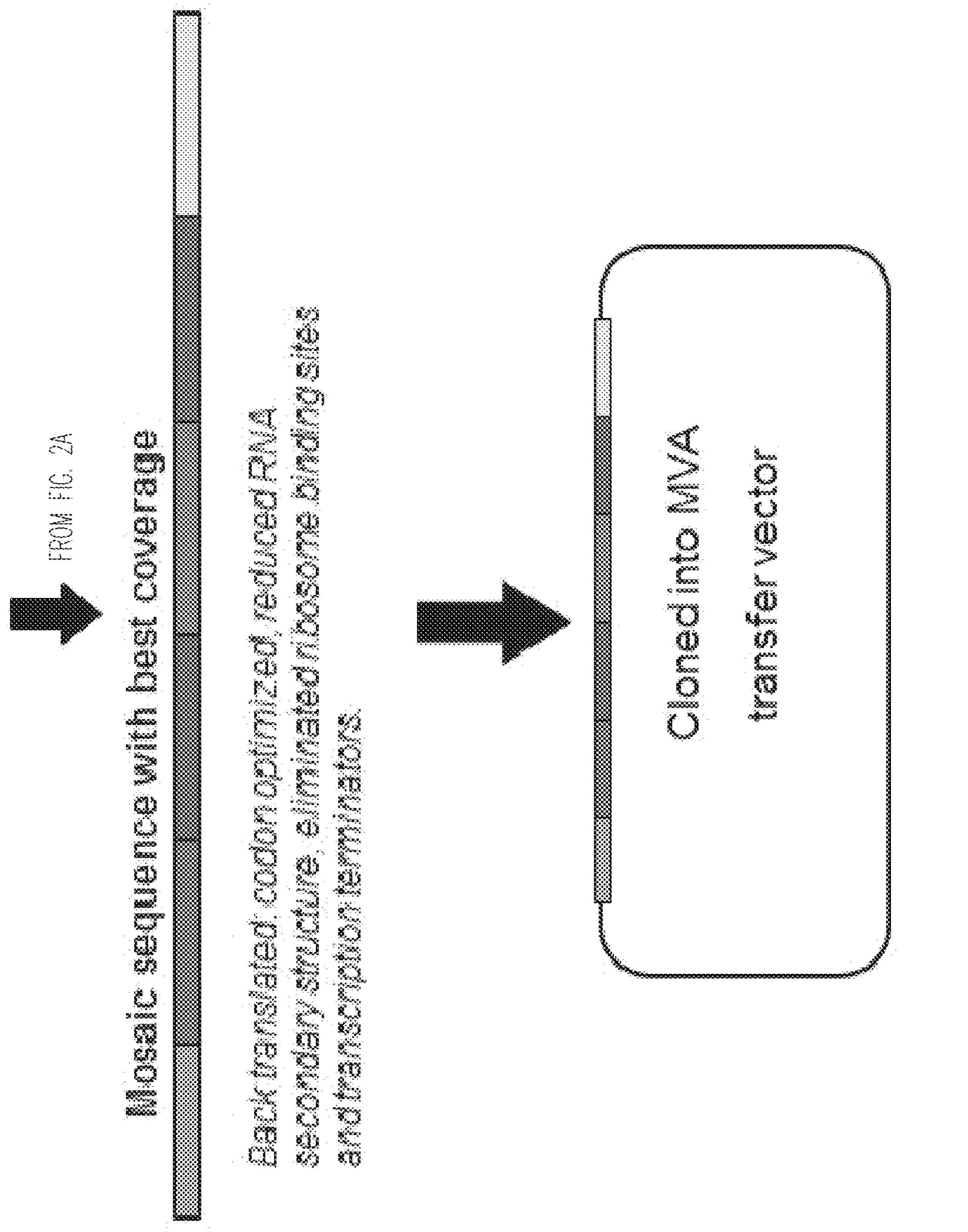

FIG. 2 is a schematic of an exemplary mosaic vaccine approach. Natural sequences, e.g., from field isolates and not from viruses passed in culture, that represent the diversity found in current or currently circulating strains, and that represent a specific subtype are selected. Repeats of sequences are eliminated. Recombined sequence populations (about 500) are generated in silico and the coverage of a sequence from each population is compared to the natural sequence, e.g., as if it were the representative sequence for the population. A representative mosaic sequence from each population is evaluated for its fitness. Representative sequences with rare T cell epitopes are generally excluded. To further evolve the sequences, parent mosaic sequences, e.g., pairs of random parental sequences, can be recombined in silico to generate child sequences. The fitness of one or more random child sequences is/are determined and if the fitness has better coverage of the input sequences, the parental with the lowest score is replaced with the higher scoring child sequence or, if the child score is the highest for the population, it is the representative for that population. The scoring of representative sequences in a population may be repeated until the fitness is no longer being improved, e.g., for a number of cycles such as 10 cycles.

Construction of Pox-Based H5N1 Mosaic Hemagglutinin Vaccine

Figure 3:
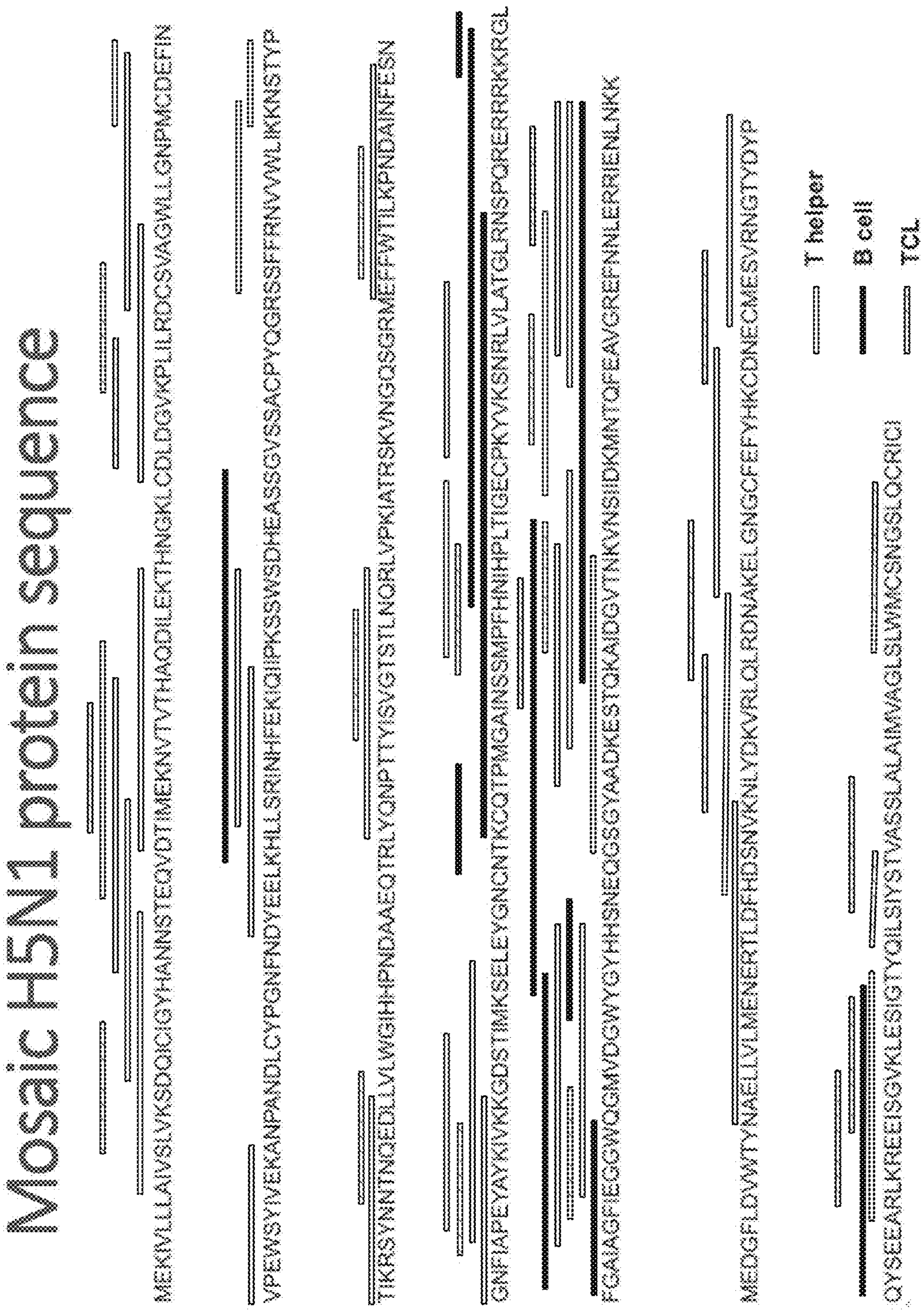
FIG. 3. Exemplary mosaic (synthetic) H5 protein sequence (SEQ ID NO:1). The mosaic H5N1 hemagglutinin (H5M) sequence was deduced from 2, 145 HA sequences. Lines above the sequence indicate known T-helper cell (blue), B-cell (green) or TCL (Red) epitopes that were found in the H5M (Influenza research database (IRD)).
Figure 5A:
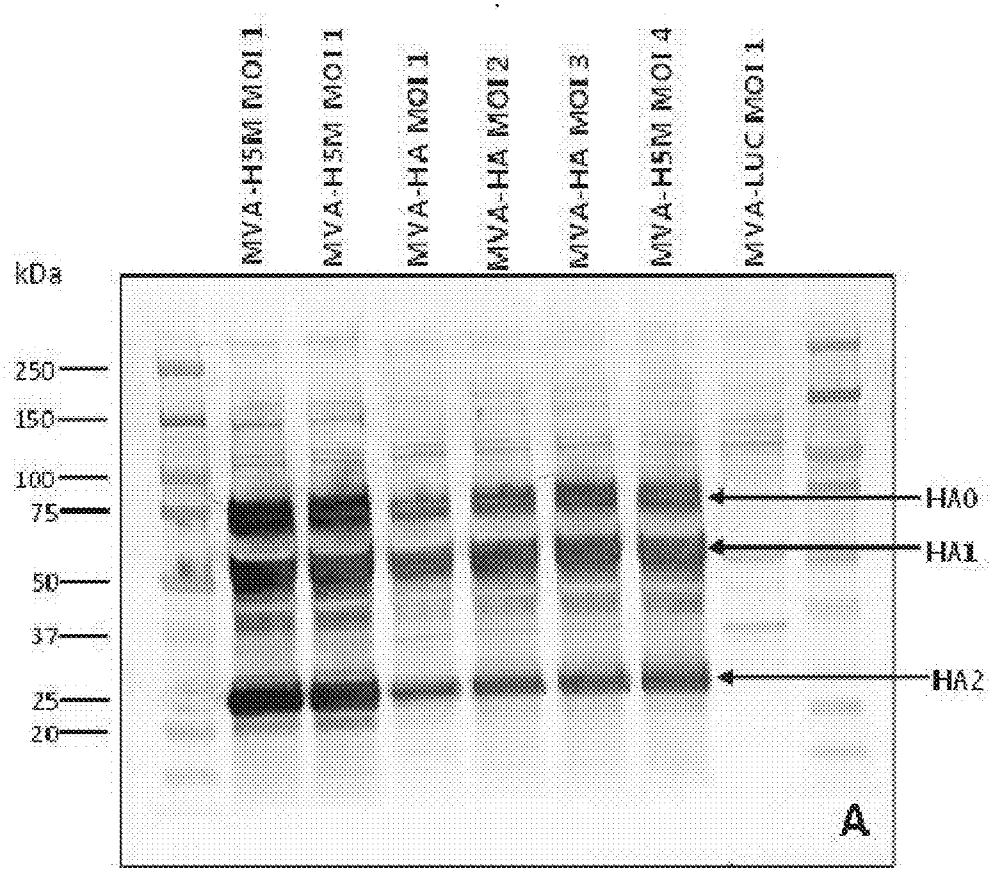
FIGS. 5A-B. MVA-H5M vaccine expresses higher level of protein than MVA expressing wild type hemaggutinin (MVA-HA) and elicits broad neutralizing antibodies against avian influenza viruses. (A) Western blot analysis of MVA-H5M, MVA-HA and MVA-LUC (negative control) infected CEF cell lysates. HA from MVA-H5M was expressed as a cleavable protein as same as HA wildtype of MVA-HA. The sizes of HA0, HA1 and HA2 are 75 kDa, 50 kDa and 25 kDa, respectively. (B) Neutralizing antibody titers of vaccinated mice were measured at 4 week post-vaccination against influenza A/VN/1203/04, A/MG/244/05, A/HK/483/97, A/Egypt/1/08, PR8 (H1N1) or A/Aichi/2/1968 (H3N2) virus.

A mosaic vaccine that targets the hemagglutinin protein of influenza H5N1 virus was constructed. The HA mosaic was generated using an input of 2,145 HA sequences from H5N1 influenza viruses available in GenBank. To maximize T helper cell epitope coverage, the in silico algorithm was set to an amino acid length of 12 mer (Gogolak et al., 2000). HA sequences from H5N1 strains (2,145 sequences) were used to generate a mosaic sequence (FIG. 3): MEKIVLLLAIVS-LVKSDQICIGYHANNSTEQVDTIMEKNVT-VTHAQDILEKTHNGKLCDLDGVKPLILRDCSV AGWLLGNPMCDEFINVPEWSYIVEKANPANDLCY-PGNFNDYEELKHLLSRINHFEKIQIIPKSSWSDHEAS SGVSSACPYQGRSSFFRNVVWLIKKNSTYP-TIKRSYNNTNQEDLLVLWGIHHPNDAAEQTRLY-QNPTTYI SVGTSTLNQRLVPKIATRSKVNGQSGRM-EFFWTILKPNDAINFESNGNFIAPEYAYKIVKK GDSTIMKSELE YGNCNTKCQTPMGAINSSMPFHNIH-PLTIGECPKYVKSNRLVLATGLRNSPQRERRRK-KRGLFGAIAGFIE GGWQGMVDGWYGYHHSNEQGS-GYAADKESTQKAIDGVTNKVNSIIDKMNT QFEAVGREFNNLERRIEN LNKKMEDGFLDVW-TYNAELLVLMENERTLDFHDSNVKNLYDKVRLQL-RDNAKELGNGCFEFYHKCDNEC MESVRNGTY-DYPQYSEEARLKREEISGVKLESIGTYQILSIYS TVASSLALAIMVAGLSLWMCSNGSLQCRI CI (SEQ ID NO:1). The mosaic H5 (H5M) sequence was back-translated into DNA and cloned into Modified Vaccinia Ankara (MVA) to generate MVA-H5M. That nucleotide sequence may be altered to improve expression, e.g., by codon optimization for mammalian cells such as mice (the model for testing), eliminating RNA secondary structure, eliminating RNA destabilization sequences, removing transcription termination sequences (e.g., TTTTTNT), and/or adding a Kozak sequence to the 5' end. The poxvirus encoding H5M was used to infect chicken embryo fibroblasts and supernatants that were harvested 48 hours after infection were analyzed by Western blot (FIG. 5). Recombinant H5M was expressed as cleavable HA that resembled a wild-type (wt) HA from avian influenza A/VN/1203/04. Interestingly, the level of protein expression from MVA-H5M infected cell pellets was higher than the MVA expressing wild-type hemagglutinin from A/VN/1203/04 (MVA-HA) (Brewoo et al., 2013) (FIG. 5). Additionally, in vitro functional analysis of H5M resulted in hemaglutination of RBC at similar levels to wt HA (data not shown). These data thus demonstrate the successful generation of an MVA vector expressing a mosaic H5N1 HA gene.

Efficacy of MVA-H5M Vaccine Against Influenza Viruses

Figure 13A:
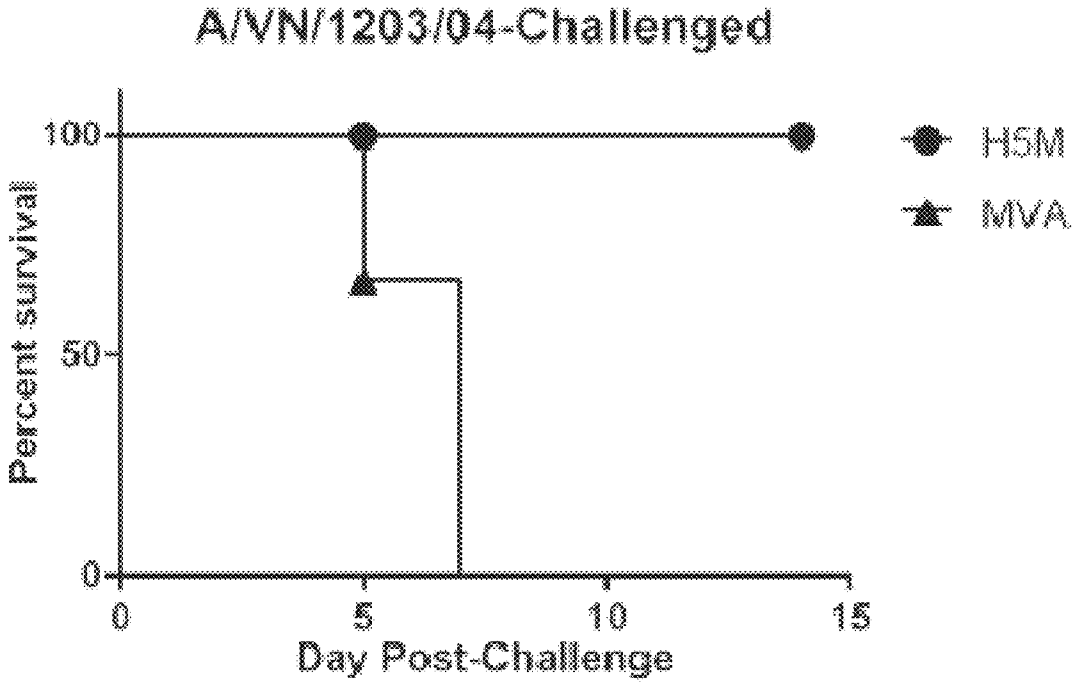
FIGS. 13A-N. MVA-H5M provides broad protection against multiple clades of avian influenza virus, and H1N1 virus. Vaccine efficacies of a single dose of MVA-H5M or MVA-LUC against highly pathogenic avian influenza viruses (A-G, J and M) and seasonal influenza viruses (H-I, K-L and N). Vaccinated mice were challenged at week 5 post-vaccination, and survival data were monitored for 14 days (n=8 per group).
Figure 13B:
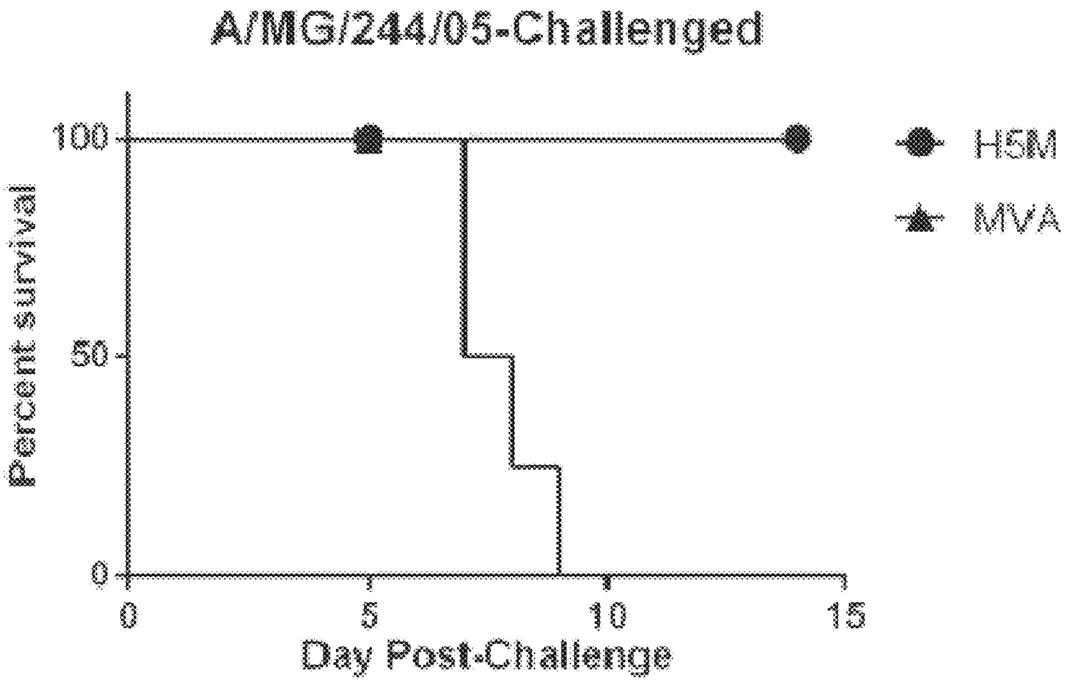
Figure 13C:
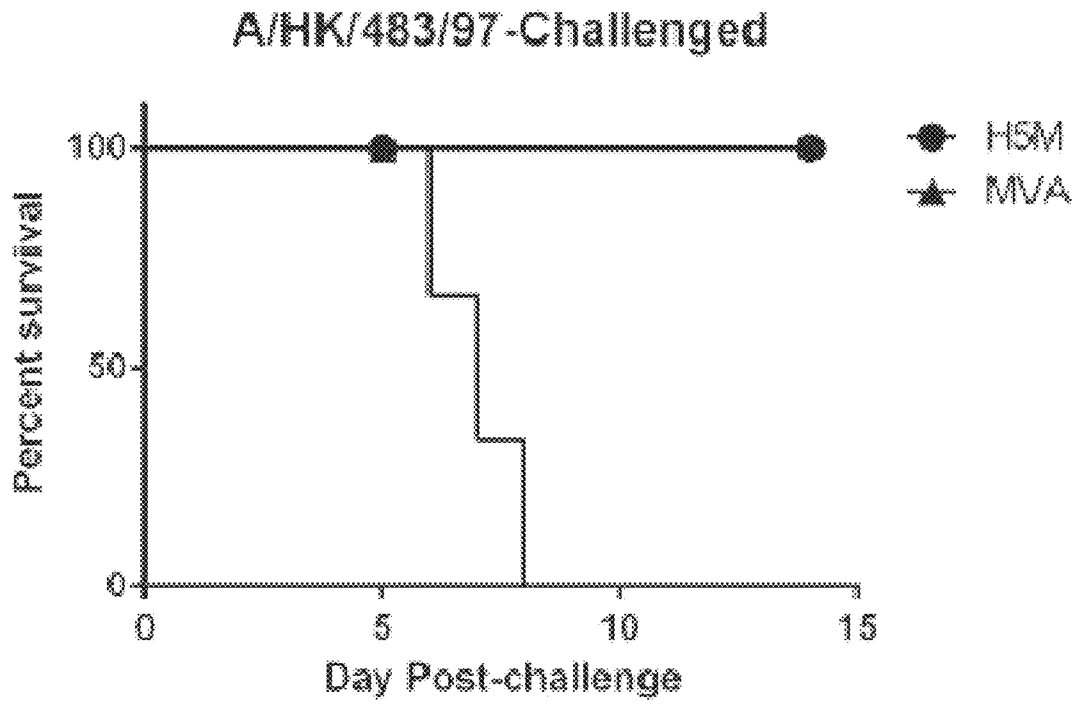
Figure 13D:
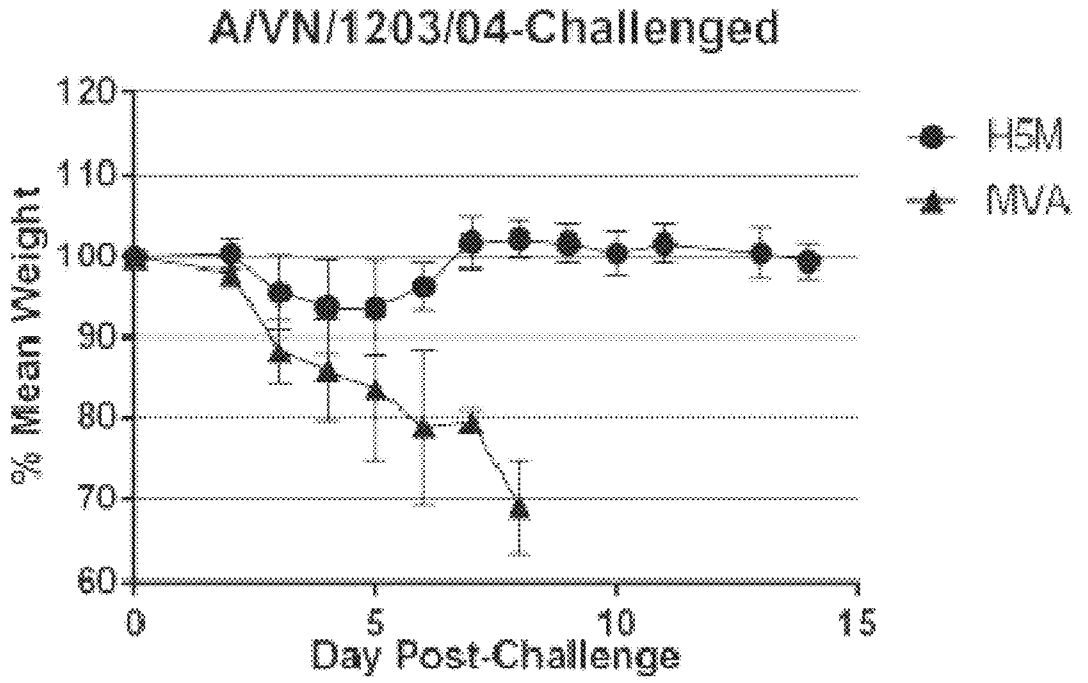
Figure 13E:
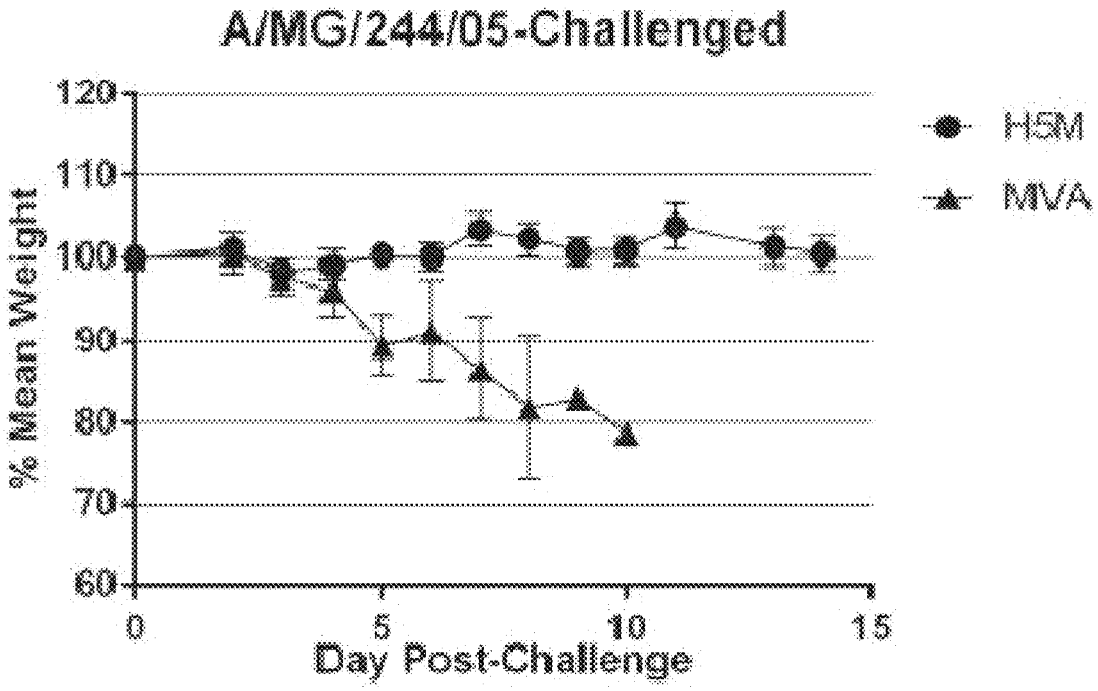
Figure 13F:
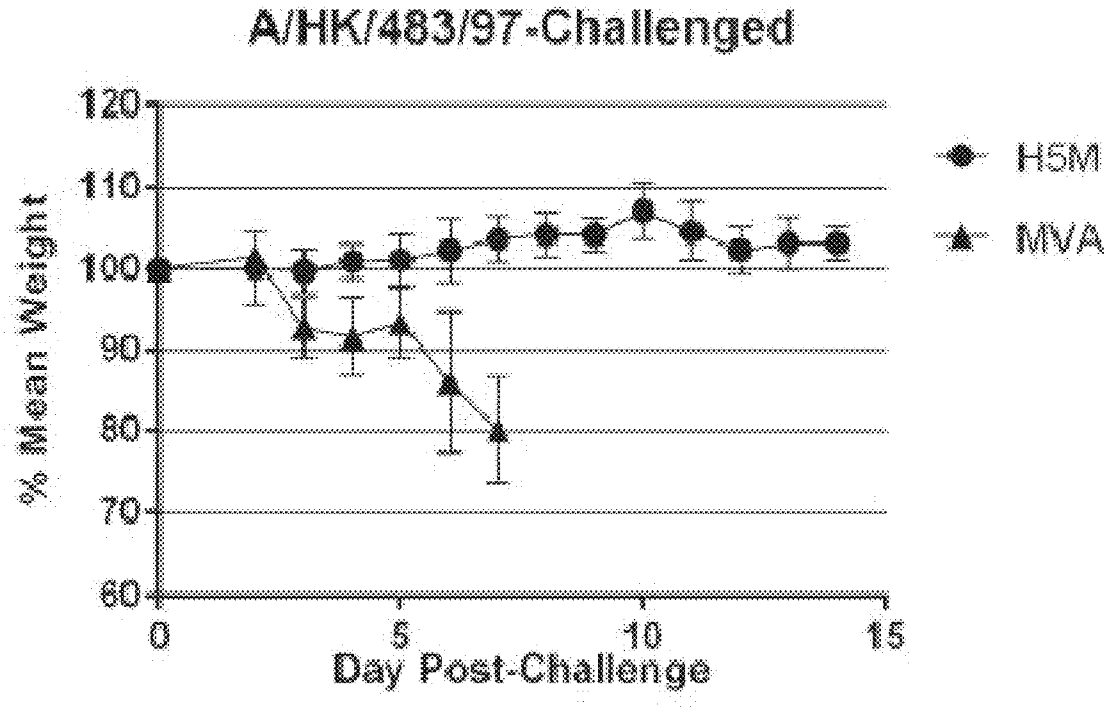
Figure 13G:
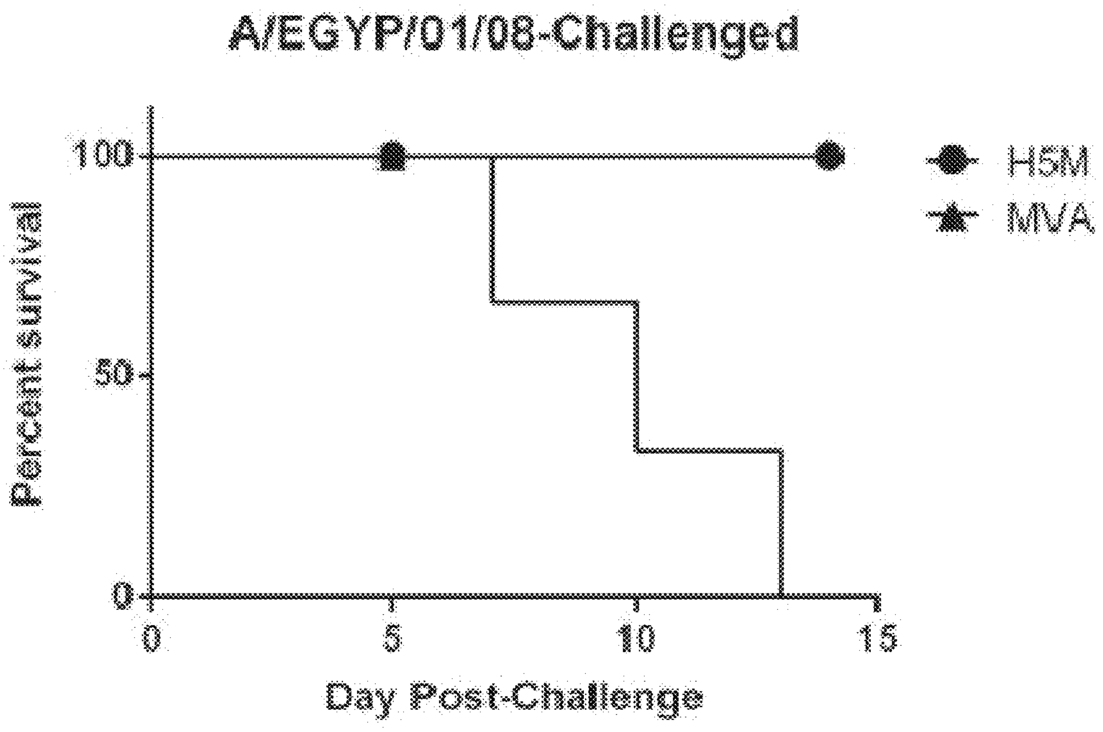
Figure 13H:
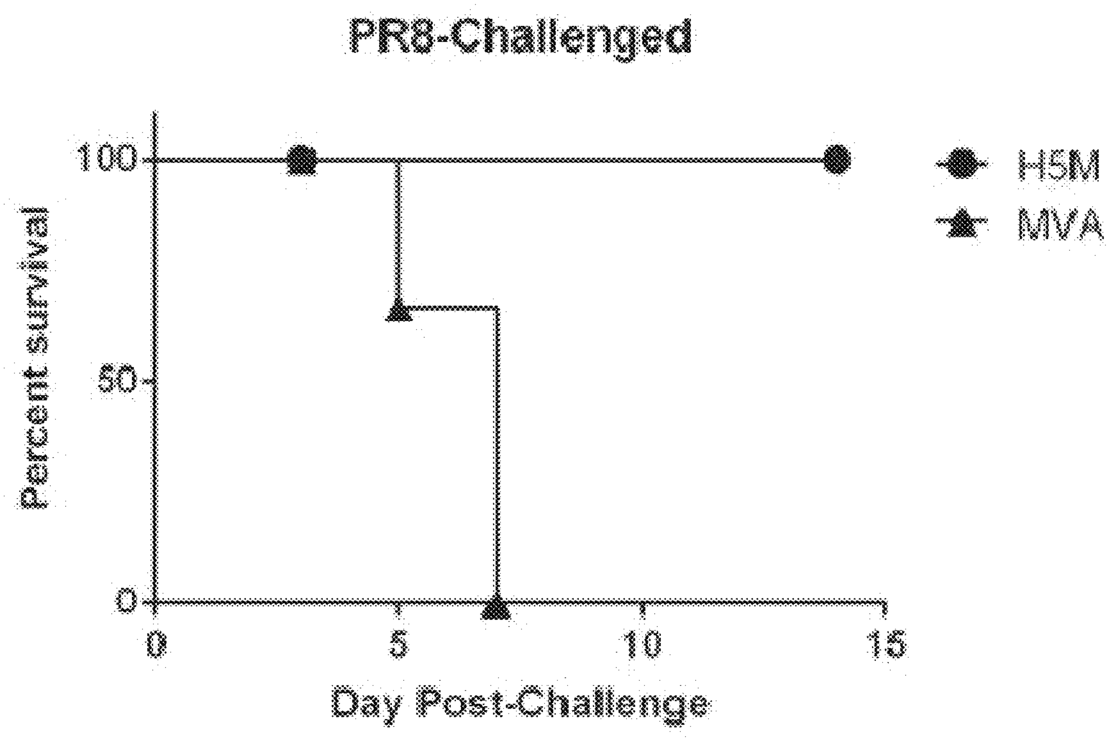
Figure 13I:
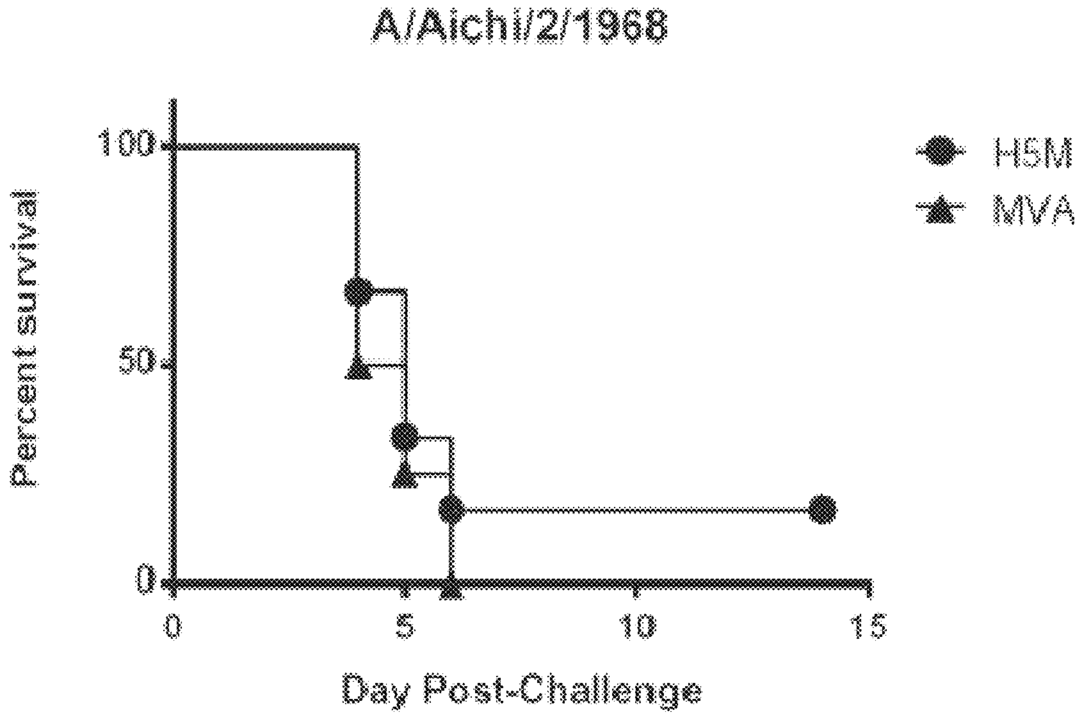
Figure 13J:
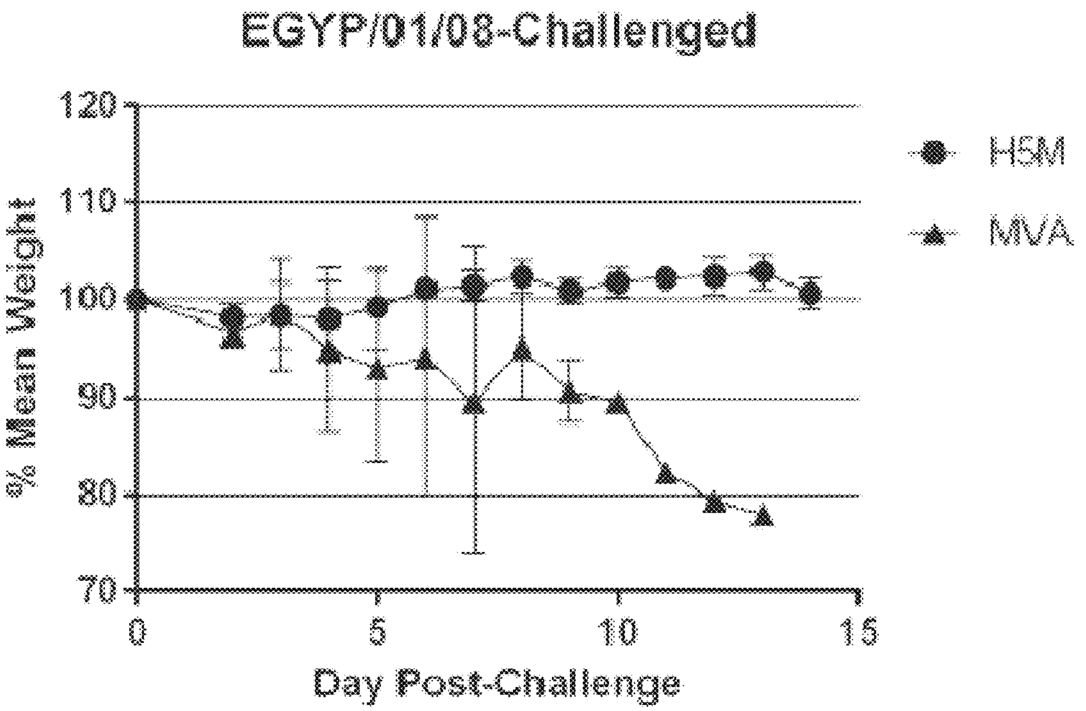
Figure 13K:
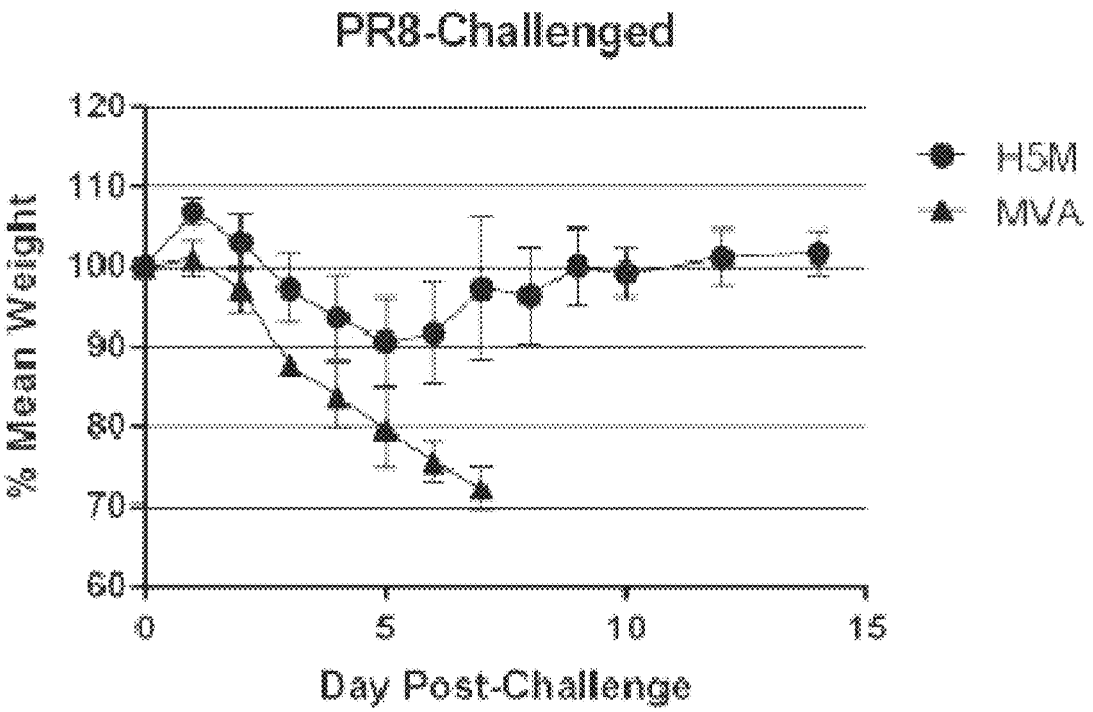
Figure 13L:
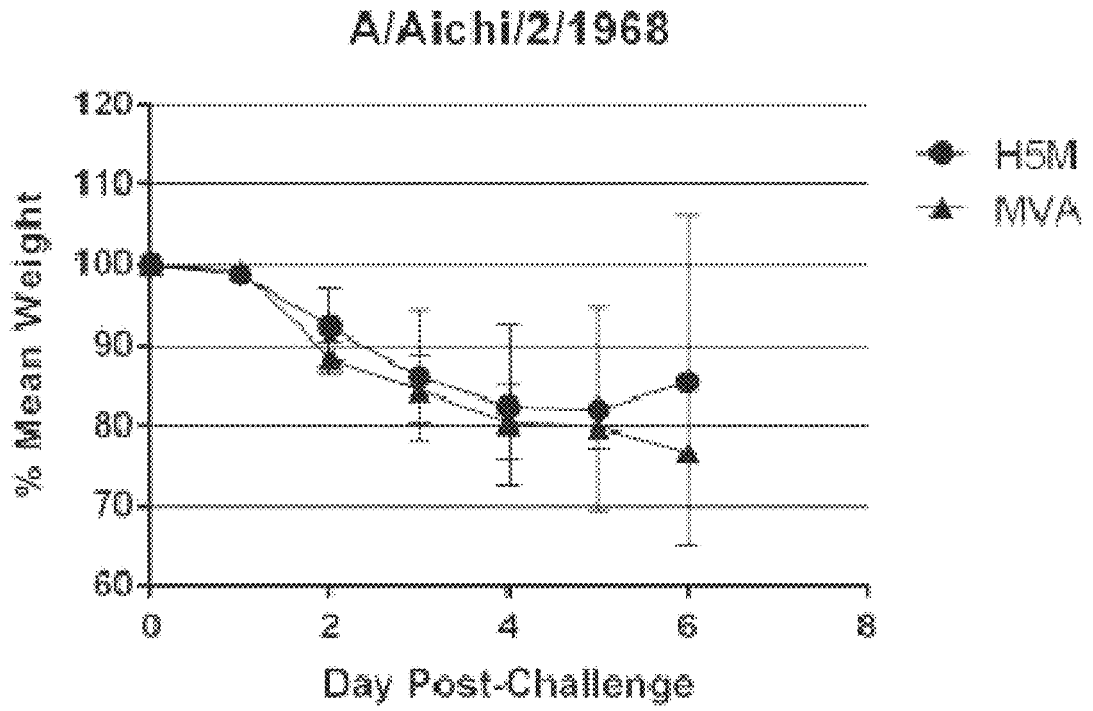
Figure 13M:
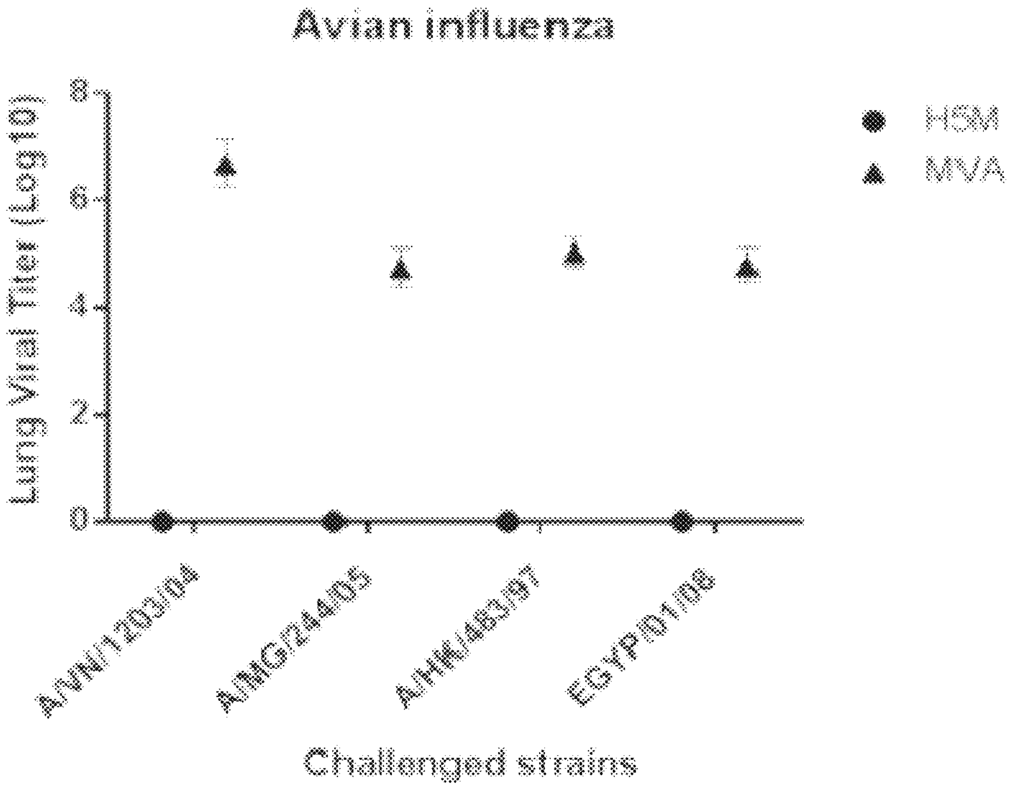
Figure 16:
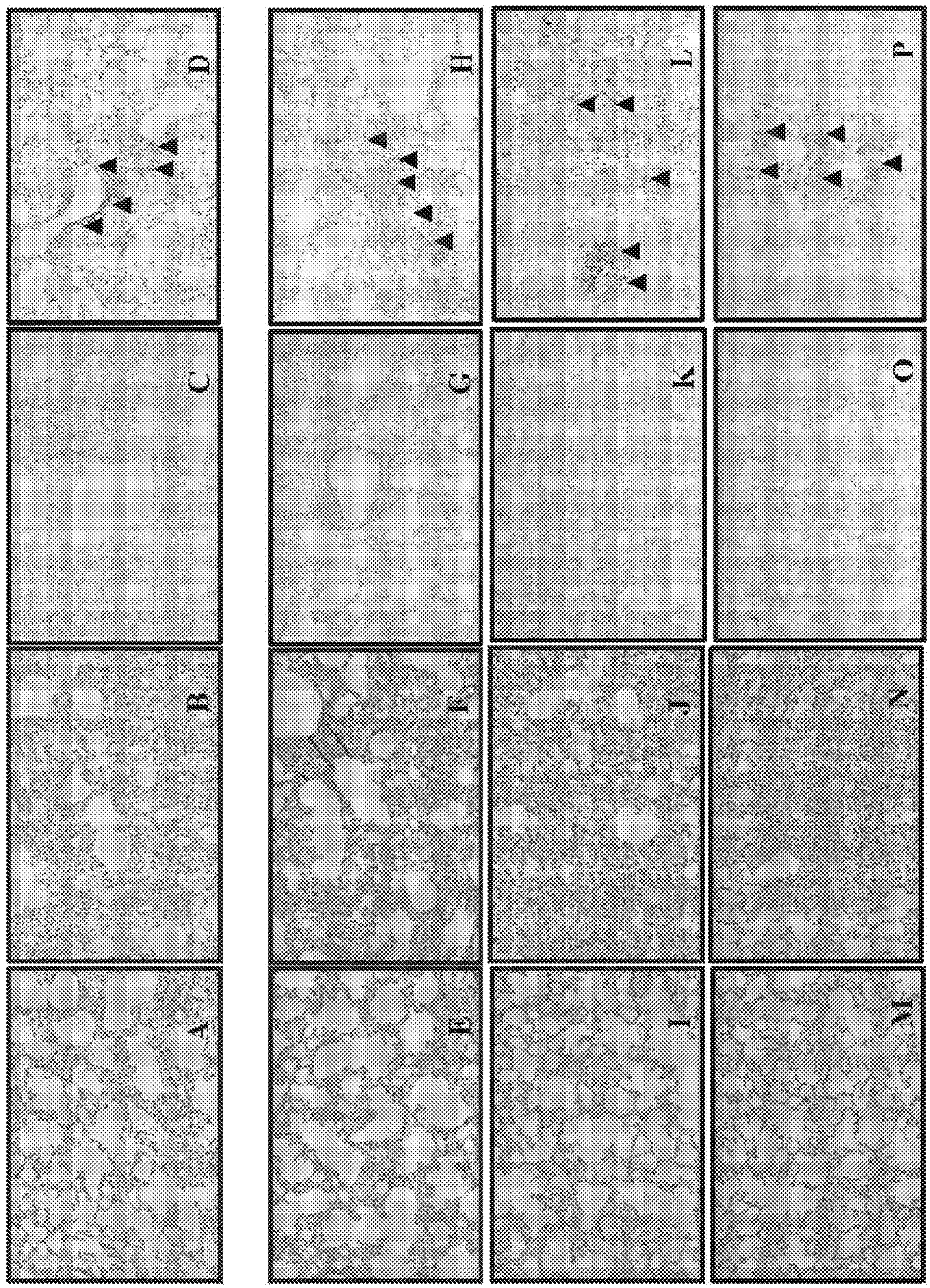
FIG. 16. MVA-H5M reduces lung pathology and prevents viral replication in the lung after challenged with avian influenza viruses. Lungs of mice vaccinated with MVA-H5M (A, E, I, M, C, G, K and O) or MVA-LUC (B, F, J, N, D, H, L and P), challenged with A/VN/1203/04 (A-D), A/MG/244/05 (E-H), A/HK/483/97 virus (I-L) or A/Egypt/1/08 (M-P). MVA-H5M vaccinated mice showed normal to mild lung lesions compared to MVA-LUC-vaccinated mice, which showed severe lung lesions including lung consolidation, WBCs infiltration, thickening of alveolar septa and alveolar edema. Lungs from mice that were administered MVA-H5M (C, G, K and O) or MVA-LUC (D, H, L and P) were processed by immunohistochemistry with H5N1 specific antibody. Brown staining for viral antigen is indicated with arrow heads.
Figure 18A:
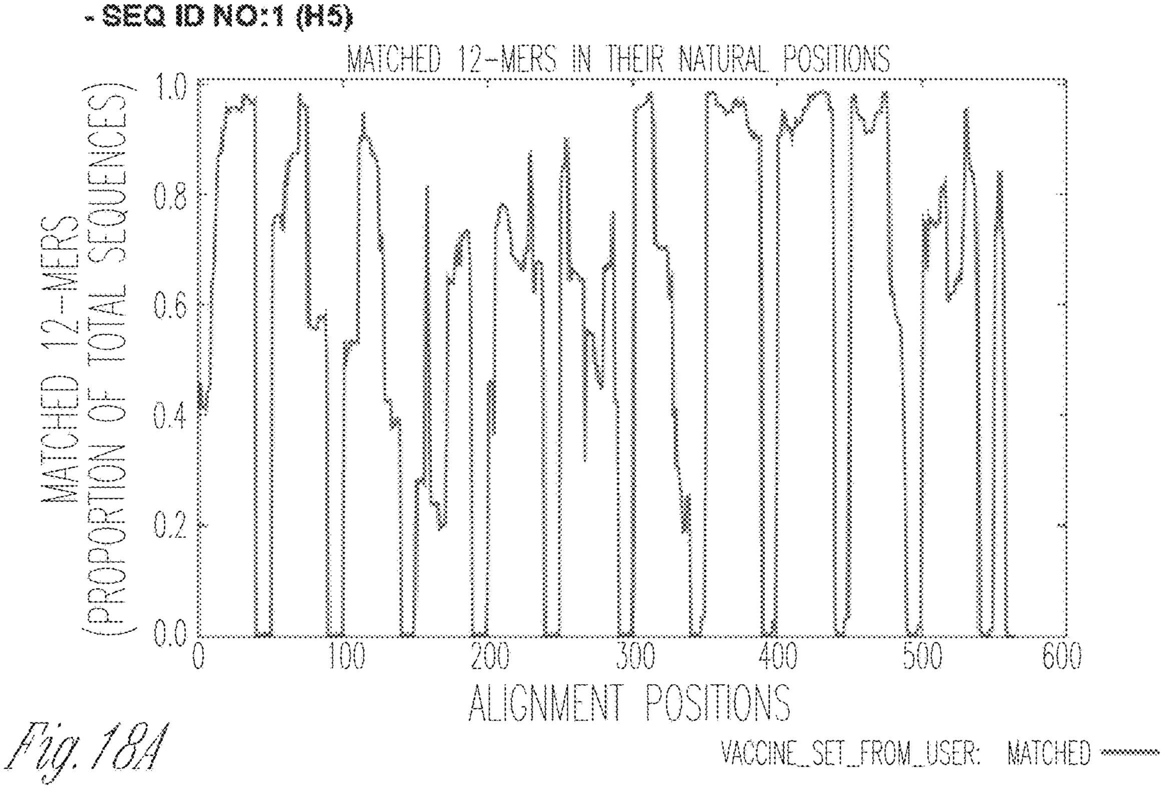
FIGS. 18A-N. Conserved motifs in some of the sequences shown in FIG. 11. With regard to sequences that are related but include one or more substitutions to those sequences, those substitutions may be in the conserved regions but generally not in any signature residue.
Figure 18B:
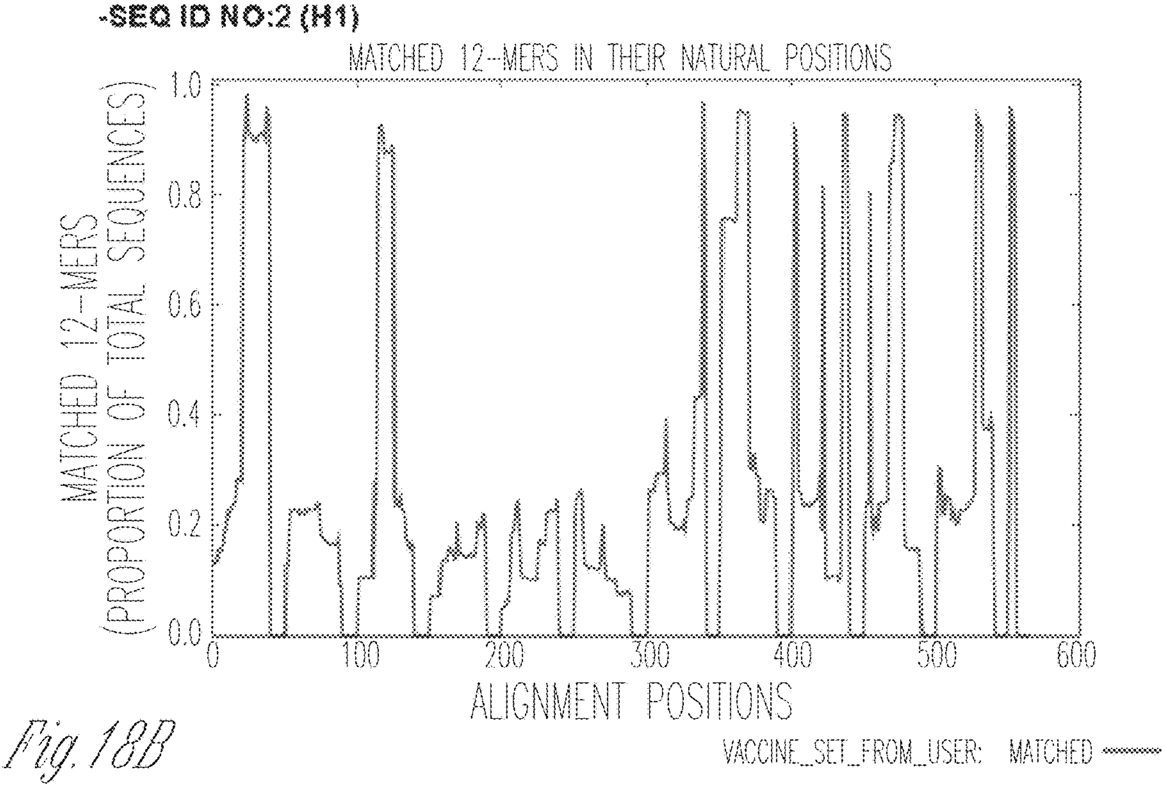
Figure 18C:
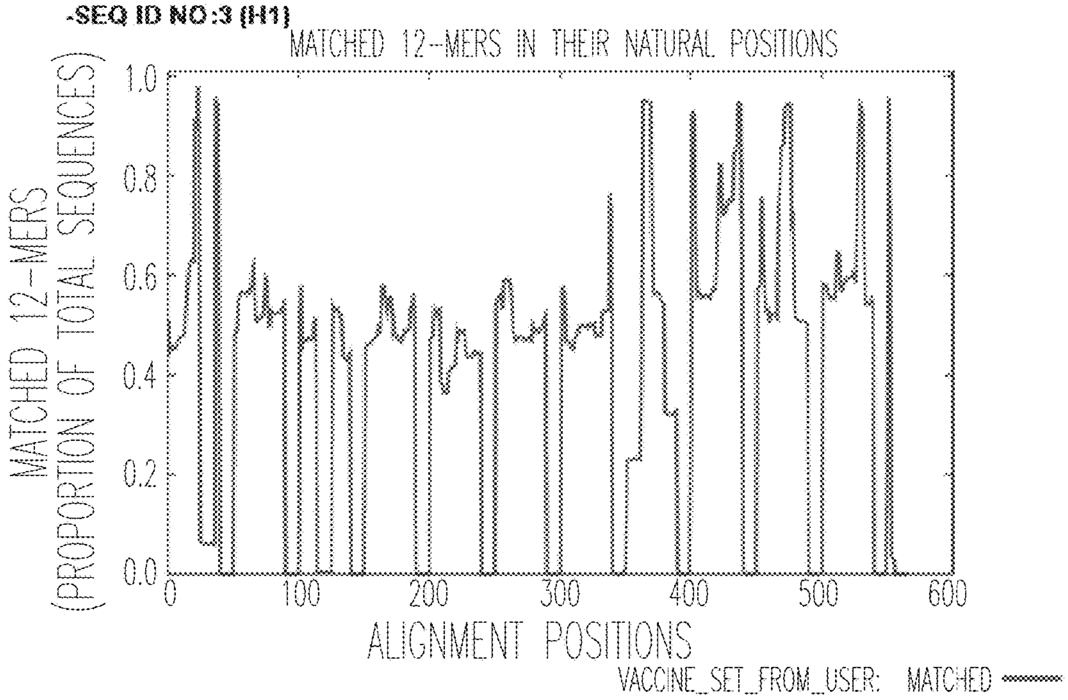
Figure 18D:
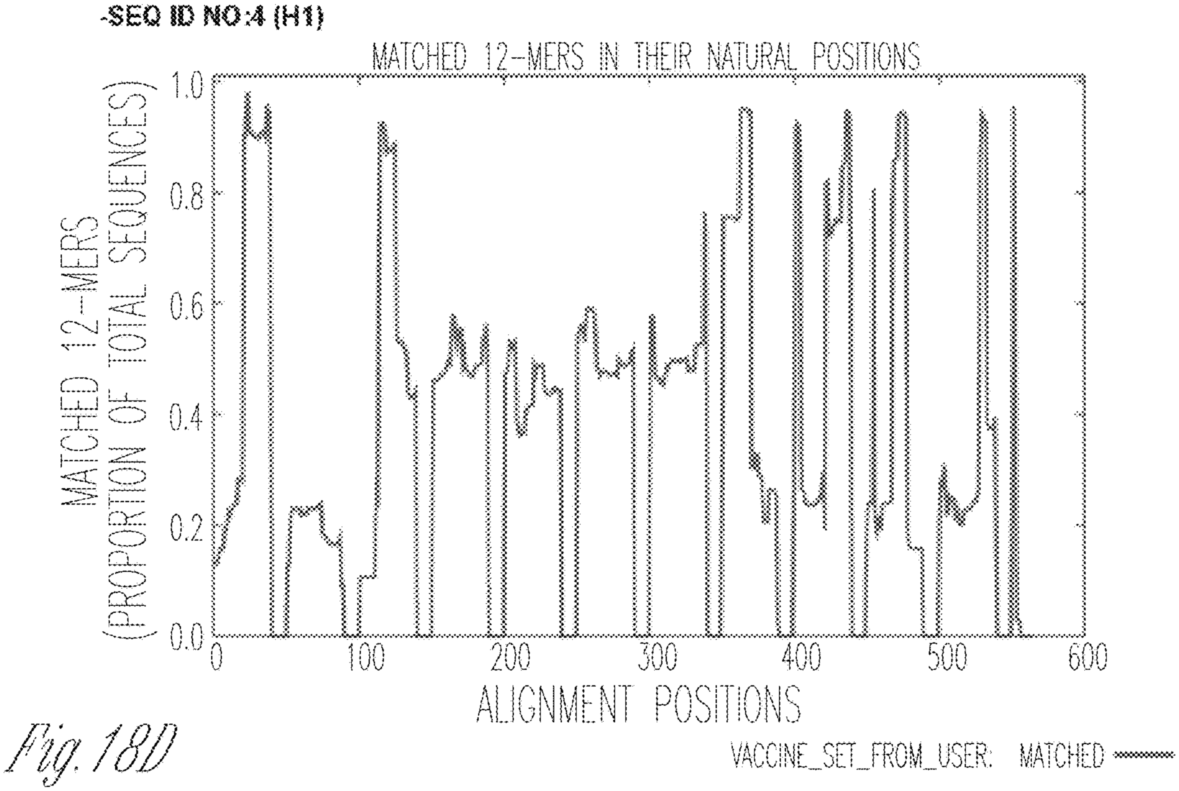
Figure 18E:
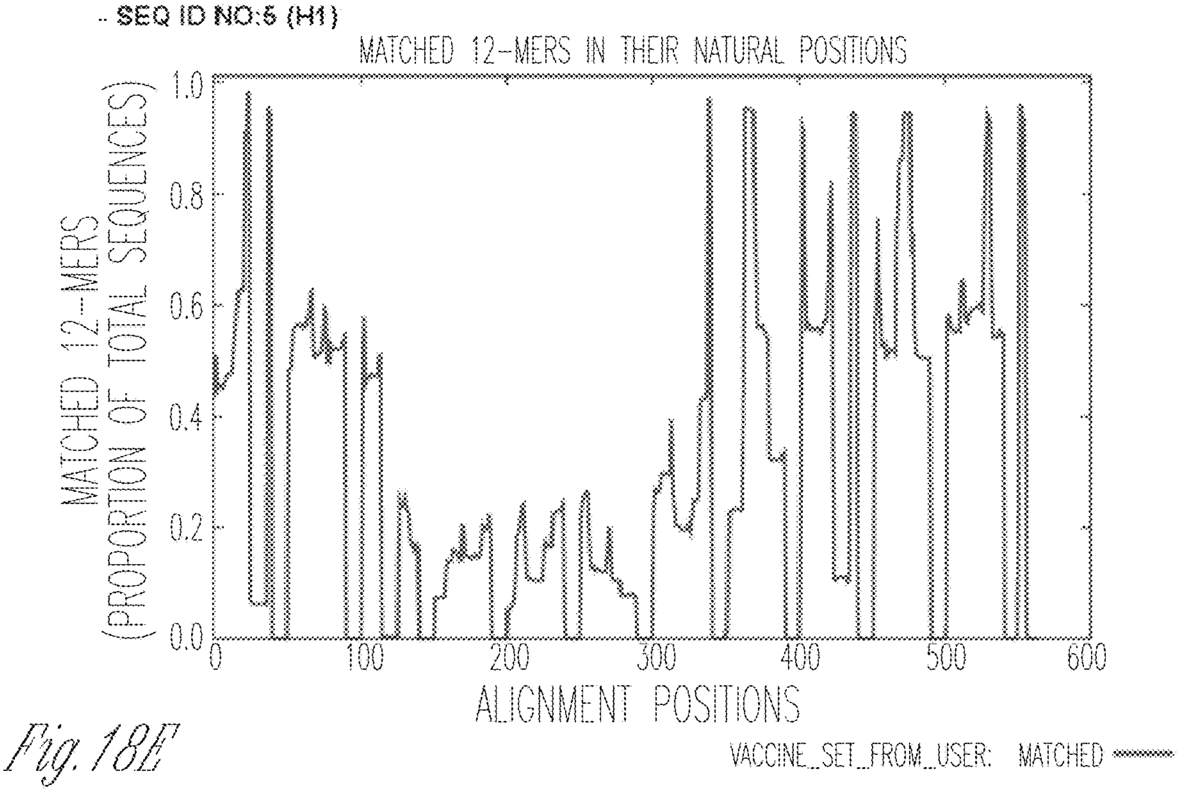
Figure 18F:
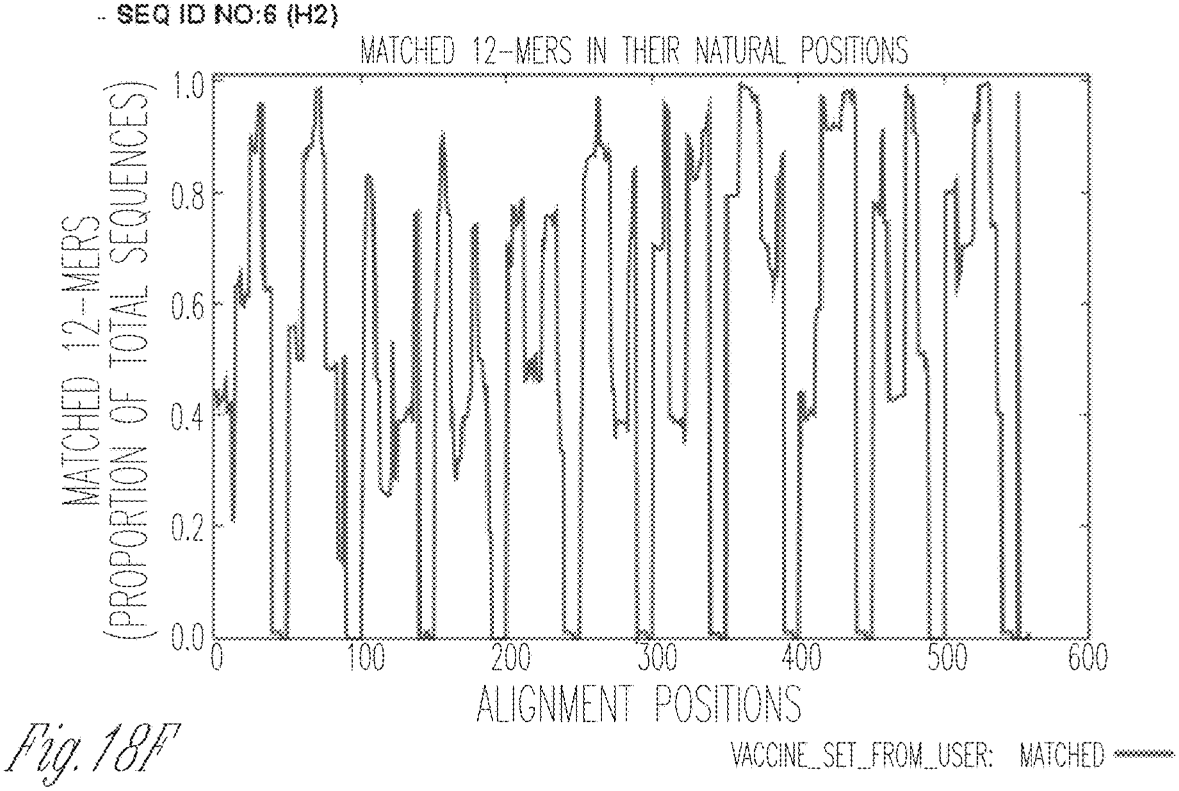
Figure 18G:
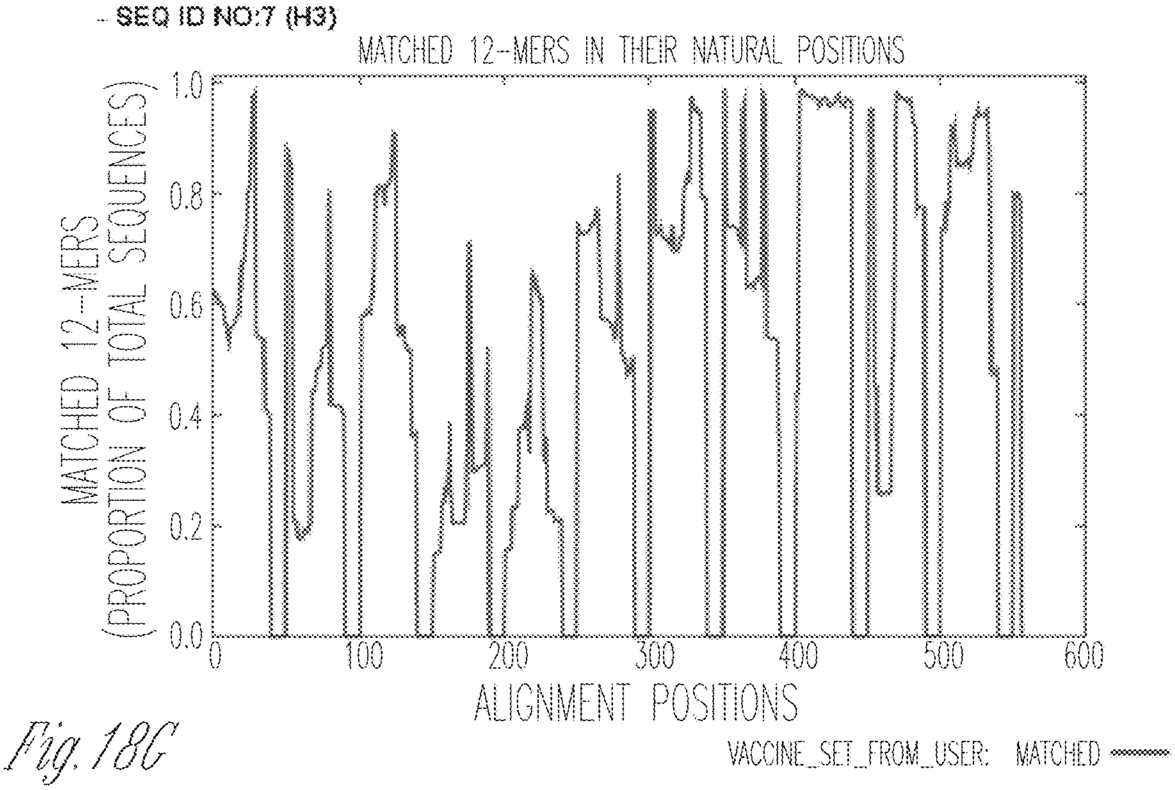
Figure 18H:
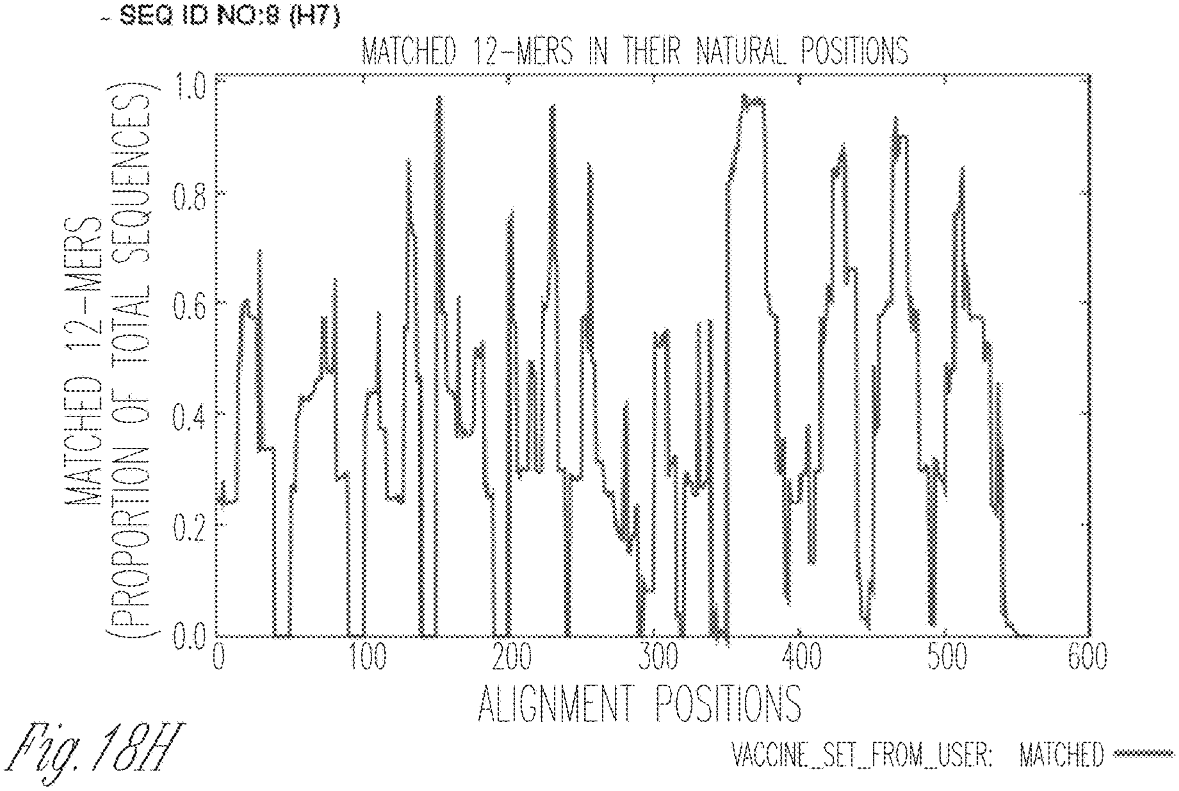
Figure 18I:
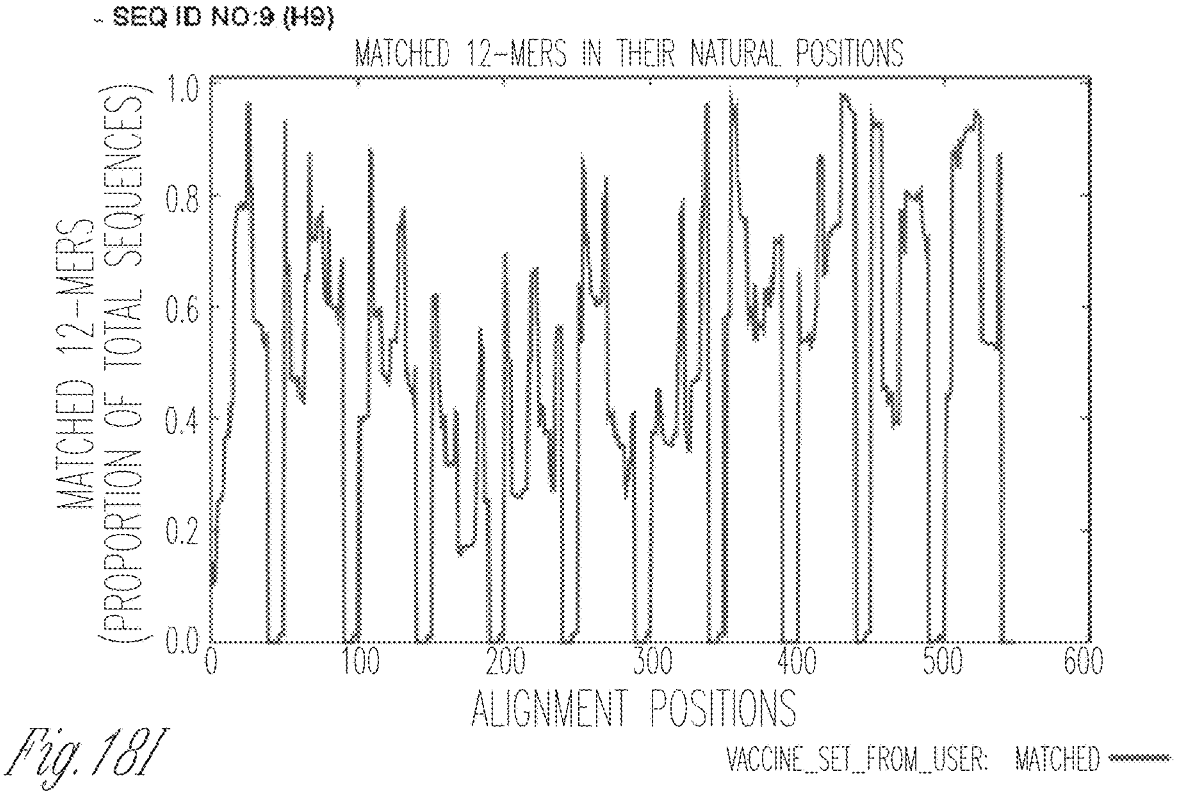
Figure 18J:
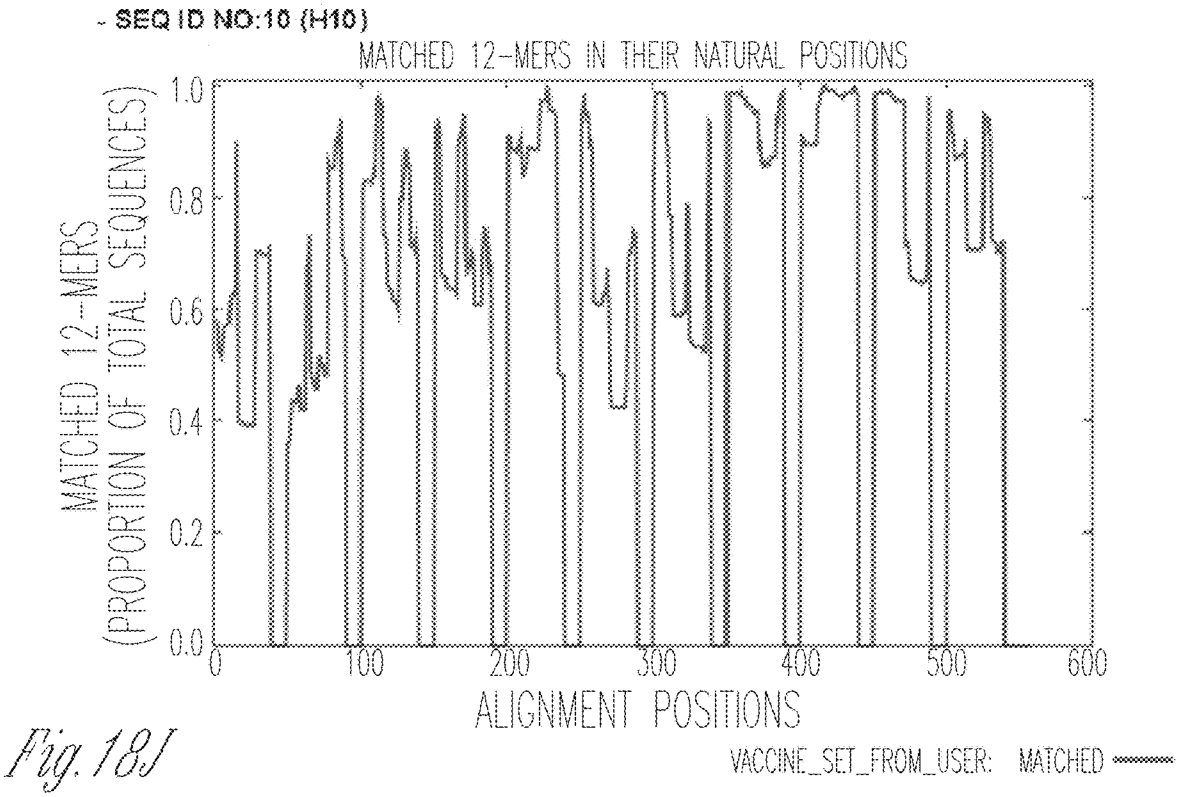
Figure 18K:
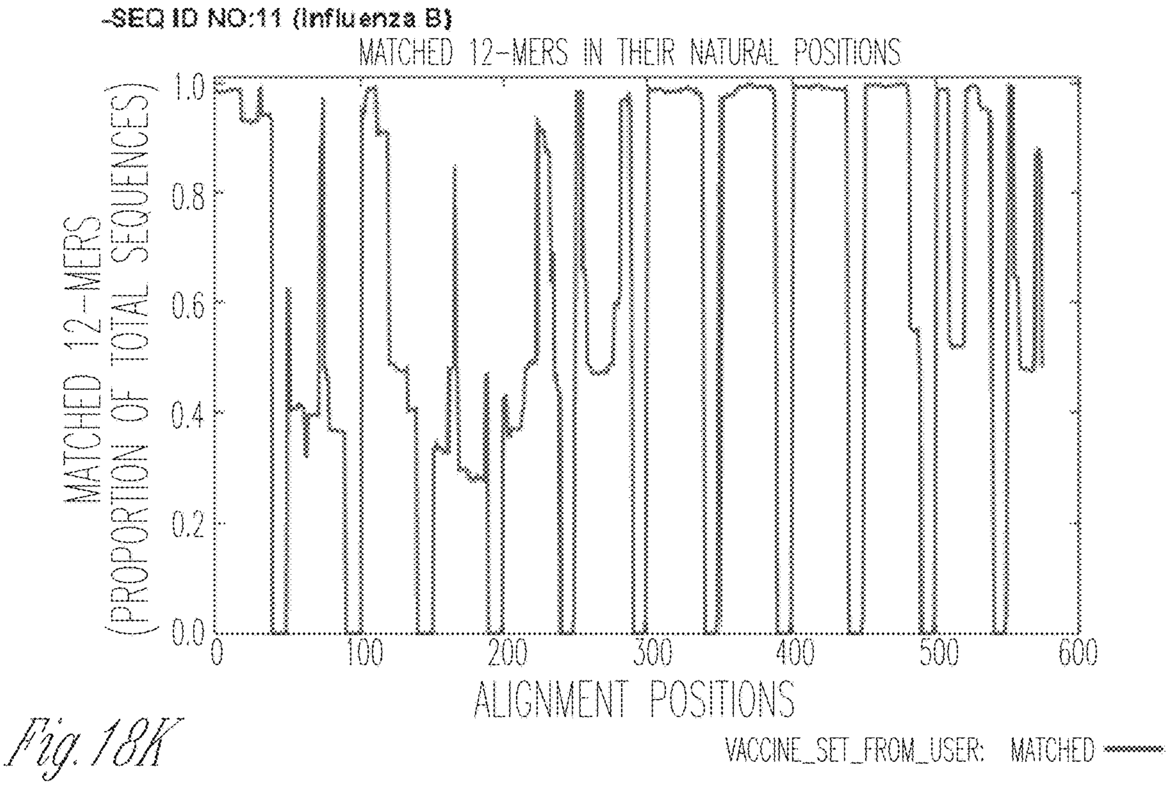
Figure 18L:
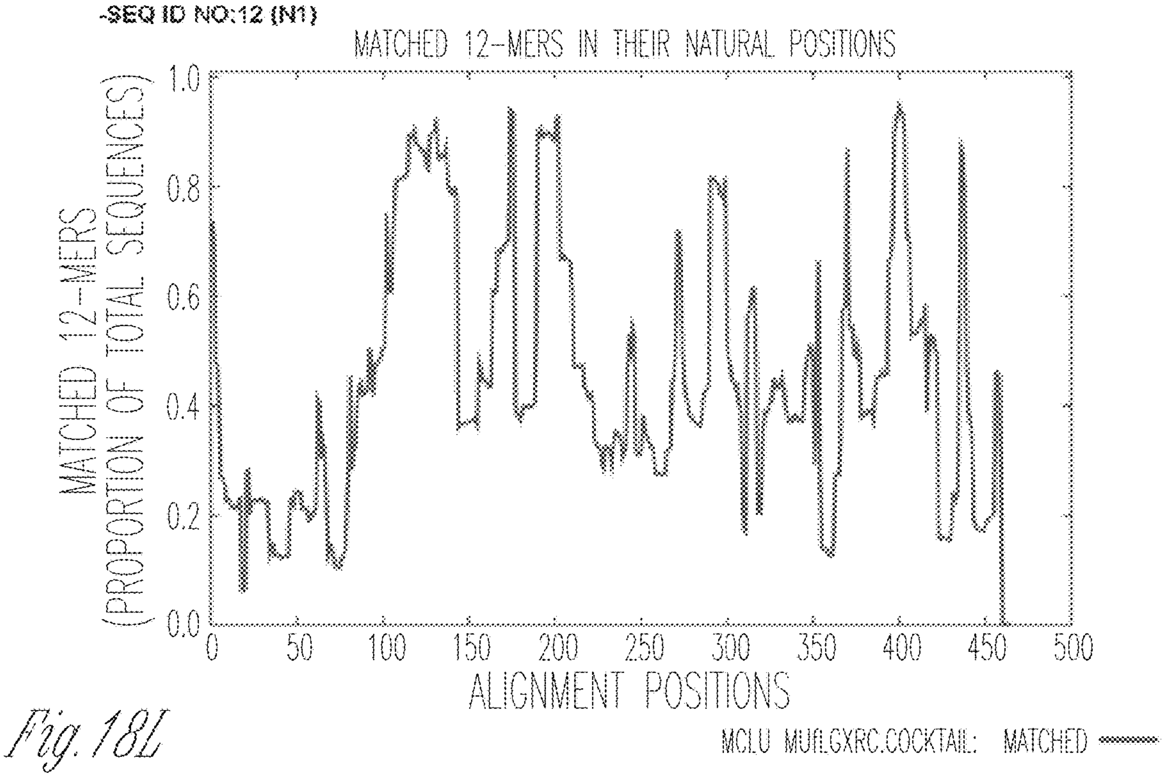
Figure 18M:
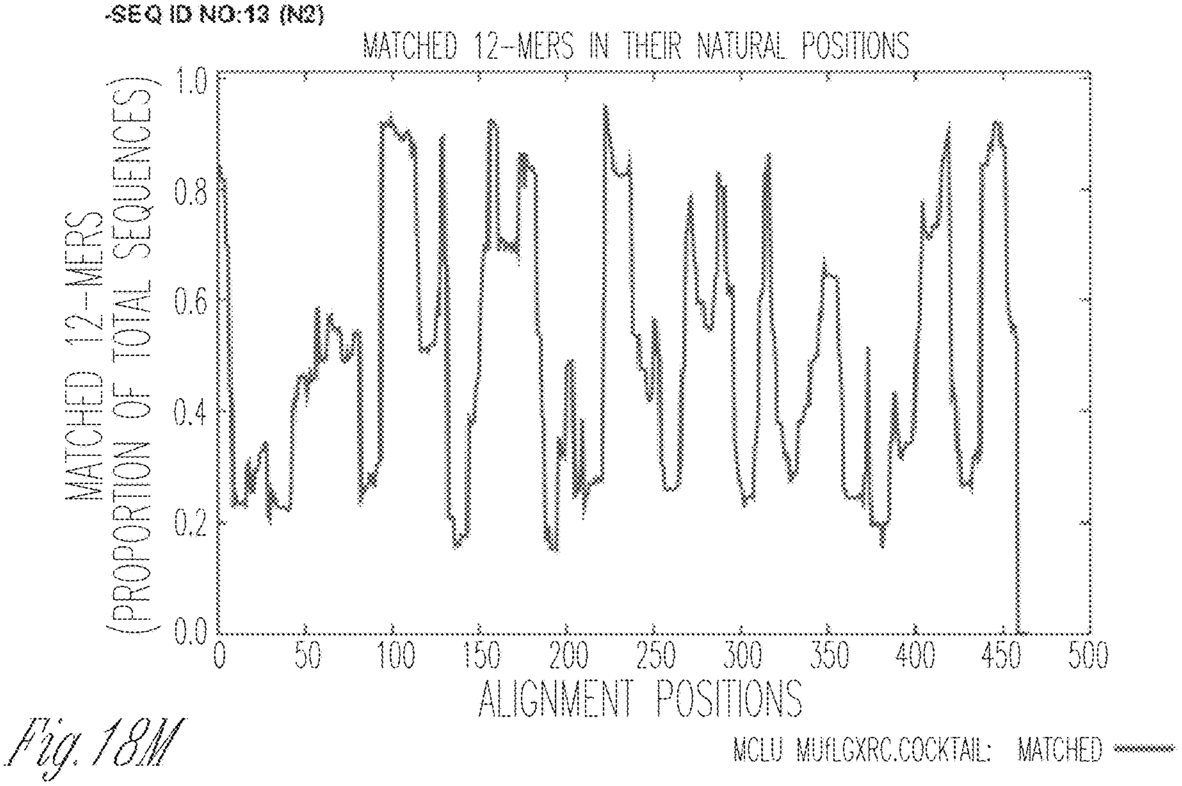
Figure 18N:
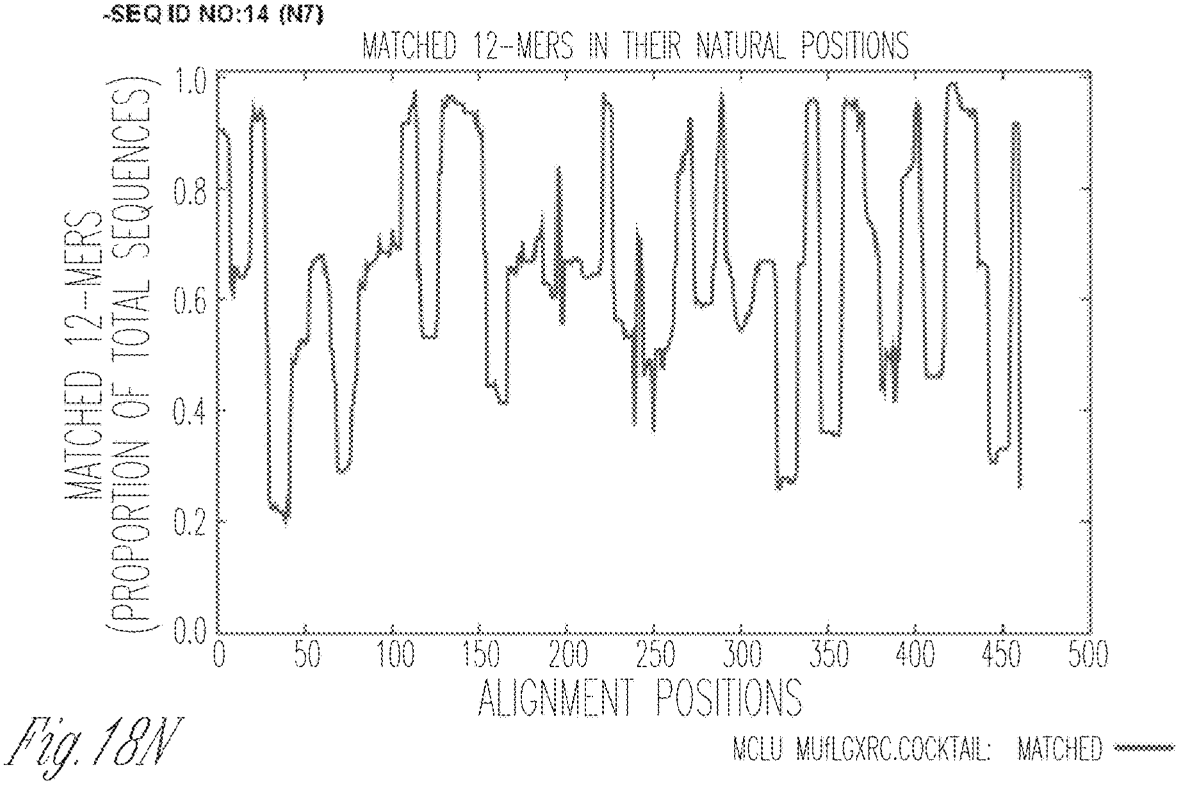

To determine whether antibodies to MVA-H5M had virus neutralizing activity, mice were intradermally inoculated with MVA-H5M, MVA-LUC, or PBS; and antibody titers from immunized mice were measured against A/VN/1203/04, A/MG/244/05, A/HK/483/97 and A/Egypt/1/08 challenge viruses. At four weeks post-immunization, MVA-H5M elicited significant neutralizing antibody (Ab) titers and protected against all four H5N1 strains (FIGS. 5B & 13A-C&G). Geometric mean titers (GMT) of Ab against A/VN/1203/04, A/MG/244/05 and A/HK/483/97 did not differ significantly. In contrast, GMT of Ab against A/Egypt/1/08 was significantly lower than for the other three H5N1 viruses. None of the MVA-LUC control injected animals survived challenge (FIGS. 13A-C and G). Notably, no virus replication was detected in the lungs of any of the MVA-H5M vaccinated mice challenged with any of the four H5N1 viruses (FIG. 13M). Furthermore, vaccination with MVA-H5M reduced lung pathology after challenge with avian influenza viruses (FIG. 16). MVA-H5M-vaccinated mice showed no to mild lung lesions compared to the MVA-LUC-vaccinated groups. Lesions included thickening of alveolar wall, lung consolidation with white blood cell infiltration, necrosis of alveolar walls and pulmonary edema. Immunohistochemistry staining revealed high quantities of viral antigen in the MVA-LUC control group (FIGS. 16D, H, L & P). In contrast, viral antigen was not detected in lungs of mice that received MVA-H5M (FIGS. 16C, J, K & O). These data demonstrate the ability of MVA-H5M to confer both broad and strong protection against multiple clades of avian influenza viruses.

Figure 5B:
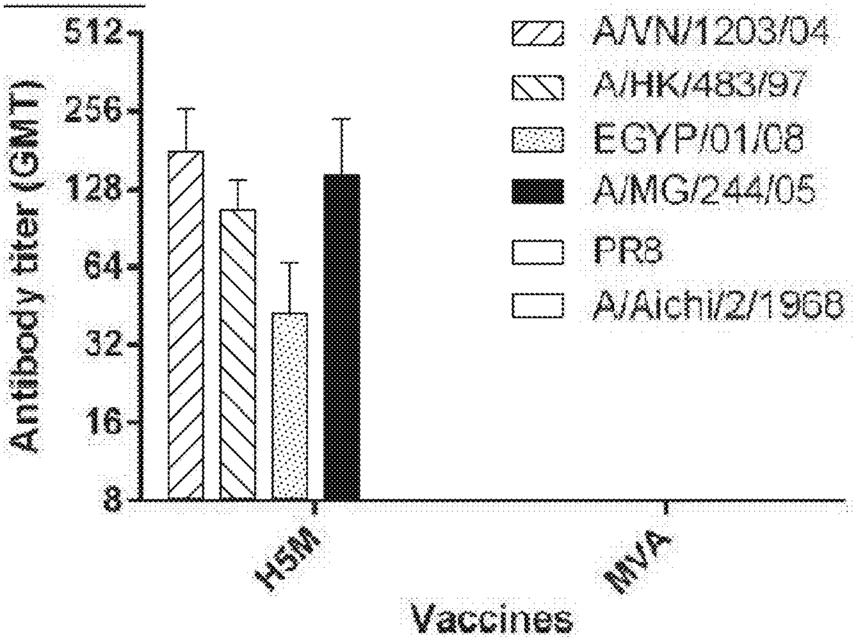
Figure 13N:
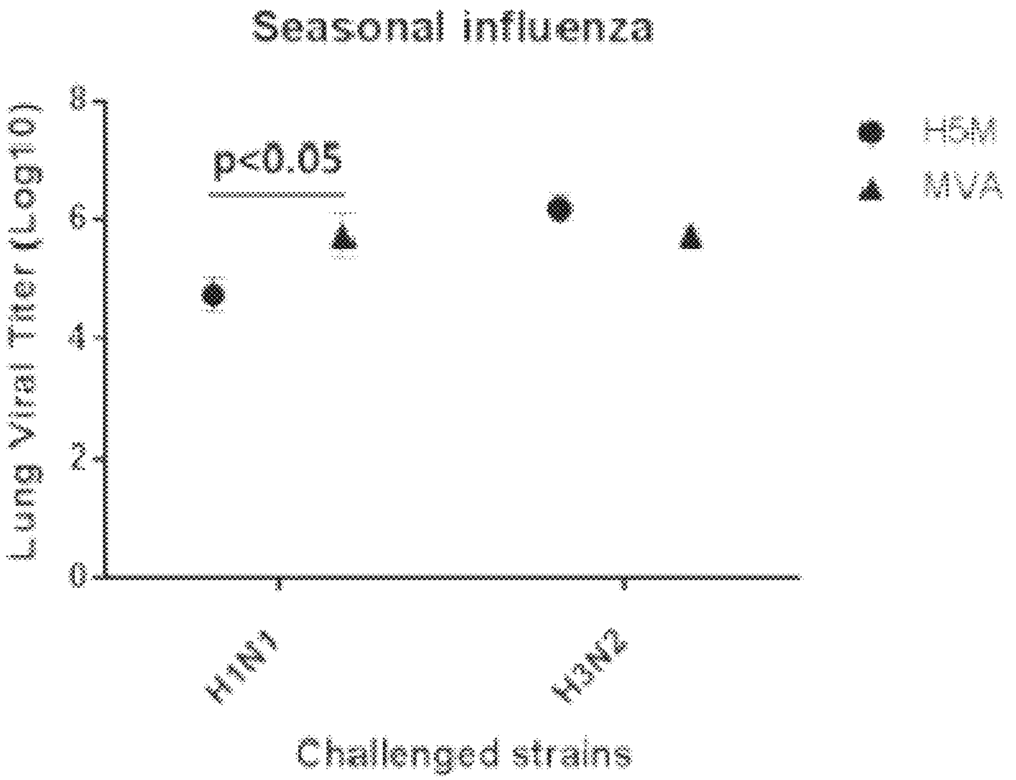

The ability of the MVA-H5M construct to protect mice against seasonal influenza viruses was also evaluated. Vaccination followed the same protocol as with H5N1 viruses, except mice were challenged with A/Puerto Rico/8/1934 (PR8; H1N1) and A/Aichi/2/1968 (H3N2). At four weeks post-vaccination, neutralizing Ab titers were below detectable levels against both seasonal influenza viruses (FIG. 5B). Despite the lack of detectable neutralizing Ab, MVA-H5M conferred complete protection against PR8 (H1N1) with no significant weight loss observed (FIGS. 13H and K). In contrast, no protection was observed against A/Aichi/2/68 (H3N2) challenge (FIGS. 13I and L). Regardless of strain, viral replication was observed in the lungs of mice vaccinated with MVA-H5M and challenged with seasonal influenza viruses; however, mice challenged with PR8 had significantly lower viral lung titers than mice vaccinated with MVA-LUC controls (FIG. 13N). In contrast, vaccination with MVA-H5M had no effect on viral replication in the lungs of mice challenged with A/Aichi/2/68 (FIG. 13N).

Short- and Long-Term Immunity

Figure 4:
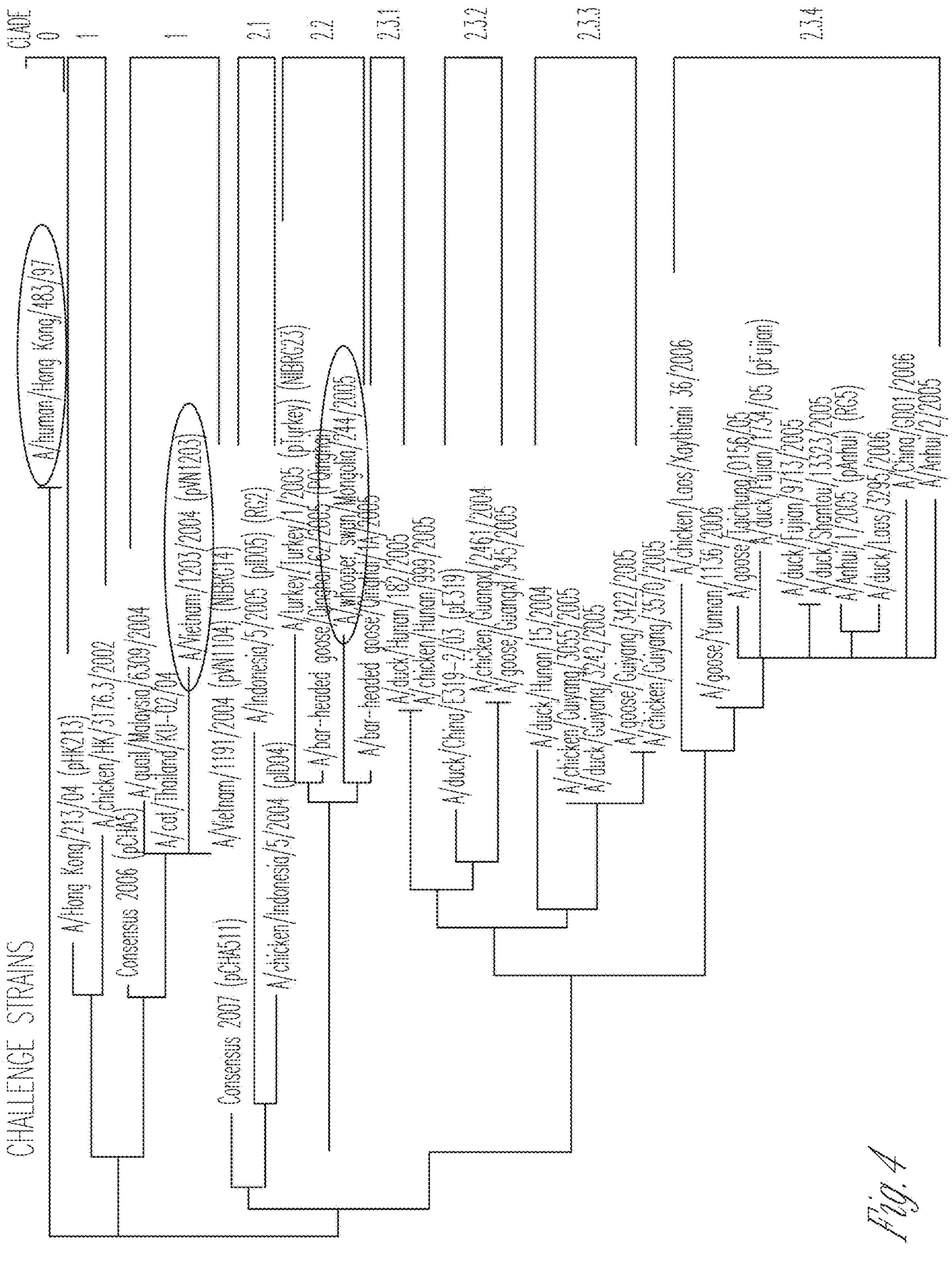
FIG. 4. Selection of divergent challenge stains.
Figure 14A:
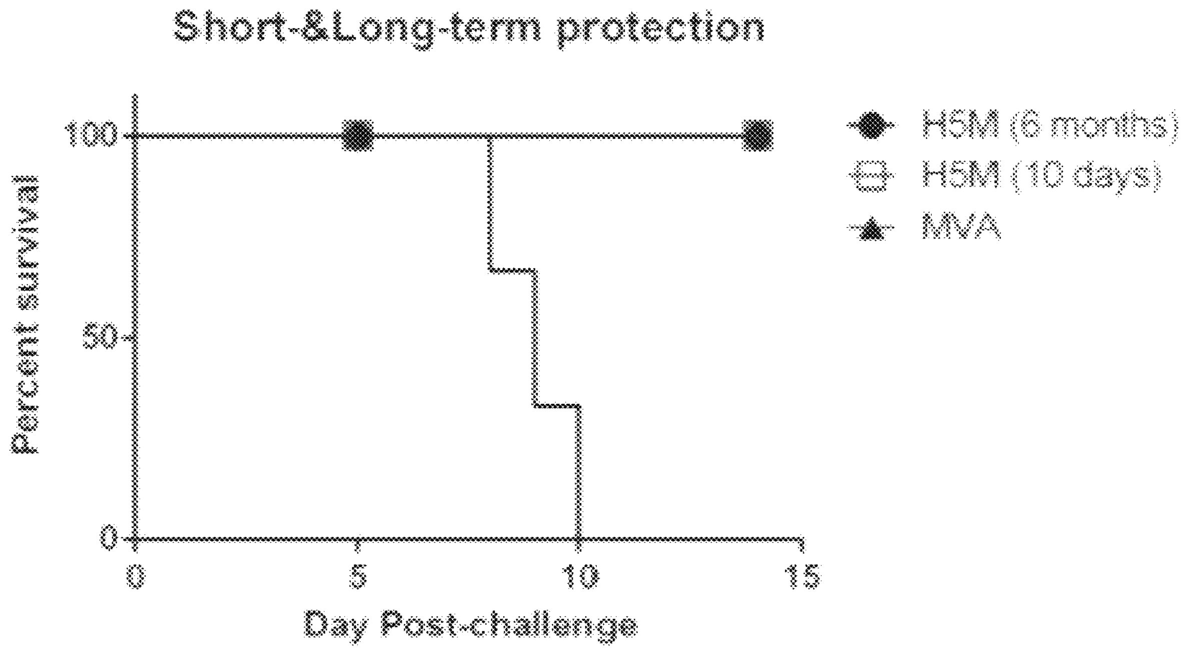
FIGS. 14A-D. MVA-H5M provides short- and long-term immunities. (A-B) BALB/c mice were immunized with single dose MVA-H5M or MVA-LUC. 10 days or 6 months post-vaccination, mice were challenged with a lethal dose of influenza A/HK/483/97. (C) Neutralization titers from vaccinated mice at 10 days and 6 months post-vaccination. (D) CD4+ and CD8+ T cells responses at 5 months post-vaccination.
Figure 14B:
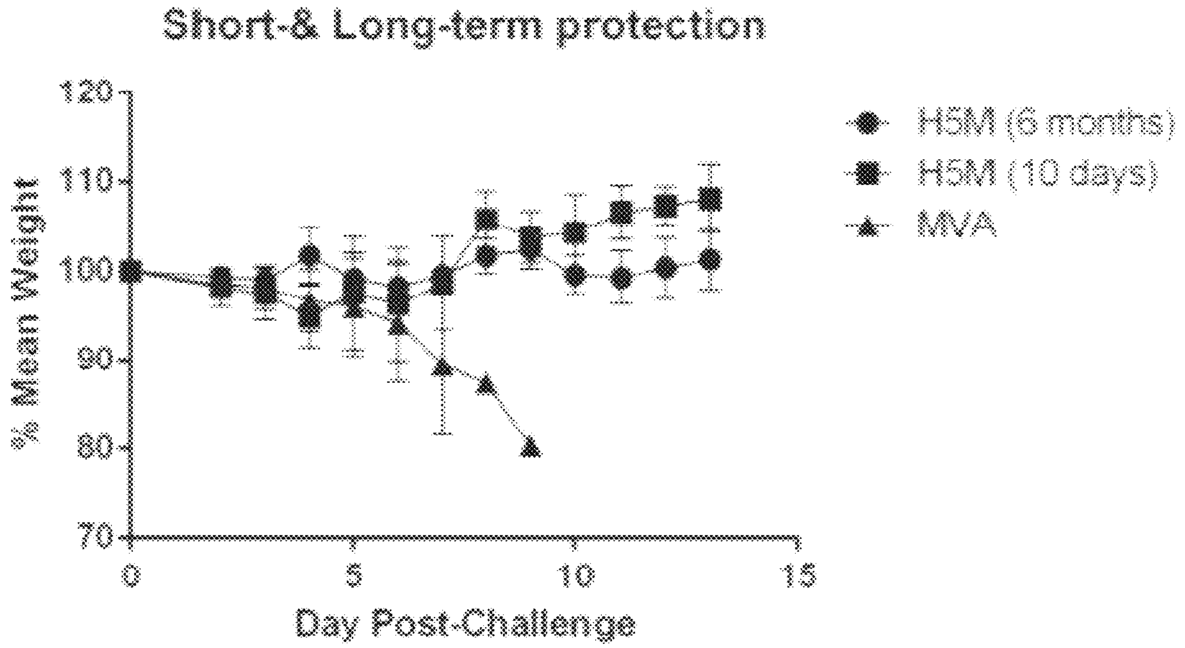
Figure 14C:
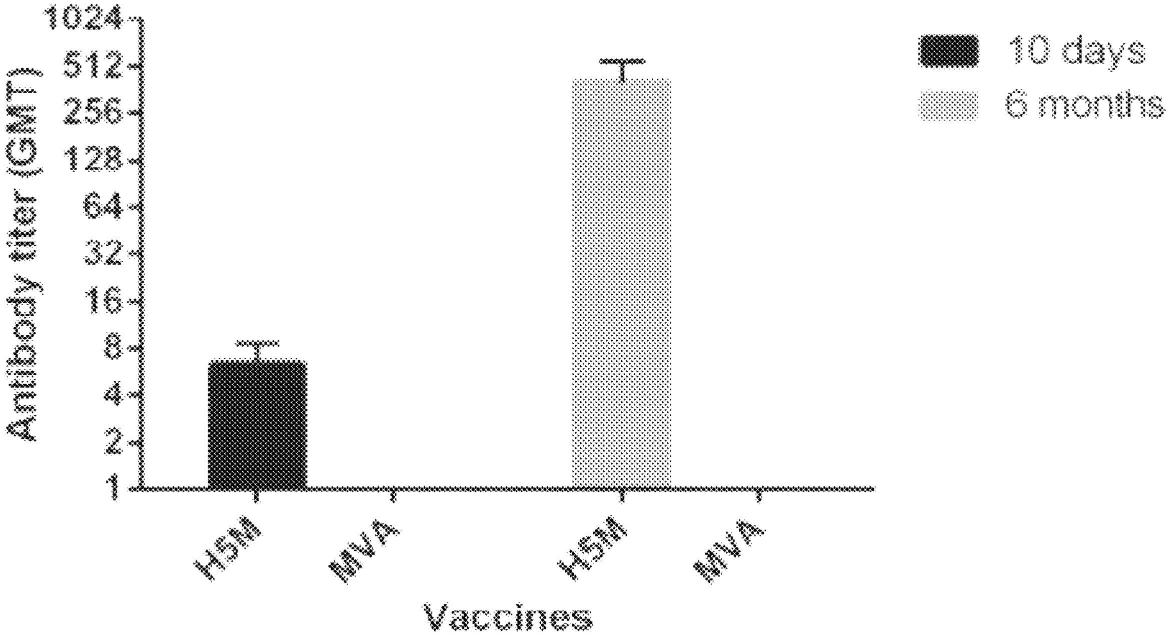
Figure 14D:
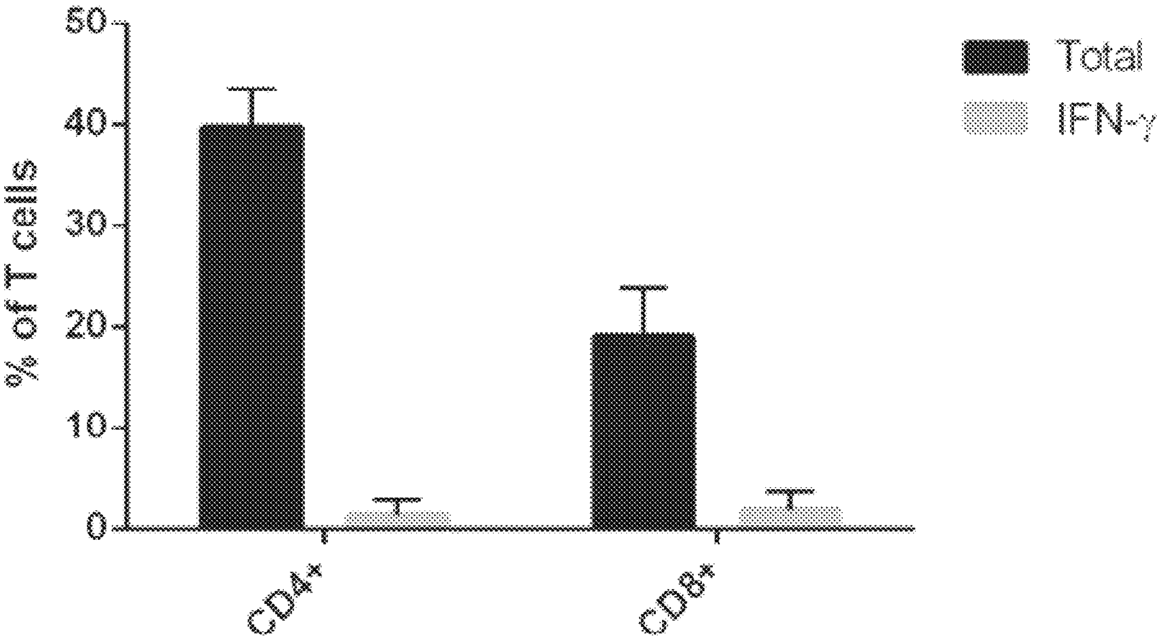
Figure 15A:
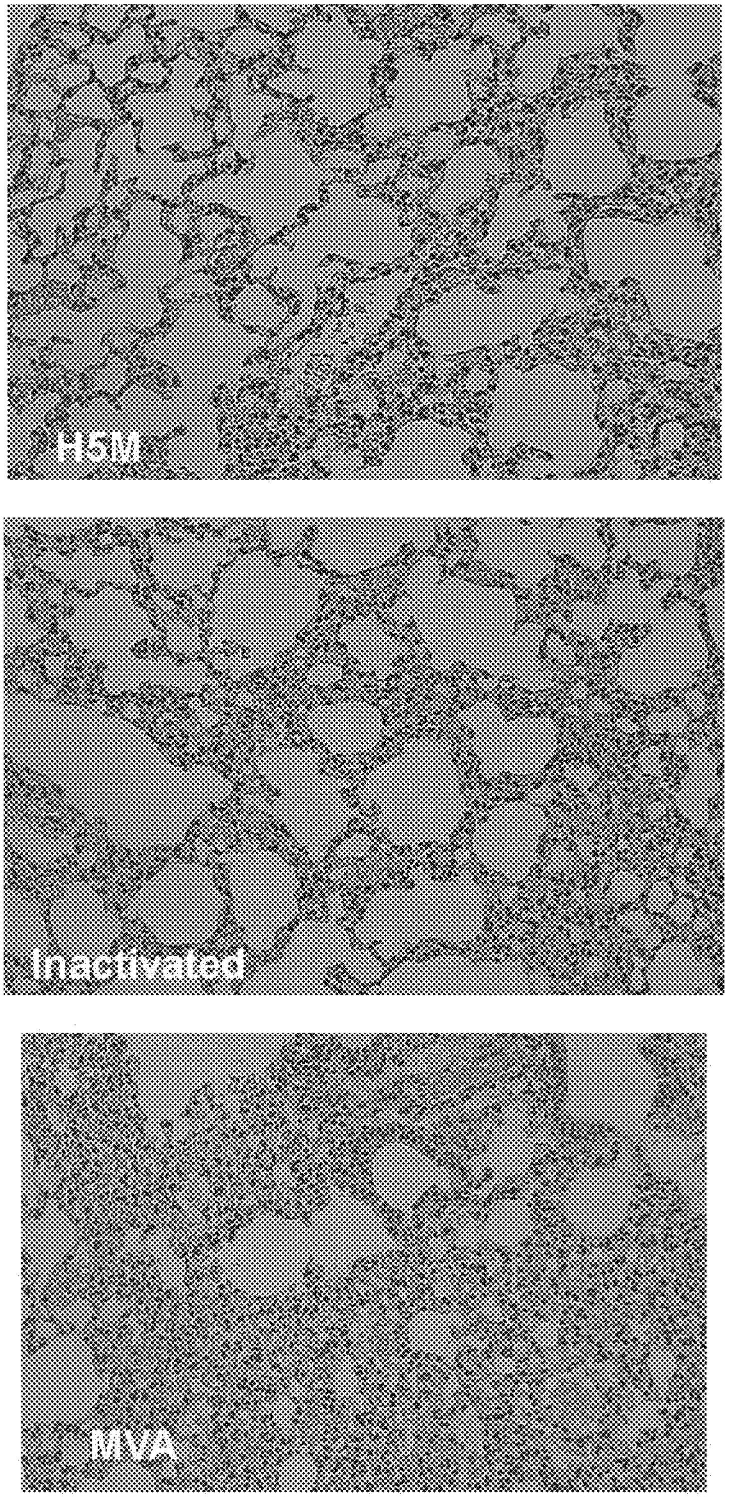
FIGS. 15A-C. Histopathology in mice immunized with H5M, inactivated virus or vector (MVA) alone and challenged with VN/1203/04 (A); MONG/244/05(B); and HK/483/97 (C).
Figure 15B:
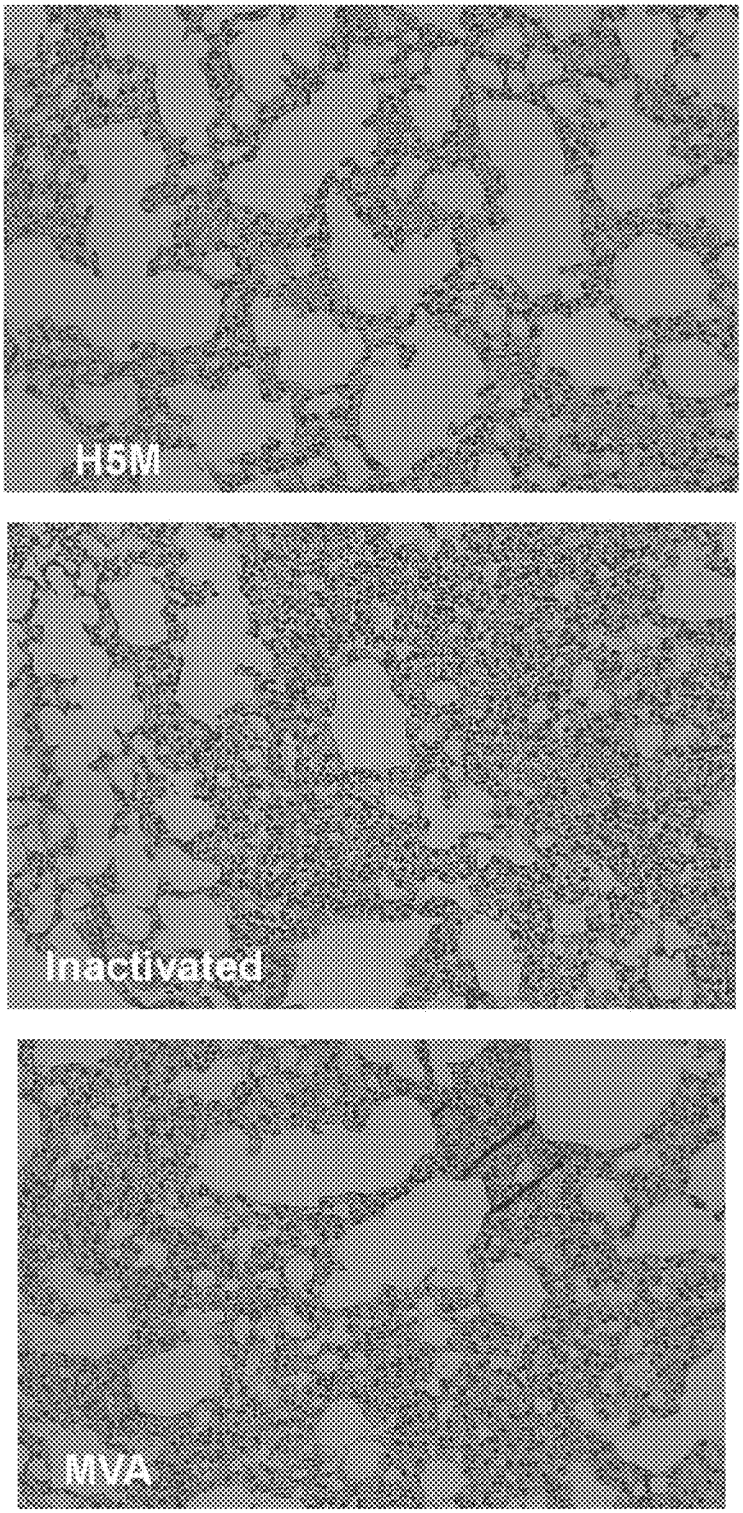
Figure 15C:
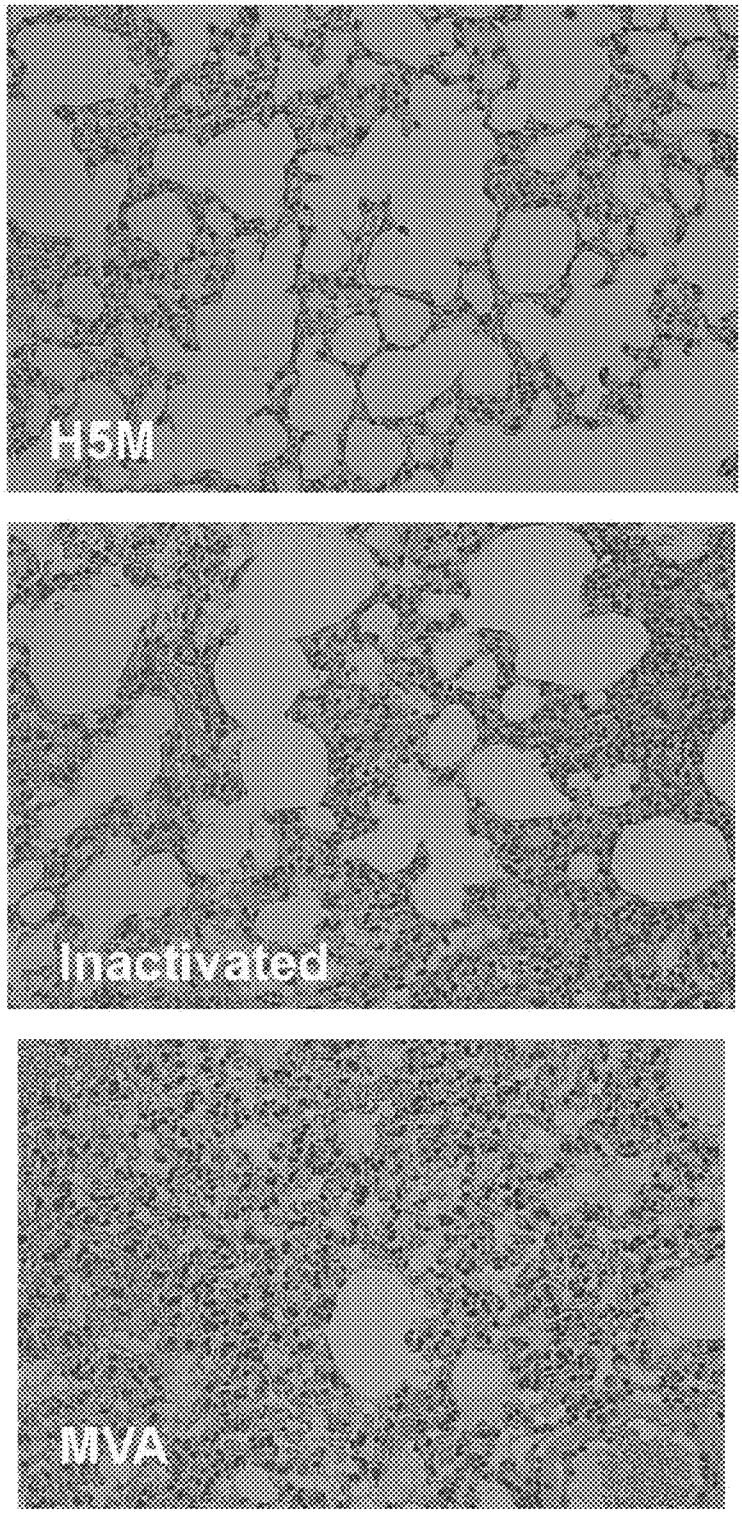

To assess the ability of the MVA-H5M construct to confer both short- and long-term immunity, groups of mice vaccinated with a single dose MVA-H5M were challenged at either 10 days or 6 months. MVA-H5M provided full protection against a lethal dose of A/HK/483/97, at both 10 days and 6 months post-vaccination (FIGS. 14A and B). Additionally, neutralizing antibodies against A/HK/483/97 were detected at both 10 days and 6 months post-vaccination (FIG. 14C). Microneutralization assays were conducted using A/HK/483/97 because it is the most virulent strain among the four H5N1 strains used in the present study. Surprisingly, GMT Ab titers at 6 months were substantially higher than those detected at 4 weeks post-vaccination (FIGS. 15B & 4C). In these animals, H5N1-specific IFN-γ $CD4^+$ and $CD8^+$ T cell responses were detected using flow cytometry. IFN-γ-releasing $CD4^+$ and $CD8^+$ T cells were found in MVA-H5M vaccinated mice 5 months after dosing (2 weeks before challenged in long-term protection study), indicating a long-term memory response (FIG. 14D).

Discussion

The rapid evolution of influenza viruses poses global health challenges necessitating development of vaccines with broad cross-protective immunity. Herein, the development of a broadly protective vaccine, MVA-H5M, based on a mosaic epitope approach, is described. The mosaic approach minimizes genetic differences between selected vaccine antigenic sequences and circulating influenza strains while maximizing the overall breadth of cross-protective immune responses. The present results demonstrated that a single dose of MVA expressing a mosaic H5 hemaglutinin (MVA-H5M) provided broad protection against multiple H5N1 viruses, including the highly pathogenic Egyptian strains, and also an H1 subtype virus (PR8). The MVA-H5M vaccine provided robust and prolonged protection against a lethal dose of highly pathogenic avian influenza as early as 10 days and as long as 6 months post vaccination.

In the past few years, commercially available vaccines have failed to induce the expected level of protection against the currently circulating clade 2.2.1 in Egypt (Bahgat et al., 2009; Hafez et al., 2010). It is very important that an H5N1 influenza vaccine provide broad cross-clade protection against these 2.2.1 viruses particularly the A/Egypt/1/08 strain, because this strain possess one of the four mutations that are necessary to sustain human to human transmission (Herft et al., 2012). The MVA-H5M vaccine showed complete protection against this H5N1 strain in mice. The ability to provide complete protection against H5N1 viruses with a single dose is also important for implementation; societal acceptance of a single dose vaccine would likely be higher than for a multi-dose vaccine, especially during a pandemic.

Figure 6:
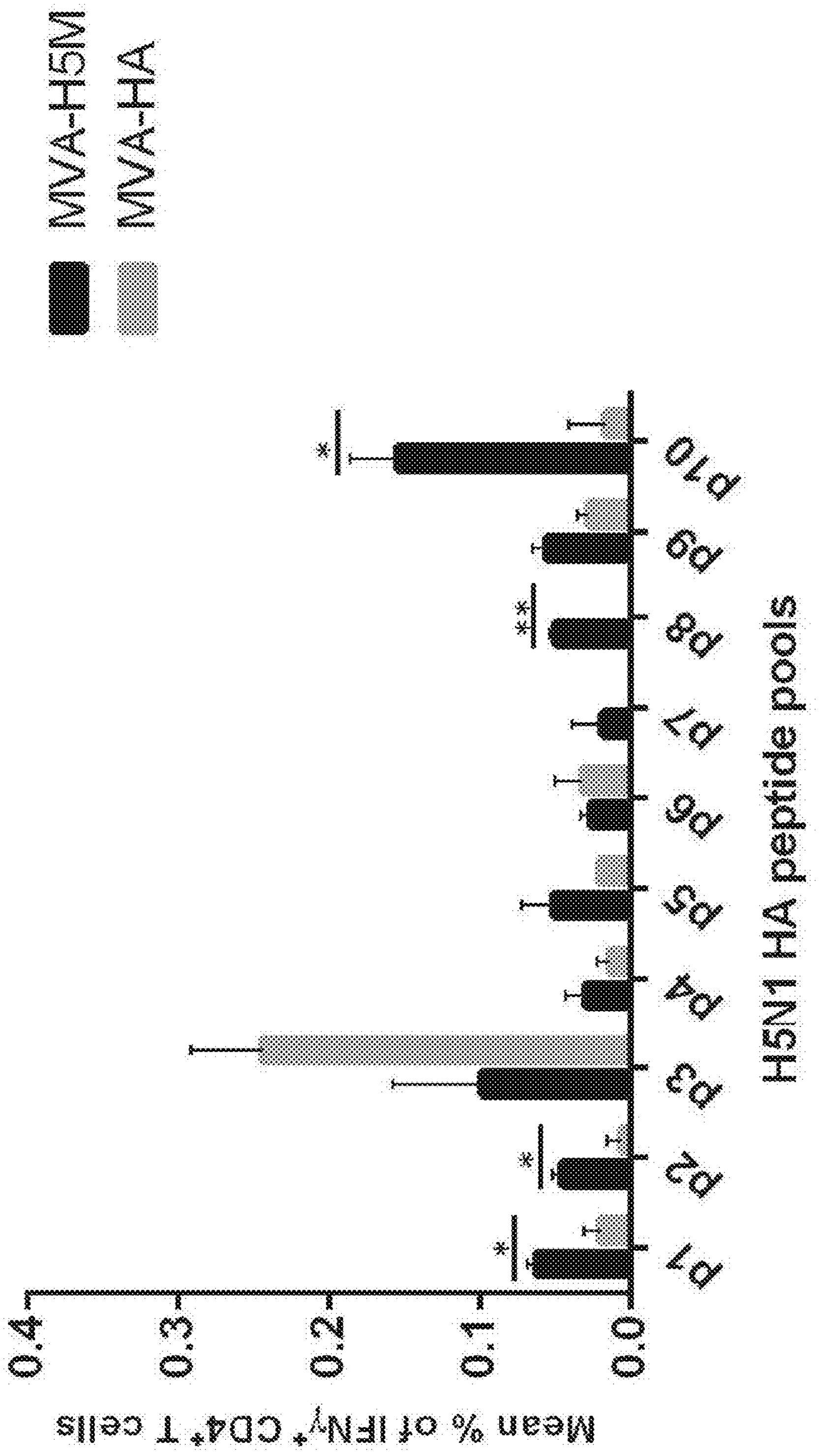
FIG. 6. MVA-H5M elicits broader epitope coverage than wild type hemagglutinin based vaccine. IFN-γ-producing CD4$^+$ T cells from mice that were vaccinated with MVA-H5M or MVA-HA. Splenocytes from vaccinated mice were collected and stimulated with HA peptide pools from H5N1 viruses (as indicated with p1-p11). *P<0.05 or **P<0.01, Student's T test.
Figure 8:
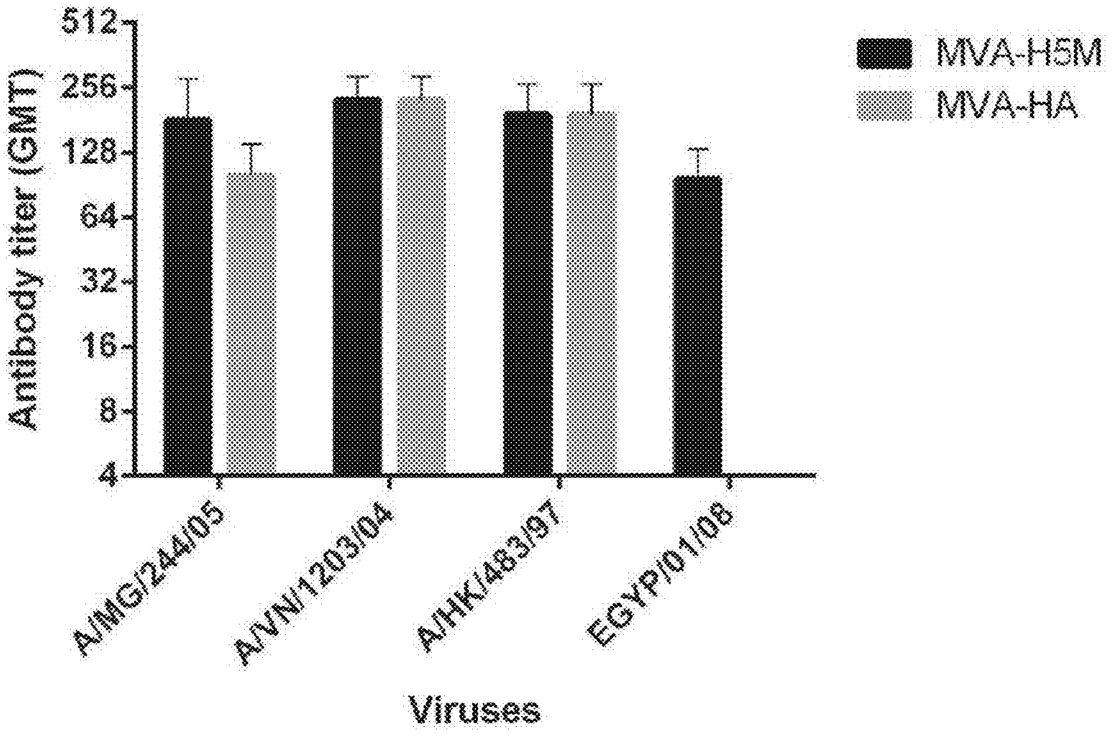
FIG. 8. Neutralization titers comparison between MVA-H5M and MVA-HA vaccines against H5N1 viruses.
Figure 9:
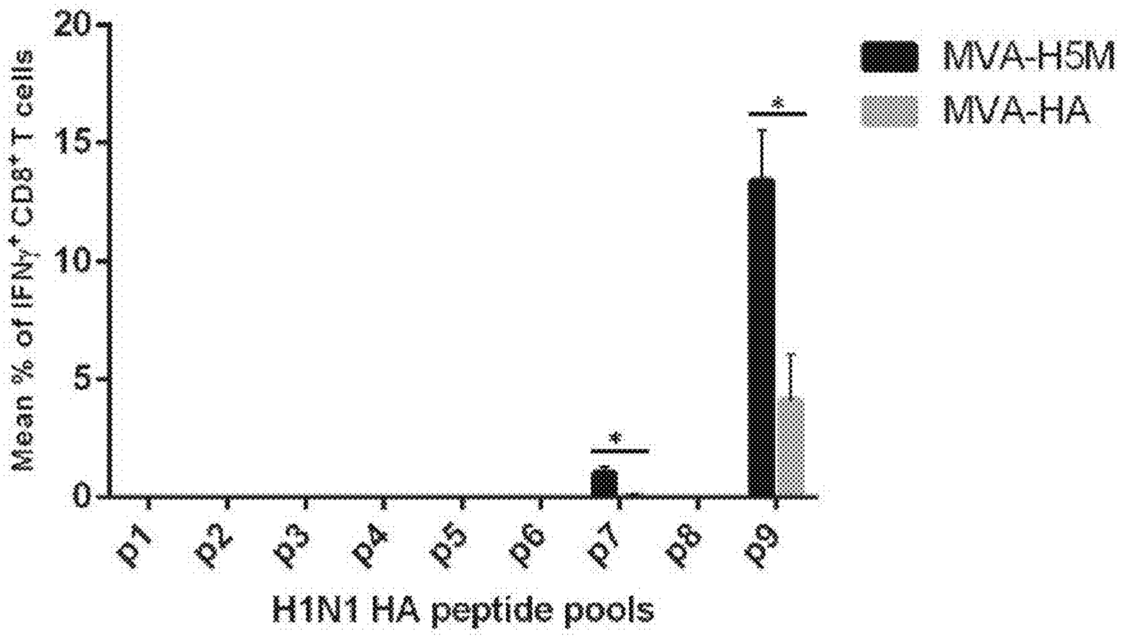
FIG. 9. MVA-H5M elicits T cells responses against PR8 HA peptides. IFN-γ-producing CD8$^+$ T cells from mice that were vaccinated with MVA-H5M or MVA-HA vaccine. Splenocytes from vaccinated mice were collected and stimulated with HA peptide pools from H1N1 viruses (as indicated with p1-p9). *P<0.05, Student's T test.

Several plausible hypotheses exist for the exact mechanism by which the mosaic vaccine confers broad protection against influenza virus challenge. One possible explanation is that the 12-mer mosaic sequence captured more T-helper epitopes, in which case the broad protective ability of MVA-H5M likely results from greater epitope coverage for the mosaic than for previous approaches (Santra et al., 2010 and FIG. 6). This could translate to a higher level of $CD4^+$ T cells and broader antibody responses than induced by wild-type sequence (MVA-HA). This hypothesis is supported by the fact that MVA-H5M showed broader IFNγ-$CD4^+$ T cell epitope coverage and broader cross-clade neutralizing antibody responses (FIGS. 8 and 9). However, other immunological aspects of the MVA-H5M vaccine still need to be further characterized. For example, data on $CD8^+$ T cell responses, cytokine profiles, antibody epitope coverage and mapping would all be necessary to fully understand the mechanism responsible for protection.

A second mechanism that may explain the breadth of protection conferred by the MVA-H5M vaccine is that the mosaic approach maintains intact antigenic structure and presumably physiological function (Santra et al., 2010; Kaur et al., 2011). It has been previously reported that most universal neutralizing antibodies are elicited by peptides in the stalk regions (Kaminski et al., 2011; Kaur et al., 2011). The MVA-H5M vaccine has normal hemagglutination function and also is expressed as a cleavable protein. Furthermore, the mosaic H5 might provide higher accessibility to the stalk region and stimulate a more robust neutralizing antibody response against epitopes in the stalk region. Crystallography of expressed mosaic H5 would likely be required to reveal the actual structure of this protein and compare it to the known structure of H5 hemagglutinin.

The MVA-H5M provided sterilizing lung protection with no mortality and no morbidity against H5N1 viruses (FIG. 13). Moreover, no viral antigens were detected in the lung after challenge (FIG. 14). These results are likely due to high neutralizing antibodies (at least 1:32 end-point titer) (FIG. 5). Previous reports have demonstrated that a minimum neutralizing antibody concentration of 1:16 end-point titer is sufficient to provide complete protection against H5N1 viruses (Howard et al., 2011). Although antibody mediated protection is suggested to be the main contributor of protection in the present vaccine, T cells may also play a role.

It is currently unclear whether the use of a live viral vector such as MVA contributed to the increased cross-protection described herein. It is possible that H5M expression by MVA induced high levels of cross reactive neutralizing antibodies as well as HA-specific IFN-γ-secreting $CD4^+$ and $CD8^+$ T cells. Specific $CD4^+$ and $CD8^+$ T cells that were induced by MVA-H5M vaccine recognized different regions of diverse H5N1 peptides (FIG. 6), as well as recognizing specific conserved epitopes that had been previously reported (Kuwano et al., 1991). The protective efficacy of the H5M antigen as a recombinant protein may require the use of adjuvants and multiple doses to achieve desired protection.

The mosaic approach has been previously used for developing vaccines against the highly variable HIV viruses, capturing potential CD8 T cell epitopes with a length of nine amino acids (Barouch et al., 2010; Fischer et al., 2007) while still maintaining normal protein structure. Because complete protection against influenza viruses is based primarily on humoral immunity (Chiu et al., 2013; Niqueux et al., 2010), the algorithm for epitopes of 12 amino acids was modified in order to capture potential T helper cell epitopes (Gogolak et al., 2000; Ben-Yedidia and Arnon, 2005) in order to target antibody producing plasma cell via T helper cells activation. This strategy may have facilitated MVA-H5M achieving high neutralizing antibody with single dose (FIG. 5).

The vaccine elicited strong humoral responses against multiple H5N1 viruses but no cross-neutralizing antibodies against seasonal influenza viruses (H1N1 and H3N2). Despite the lack of neutralizing antibodies against H1N1 PR8 virus, the MVA-H5M vaccine provided 100% protection against PR8. This suggests a substantial role of cellular immune responses against PR8 virus, as shown in FIG. 9, likely because the H5M protein possesses some CLT epitopes of PR8 (Bui et al., 2007). This protection can also be explained by the genetic relationship between the H5 and H1 hemagglutinin subtypes, as both belong to group 1 (Liu et al., 2009), and it elicits high amount of cross non-neutralizing antibody which then target and destroy H1N1 virus via antibody-dependent cellular cytotoxicity (ADCC) mechanism (Jegaskanda et al., 2013). However, the MVA-H5M vaccine did not protect immunized mice against influenza A/Aichi/2/68, which likely is due to antigenic differences as the H3 belongs to group 2 hemagglutinin. Because the MVA vector can be designed to contain multiple inserts, future constructs will contain mosaics from several hemagglutinin groups, including important seasonal (e.g H3s) and emerging (e.g., H7s) pathogens. Since this vaccine provides broad protection and a long duration of immunity, utilizing an MVA vector expressing seasonal mosaics might diminish the need for annual vaccination.

The ability of MVA-H5M vaccine to confer broad protective immunity against various homologous strains as well as heterosubtypic strains makes the mosaic approach a very promising strategy to combat the antigenic diversity of influenza viruses. Taken together with codon optimization of HA for high level of protein expression and using MVA vector as a backbone for cellular immunity activation, this approach promises to increase the broad efficacy of influenza vaccines substantially. Should this and similar approaches prove effective for other viruses in other animal models, it could help reduce or eliminate the need for annual seasonal influenza vaccine "updates," as well as providing a framework for a "pandemic preparedness" vaccine.

Example II

Figure 7:
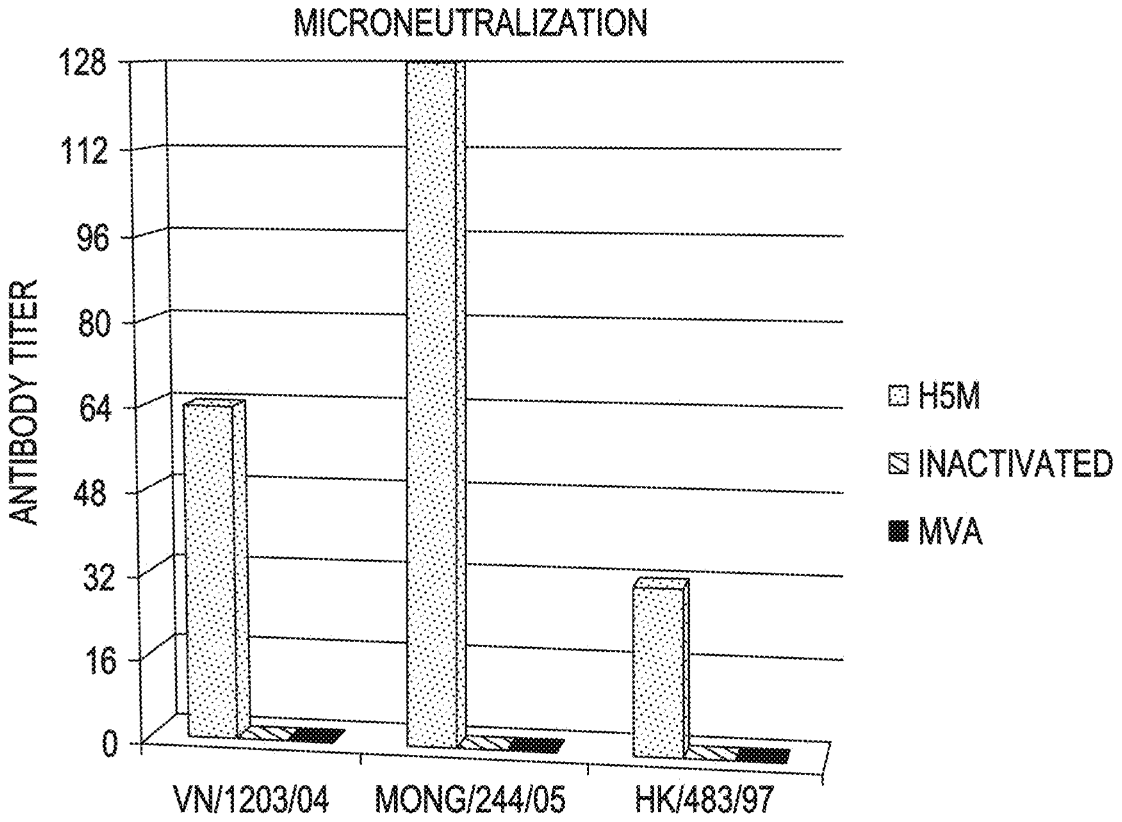
FIG. 7. Results of microneutralization assay against VN/1203/04, MONG/244/05 and Hong Kong/483/97 in mice immunized with H5M, inactivated virus or vector (MVA) alone.

Samples were collected for a microneutralization test at 4 weeks post-immunization. FIG. 7 shows the antibody titers for three different strains of influenza virus in mice immunized with H5M/MVA, inactivated vikeus (Baxter) or MVA alone. The antisera in immunized mice were reactive against three distinct viral clades (HPAI Clade 0, Clade 1, and Clade 2 viruses) after a single dose. The presence of neutralizing antibodies at 4 weeks indicates that the H5M vaccine provides rapid immunity and the immunity is higher than inactivated against the homologous virus. Even recent consensus approaches that have tried to control for the most diversity of input sequence have failed to simultaneously elicit immune responses against all of these clades.

TABLE 1

| Grp | Constructs | Route | N= | Challenge stains |
|---|---|---|---|---|
| 1 | MVA-H5M | ID | 8 | HK/483/97 |
| 2 | Inactivated H5N1 | SC | 8 | HK/483/97 |
| 3 | MVA/LUC - control | ID | 5 | HK/483/97 |
| 4 | MVA-H5M | ID | 8 | MONG/244/05 |
| 5 | Inactivated H5N1 | SC | 8 | MONG/244/05 |
| 6 | MVA/LUC - control | ID | 5 | MONG/244/05 |
| 7 | MVA-H5M | ID | 8 | VN/1203/04 |
| 8 | Inactivated H5N1 | SC | 8 | VN/1203/04 |
| 9 | MVA/LUC - control | ID | 5 | VN/1203/04 |

Figure 10A:
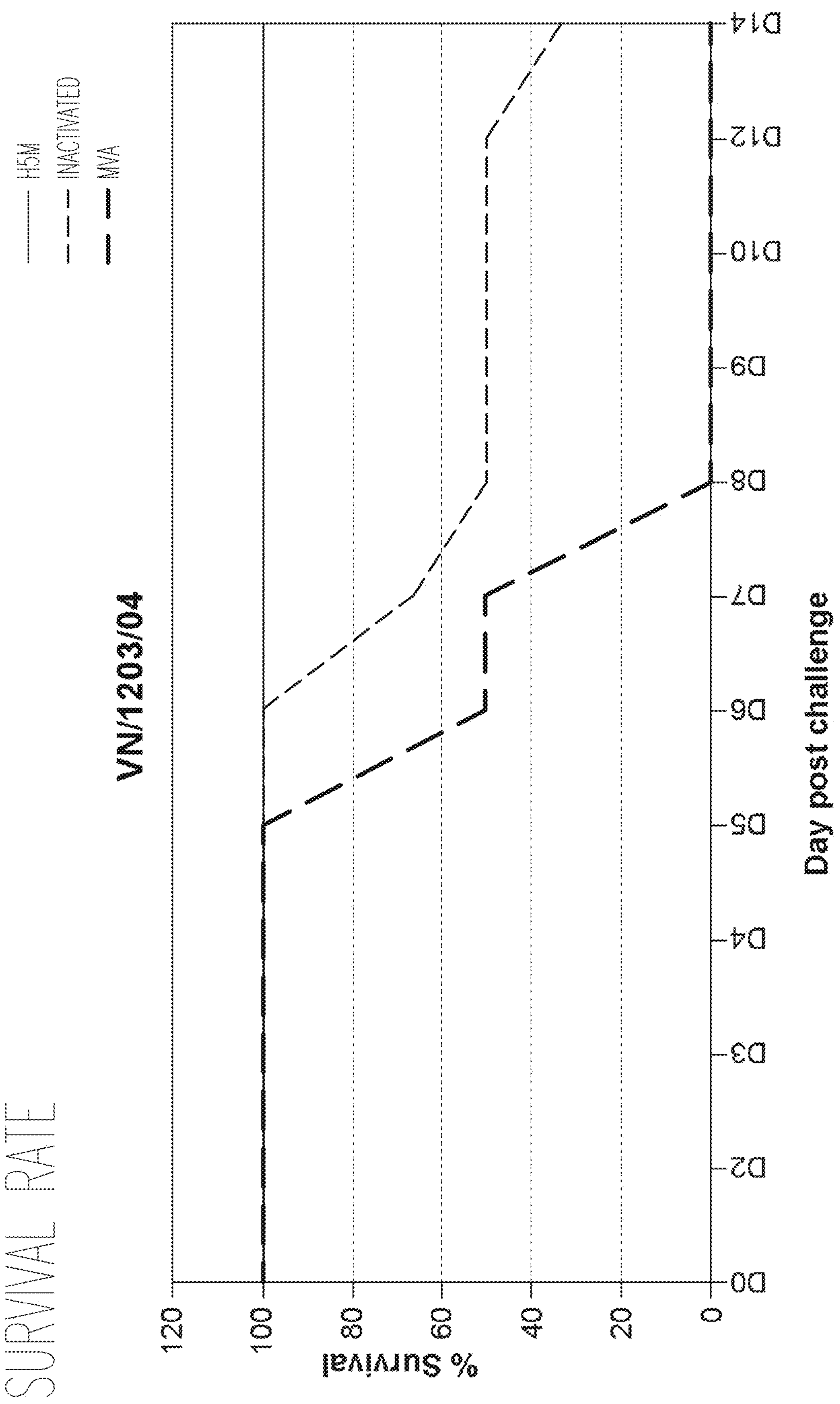
FIGS. 10A-C. Survival over time in mice immunized with H5M, inactivated virus or vector (MVA) alone and challenged with VN/1203/04 (A); MONG/244/05(B); and HK/483/97 (C).
Figure 10B:
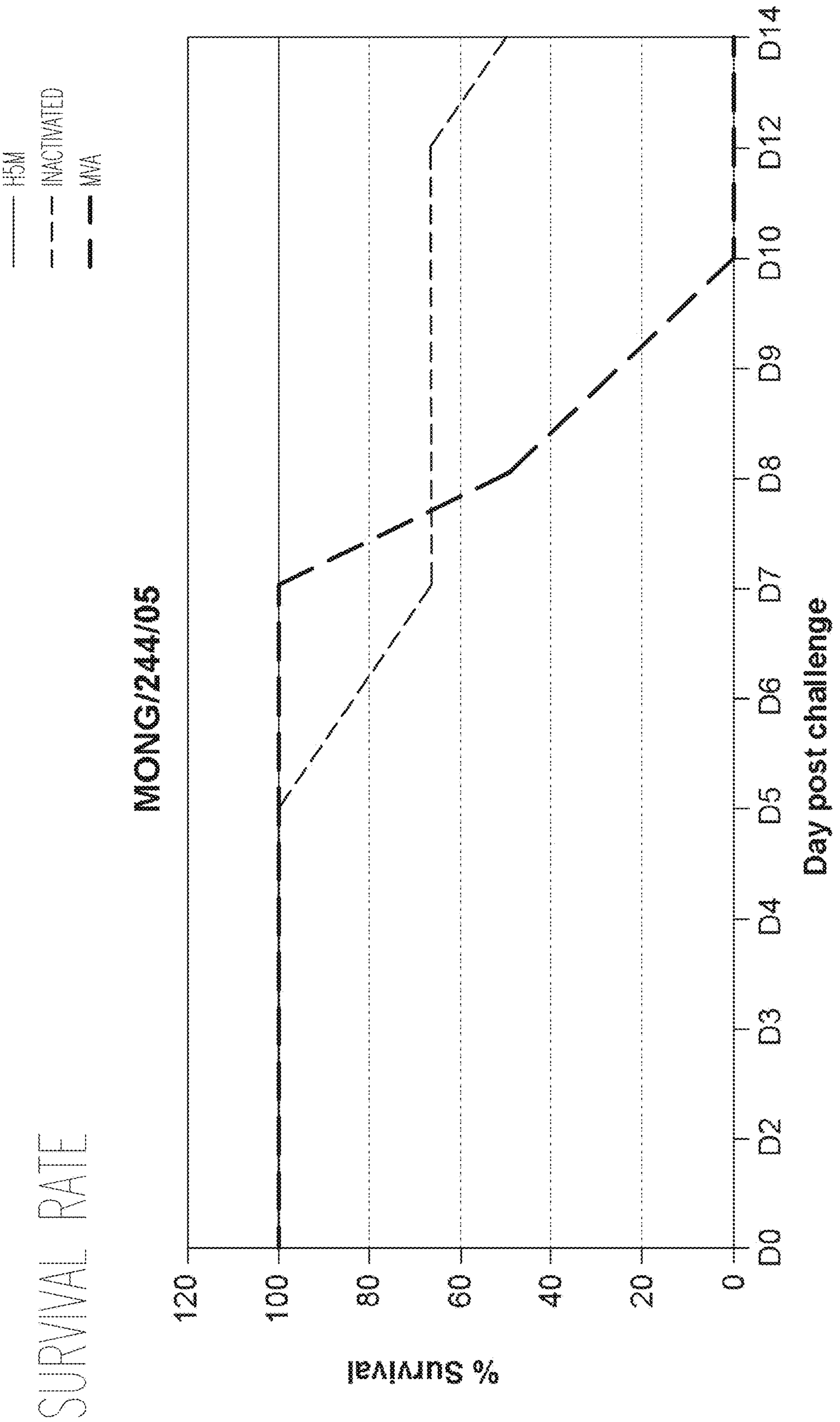
Figure 10C:
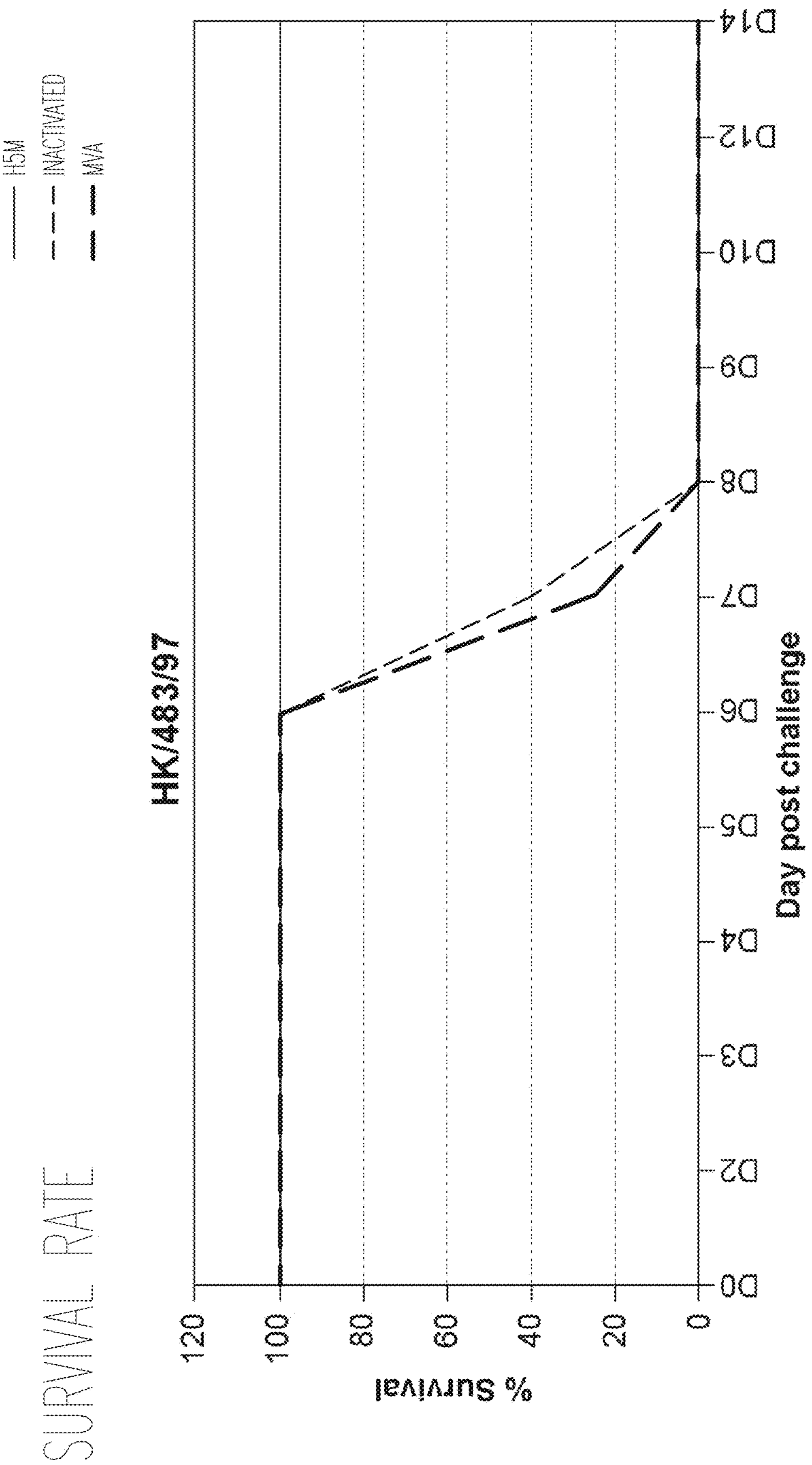
Figure 11A:
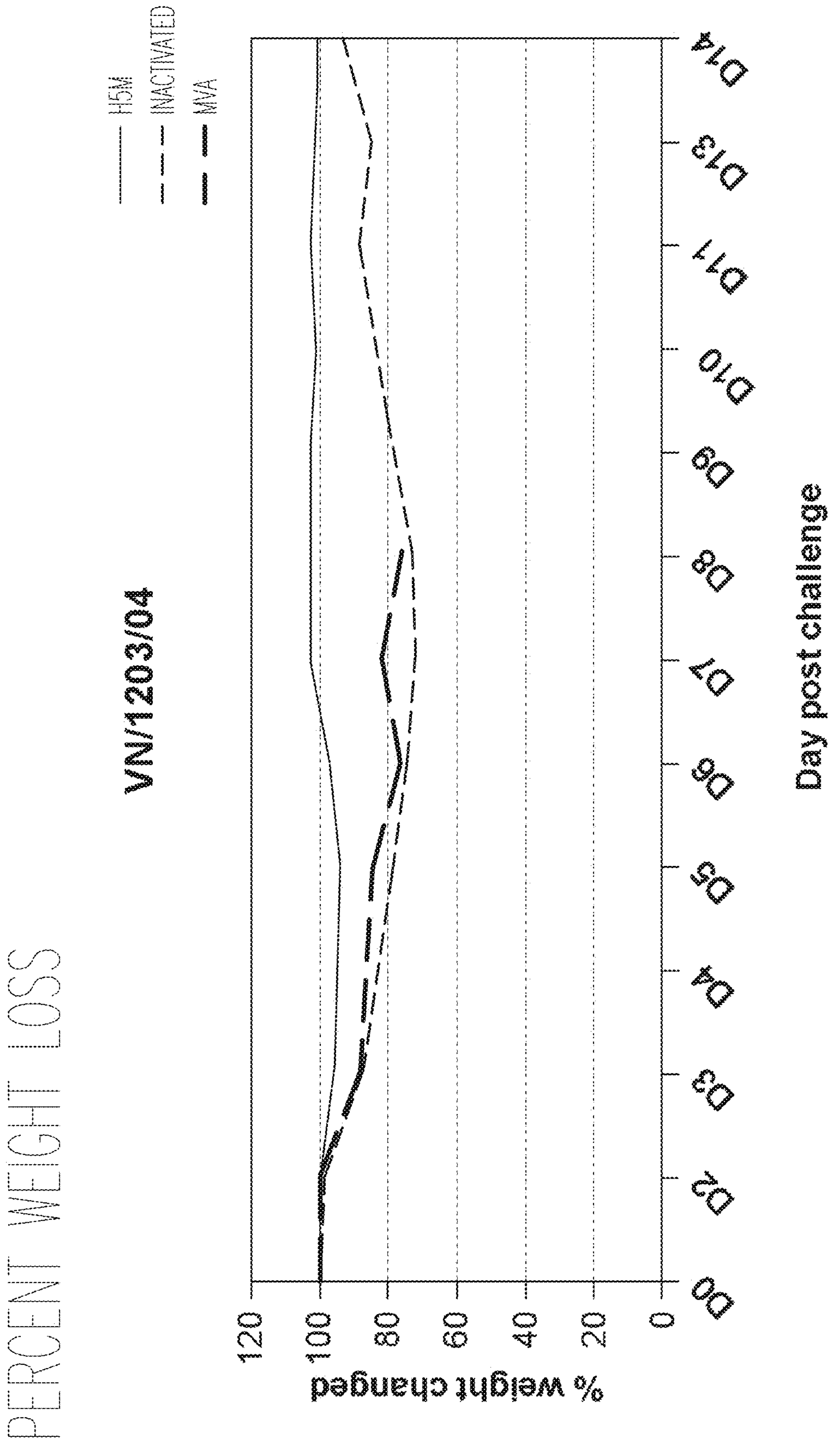
FIGS. 11A-C. Percent weight loss over time in mice immunized with H5M, inactivated virus or vector (MVA) alone and challenged with VN/1203/04 (A); MONG/244/05 (B); and HK/483/97 (C).
Figure 11B:
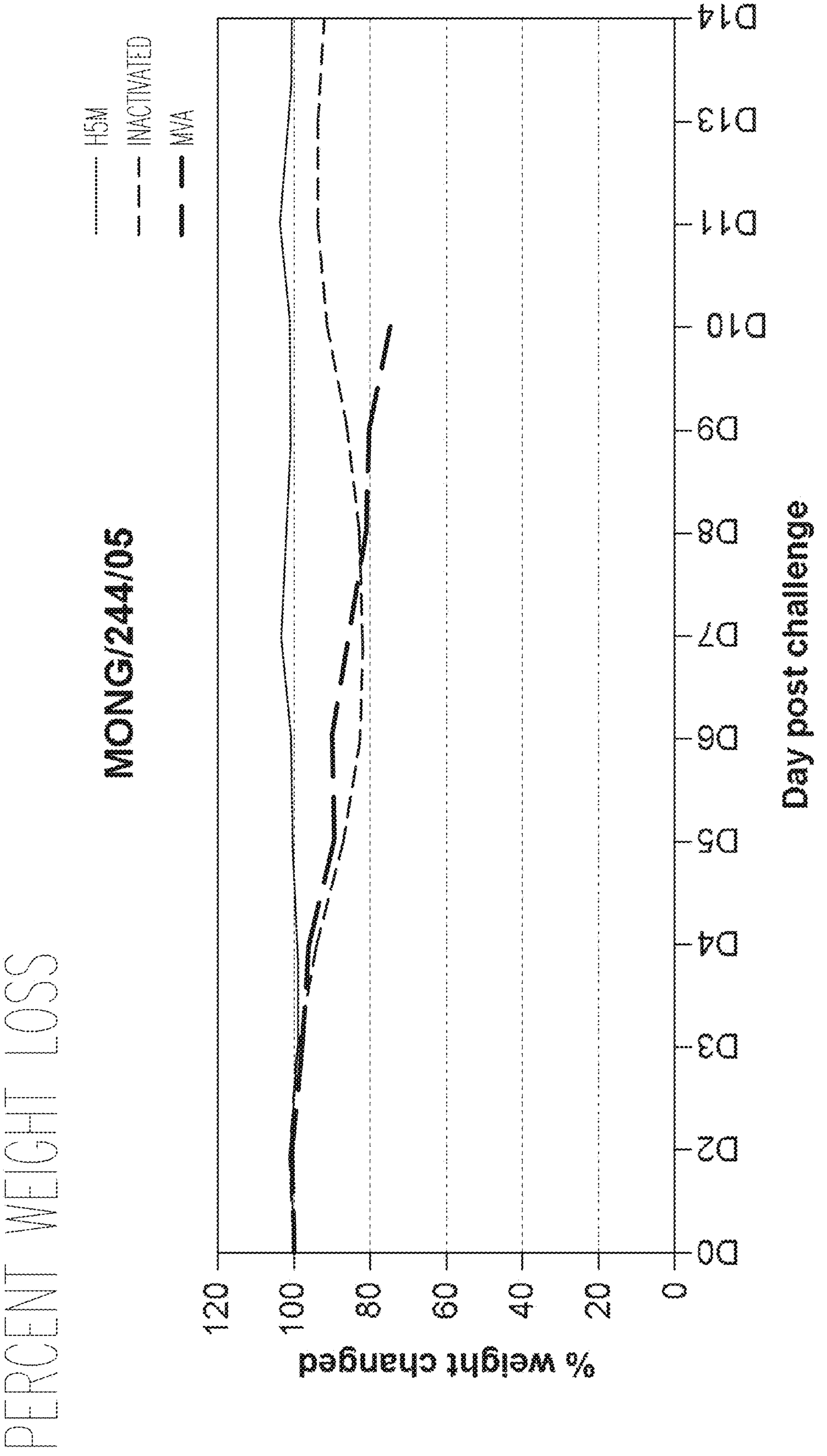
Figure 11C:
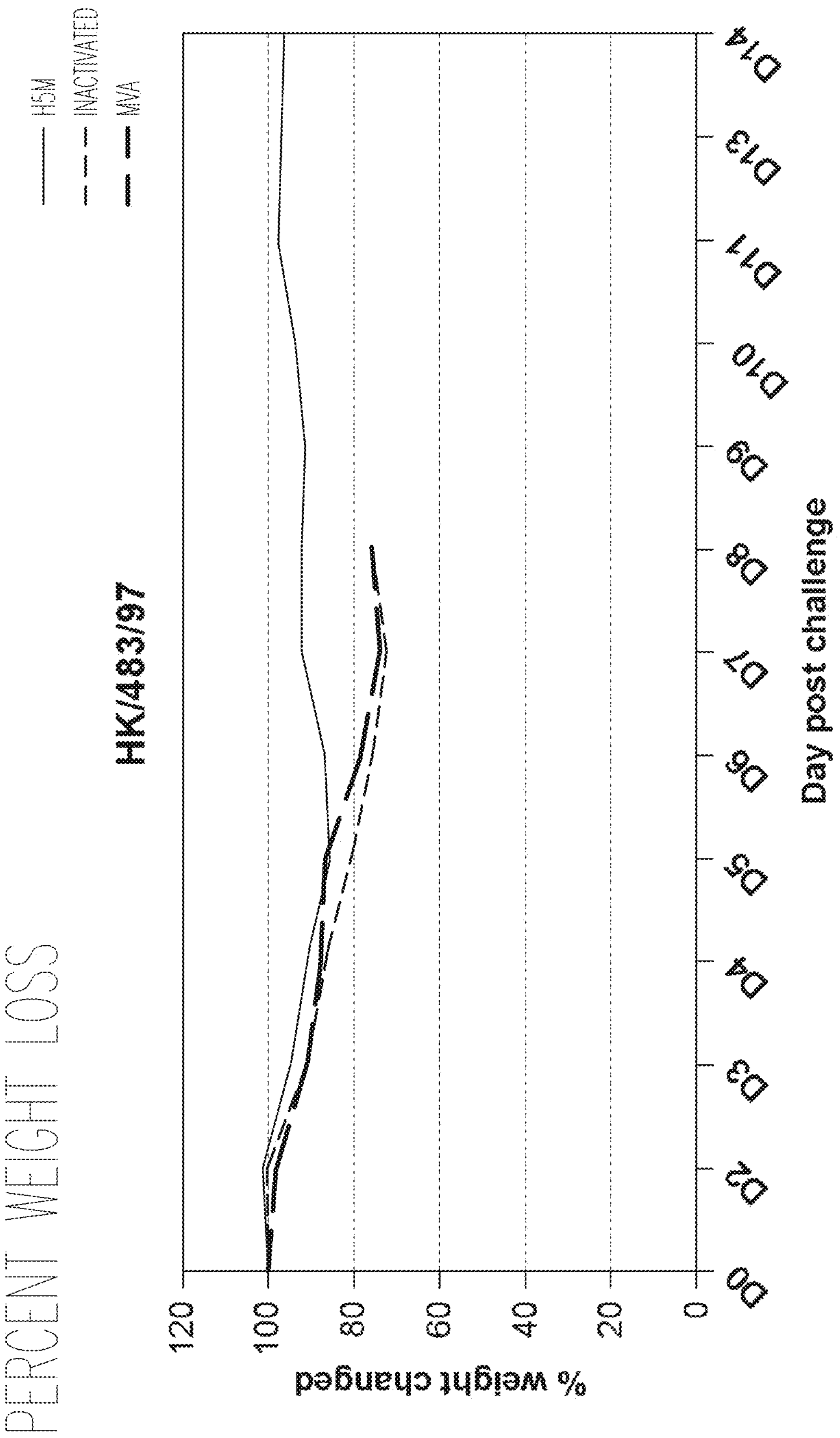
Figure 12A:
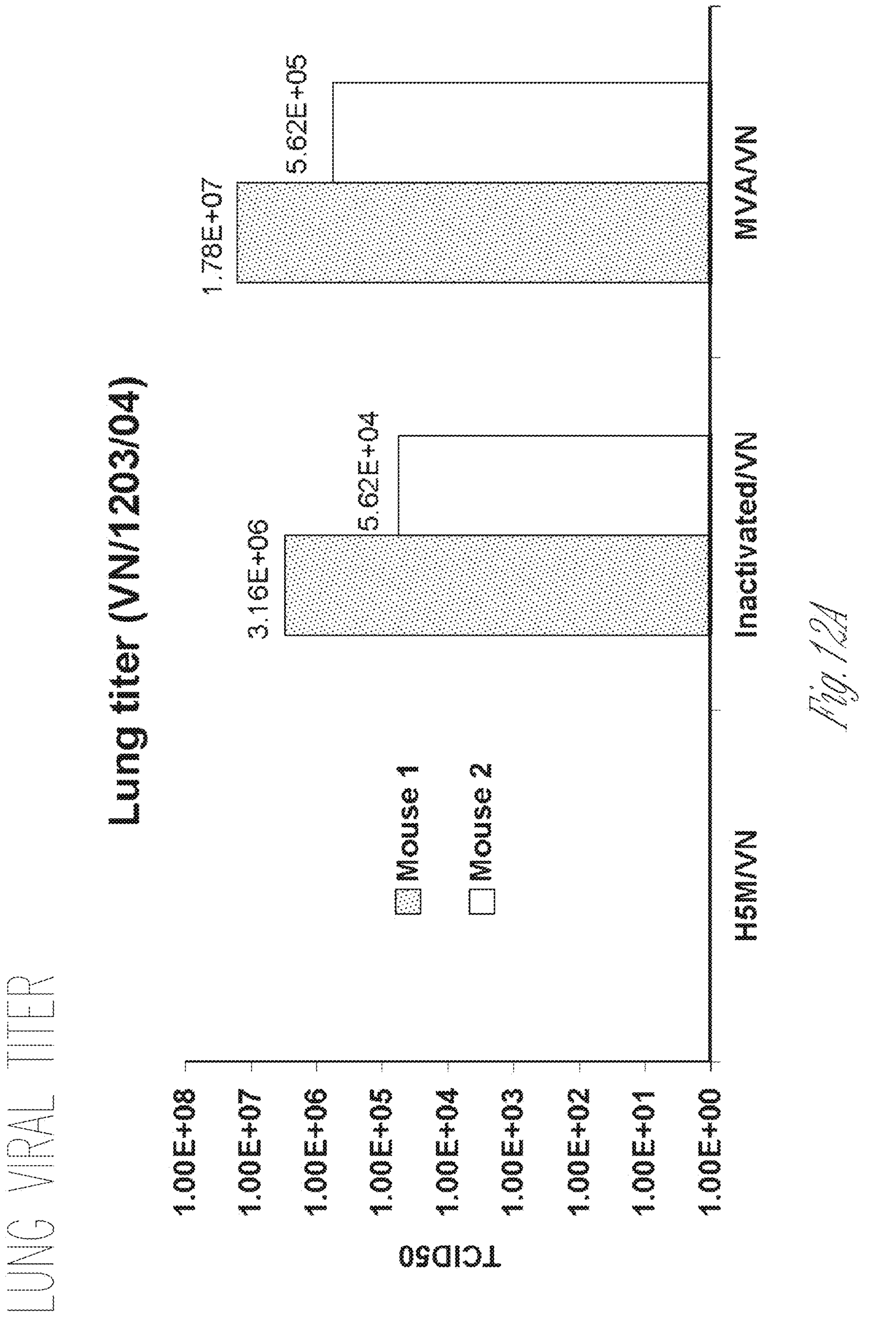
FIGS. 12A-C. Lung viral titers in mice immunized with H5M, inactivated virus or vector (MVA) alone, for VN/1203/04 (A); MONG/244/05(B); and HK/483/97 (C).
Figure 12B:
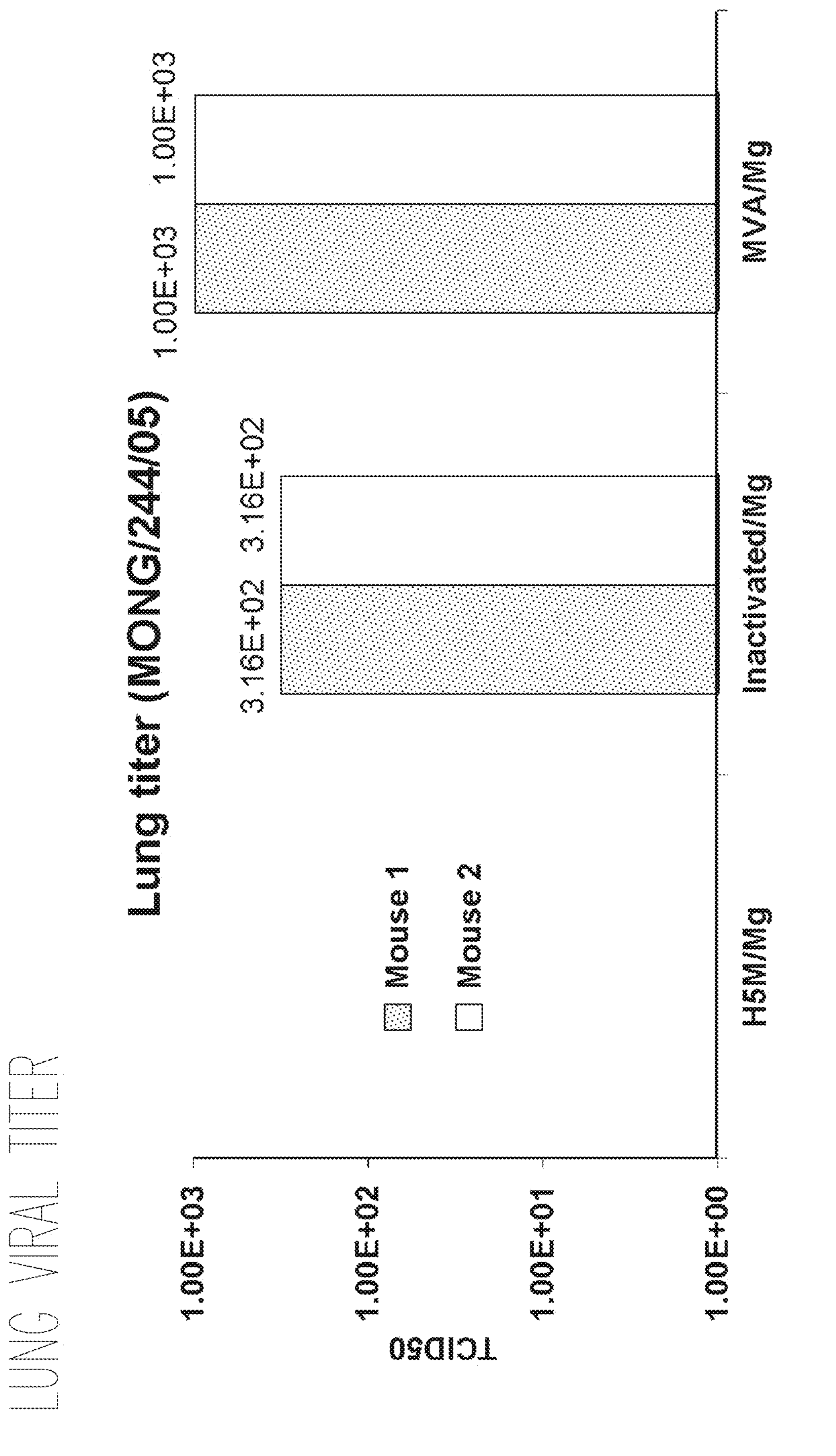
Figure 12C:
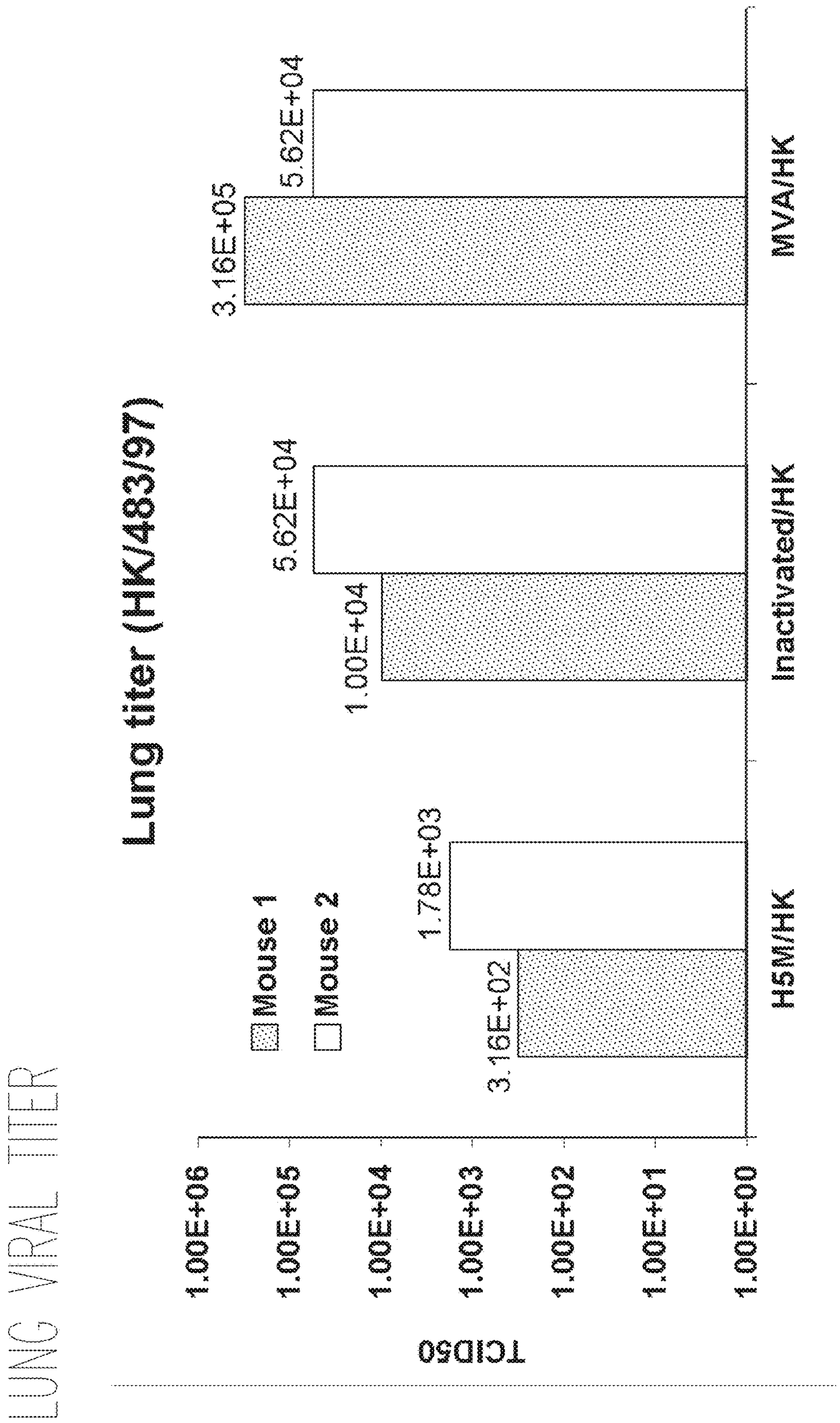

The vaccine protected 100% of the mice against all three challenge strains (FIG. 10). Thus, the MVA-H5M vaccine elicited robust and cross protective immunity in mice against avian influenza strains clade 0, clade 1 and clade 2.2. MVA-H5M lowered weight loss, viral lung titers and prevented severe lung lesions (FIGS. 10-12).

Example III

The genetic algorithm was used to generate other mosaic sequences. 4,809 H1 sequences were used to generate 4 H1M sequences, e.g., using default parameters or modified parameters such as a different random seed number. A characteristic residue in one set of those sequences (SEQ ID Nos. 2 and 3) may be at position 125 (Ile), and a characteristic residue in the other set (SEQ ID Nos. 4 and 5) may be at one or more of positions 62 (Lys), 64 (Ile), 68 (Gln), 71 (Asn), 73 (Ser), 74 (Val), 86 (Leu), 88-91 (IleSerLysGlu), 99-103 (LysProAsnProGlu), 111 (His), or 113 (Ala), or corresponding positions (depending on the length of the signal peptide).

2,931 H3 sequences were used to generate a H3M sequence (SEQ ID NO:7).

393 H2 sequences were used to generate a H2M sequence (SEQ ID NO:6). A characteristic residue in H2M may be at one or more of positions 24 (Ala), 45 (Lys), 86 (Ser), 258 (Thr), 260 (Asn), or 261 (Leu), or corresponding positions.

799 H7 sequences were used to generate a H7M sequence (SEQ ID NO:8). A characteristic residue in H7M may be at one or more of positions 91 (Ser), 92 (Ser), 122 (Arg), 127 (Gly), 195 (Glu), 197 (Val), or 198 (Ser), or corresponding positions.

927 H9 sequences were used to generate a H9M sequence (SEQ ID NO:9). A characteristic residue in H9M may be at one or more of positions 180 (Gln), 215 (Glu) or 240 (Tyr), or corresponding positions.

212 H10 sequences were used to generate a H10M sequence (SEQ ID NO:10). A characteristic residue in H10M may be at position 77 (Val), or a corresponding position.

1,085 HA B sequences were used to generate a HBM sequence (SEQ ID NO:11). A characteristic residue in HBM may be at one or more of positions 86 (Met), 88 (Val), 90 (Thr), 91 (Thr), 95 (Lys), 96 (Ala), or 161 (Val), or corresponding positions.

3,347 sequences were used generated a N1M sequence (SEQ ID NO:12), 4,444 Mosaic sequences were used generated for N2 (SEQ ID NO:13) and 169 sequences were used generated a N7 (SEQ ID NO:14). A characteristic residue in N1M may be at one or more of positions 35 (Ala), 44-48 (AsnHisThrGlyIle), 52 (Arg), 59 (Ser), 64 (His), 70 (Asn), 74-77 (ValValAlaGly), 79-81 (AspLysThr), 99 (Ile), or 105 (Ser). A characteristic residue in N2M may be at one or more of positions 199 (Lys) or 221 (Asn), or corresponding positions.

The approach may thus be employed with any subtype of influenza virus HA or NA, as well as influenza B virus, to generate one or more mosaic influenza antigens that are incorporated into a universal influenza vaccine which provides both domesticated animals and humans with the maximum possible protection against this devastating respiratory disease. Moreover, polyvalent mosaic sequences based on HA and NA may be employed to develop a universal influenza vaccine. The use of poxvirus as a delivery vehicle for the mosaic antigen facilitates immune protection because its replication triggers innate immunity as well as T cell and B cell responses, and the poxvirus can be used in both birds and humans; further, it can be given orally.

To modify the sequences described above, conserved regions may be identified (see FIG. 12). For example, position coverage of mosaic sequences, e.g., for greater than or equal to 80% coverage for SEQ ID NO:1 (H5) includes residues 13-39, 60-75, 111-124, 300-314, 351-388, 401-438, 451-477, 513-516, and 530-537; for SEQ ID NO:2 (H1) includes 21-39, 88-89, 115-125, 284-287, 363-370, 436-439, 472-477, 528-532, and 552-555; for SEQ ID NO:3 (H1) includes 21-24, 37-39, 363-369, 433-438, and 469-476; for SEQ ID NO:4 (H1) includes 21-39, 88-89, 115-125, 363-370, 401-404, 422-423, 433-438, 469-477, and 528-532; for SEQ ID NO:5 (H1) includes 21-24, 37-39, 363-369, 469-476, 528-531, and 552-555; for SEQ ID NO:6 (H2) includes 25-33, 61-75, 104-108, 155-157, 253-271, 287-289, 309-310, 325-339, 351-373, 386-389, 416-439, 457-458, 474-481, 501-508, and 521-531; for SEQ ID NO:7 (H3) includes 24-29, 51-54, 111-125, 301-303, 324-339, 351, 364-365, 378-379, 403-439, 451-454, 470-483, 506-534, and 551-555; for SEQ ID NO:8 (H7) includes 131, 151-153, 293-300, 351-376, 423-431, 464-474, and 511-512; for SEQ ID NO:9 (H9) includes 26-28, 51, 67, 108-109, 254-255, 337-339, 354-360, 414-417, 430-439, and 451-457; for SEQ ID NO:10 (H10) includes 16, 78-86, 101-114, 127-133, 151-154, 167-171, 201-234, 251-259, 301-310, 351-389, 401-415, 419-439, 451-471, 488, 501-513, and 526-530; for SEQ ID NO:11 (HA B) includes 1-39, 101-119, 224-232, 251-254, 283-288, 301-338, 351-388, 401-438, 451-481, 501-508, 521-538, 551-553, and 570-574; for SEQ ID NO:12 (N1) includes 107-143, 174-176, 190-202, 290-299, 398-404, 436-438, 474-484, 506-525, and 538-539; for SEQ ID NO:13 (N2) includes 1-4, 94-113, 156-160, 173-182, 222-237, 287-290, 314-316, 415-419, and 438-451; for SEQ ID NO:14 (N7) includes 1-7, 20-27, 106-114, 127-152, 264-272, 286-290, 338-344, 359-370, 392-402, 417-435, and 456-460.

The conserved regions are those that are included in the mosaic sequences of the invention and may be substituted, e.g., up to 5%, 10% or 20%, relative to the corresponding sequences in any of SEQ ID Nos. 1-14.

REFERENCES

Alexander et al., *Biological sciences/The Royal Society,* 274:1675 (2007).

Allen, *J. Child Healthcare,* 10:178 (2006).

Anonymous, *Lancet Infect. Dis.,* 5:191 (2005).

Bahgat et al., *J. Virol. Methods* 159:244 (2009).

Barouch et al., *Nature Med.,* 16:319 (2010).

Ben-Yedidia and Arnon, *Human Vaccines,* 1:95 (2005).

Bianchi et al., *J. Virol.,* 79:7380 (2005).

Boyd et al., *Vaccine,* 31:670 (2013).

Brewoo et al., *Vaccine,* 31:1848 (2013).

Brown et al., *J. Comp. Path.,* 107:341 (1992).

Bui et al., *Proc. Nat. Acad. Sci. USA,* 104:246 (2007).

Chamnanpood et al., *Southeast Asian J. Tropical Med. Pub. Health,* 42:303 (2011).
Chen et al., *J. Infect. Dis.,* 199:49 (2009).
Chen et al., *Proc. Nat. Acad. Sci. USA,* 105:13538 (2008).
Chiu et al., Annals of the New York Academy of Sciences (2013).
Conly and Johnston, *AMMI Canada,* 15:252 (2004).
Cox et al., *Scand. J. Immunol.,* 59:1 (2004.
De Filette et al., *Vaccine,* 24:6597 (2006).
De Groot et al., *Vaccine,* 23:2136 (2005).
Doria-Rose et al., *J. Virol.,* 79:11214 (2005).
Drexler et al., *Curr. Opin. Biotechnol.* 15:506 (2004).
Earl et al., Current protocols in protein science/editorial board, John E. Coligan et al., Chapter 5:Unit5 12 (2001).
Earl et al., Current protocols in protein science/editorial board, John E. Coligan et al., Chapter 5:Unit5 13 (2001).
Ehrlich et al., *New Eng. J. Med.,* 358:2573 (2008).
Ferguson et al., *Nature,* 437:209 (2005).
Ferguson et al., *Nature,* 442:448 (2006).
Fischer et al., *Nat. Med.,* 13:100 (2007).
Fischer et al., *Nature Med.,* 13:100 (2007).
Gandon et al., *Nature,* 414:751 (2001).
Gao et al., *J. Virol.,* 79:1154 (2005).
Gaschen et al., *Science,* 296:2354 (2002).
Gogolak et al., *Biochem. Biophysical Res. Comm.,* 270:190 (2000).
Hafez et al., *Poultry Sci.,* 89:1609 (2010).
Heiny et al., *PloS One,* 2(11):e1190 (2007).
Herfst et al., *Science,* 336:1534 (2012).
Hessel et al., *PloS One,* 6:e16247 (2011).
Howard et al., *PloS One,* 6:e23791 (2011).
Iwami et al., *J. Theor. Biol.,* 252:732 (2008).
Jefferson et al., *Lancet,* 366:803 (2005).
Jegaskanda et al., *J. Immun.,* 190:1837 (2013).
Kaminski and Lee, *Front Immunol.,* 2:76 (2011).
Kaur et al., *Trends in Immunology,* 32:524 (2011).
Killian, *Meth. Mol. Biol.* 436:47 (2008).
Kreijtz et al., *J. Infect. Dis.,* 199:405 (2009).
Kunisaki and Janoff, *Lancet Infect. Dis.,* 9:493 (2009).
Kuwano et al., *Mol. Immun.,* 28:1 (1991).
Lazzari et al., *Bulletin of the World Health Organization,* 82:242 (2004).
Lillie et al., *Clin Infect Dis.,* 55:19 (2012).
Lipsitch et al., *New Engl. J. Med.,* 361:112 (2009).
Lipsitch et al., *PLoS Medicine,* 4:e15 (2007).
Liu S, et al., *PloS One,* 4:e5022 (2009).
Meltzer et al., *Emerging Infectious Diseases,* 5:659 (1999).
Mostow et al., *Bull. World Health Oman.,* 41:525 (1969).
Mostow et al., *Infect. Immun.,* 26:193 (1979).
Nickle et al., *PLoS Comput. Biol.,* 3:e75 (2007).
Niqueux et al., *Avian Dis.,* 54:502 (2010).
Palker et al., *J. Immunol.,* 142:3612 (1989).
Peck, *JAMA,* 206:2277 (1968).
Pollack et al., *Annals of Emergency Medicine,* 31(5):647-649 (1998).
Rolland et al., *PLoS Pathog.,* 3:e157 (2007).
Santra et al., *Nature Med.,* 16:324 (2010).
Santra et al., *Virology,* 428:121 (2012).
Steel et al., *mBio,* 1:pii e00018-10 (2010).
Stilianakis et al., *J. Infect. Dis.,* 177:863 (1998).
Stittelaar et al., *Vaccine,* 19:3700 (2001).
Thomson et al., *Vaccine,* 23:4647 (2005).
Thurmond et al., *Bioinformatics,* 24:1639 (2008).
Tompkins et al., *Emerg. Infect. Dis.,* 13:426 (2007).
Wright, *New Eng. J. Med.,* 358:2540 (2008).
Wu et al., *Genomics,* 100:102 (2012).
Yamashita et al., *Biochem Biophys Res Commun.,* 393:614 (2010).
Zhao et al., *Virol. J.,* 7:9 (2010).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A vaccine comprising a recombinant influenza virus, the genome of which comprises a nucleotide sequence for an influenza virus HA polypeptide consisting of SEQ ID NO:7 or a nucleotide sequence for an influenza viral HA polypeptide with one amino acid substitution relative to SEQ ID NO:7, or the vaccine comprises an influenza virus HA protein consisting of SEQ ID NO:7 or a protein with one amino acid substitution relative to SEQ ID NO:7, or a combination thereof, which provides cross-clade reactivity.

2. The vaccine of claim 1, further comprising an adjuvant.

3. The vaccine of claim 1, further comprising a different virus.

4. The vaccine of claim 1, further comprising a pharmaceutically acceptable carrier.

5. The vaccine of claim 4, wherein the carrier is suitable for intranasal or intramuscular administration.

6. The vaccine of claim 1, which is in freeze-dried form.

7. The vaccine of claim 1, which is adapted for mucosal, intramuscular or intradermal delivery.

8. The vaccine of claim 1, wherein the influenza virus polypeptide consists of SEQ NO:7, or the influenza virus protein consists of SEQ ID NO:7.

9. A vaccine comprising a recombinant influenza virus, the genome of which comprises a nucleotide sequence for an influenza virus HA polypeptide consisting of SEQ ID NO:7 or a nucleotide sequence for an influenza viral HA polypeptide with one or two amino acid substitutions relative to SEQ ID NO:7, or the vaccine comprises an influenza virus HA protein consisting of SEQ ID NO:7 or a protein with one or two amino acid substitutions relative to SEQ ID NO:7, or a combination thereof, which provides cross-clade reactivity, wherein the one or two substitutions is/are at position(s) 24-29, 51-54, 111-125, 301-303, 324-339, 351, 364-365, 378-379, 403-439, 451-454, 470-483, 506-534, or 551-555.

* * * * *

SEQUENCE LISTING

```
<160> NUMBER OF SEQ ID NOS: 14

<210> SEQ ID NO 1
<211> LENGTH: 568
<212> TYPE: PRT
<213> ORGANISM: Influenzavirus H5N1

<400> SEQUENCE: 1

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
```

-continued

```
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525
```

```
Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565


<210> SEQ ID NO 2
<211> LENGTH: 567
<212> TYPE: PRT
<213> ORGANISM: Influenzavirus H1

<400> SEQUENCE: 2

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
```

```
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Val Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile Lys Asn
                565


<210> SEQ ID NO 3
<211> LENGTH: 566
<212> TYPE: PRT
<213> ORGANISM: Influenzavirus H1

<400> SEQUENCE: 3

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Ile Ser Ser Phe
        115                 120                 125
```

-continued

```
Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
```

545 550 555 560

Gln Cys Arg Val Cys Ile
565

<210> SEQ ID NO 4
<211> LENGTH: 566
<212> TYPE: PRT
<213> ORGANISM: Influenzavirus H1

<400> SEQUENCE: 4

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Leu Leu Lys Gly Ile
50 55 60

Ala Pro Leu Gln Leu Gly Asn Cys Ser Val Ala Gly Trp Ile Leu Gly
65 70 75 80

Asn Pro Glu Cys Glu Leu Leu Ile Ser Lys Glu Ser Trp Ser Tyr Ile
85 90 95

Val Glu Lys Pro Asn Pro Glu Asn Gly Thr Cys Tyr Pro Gly His Phe
100 105 110

Ala Asp Tyr Glu Glu Leu Arg Glu Gln Leu Ser Ser Val Ser Ser Phe
115 120 125

Glu Arg Phe Glu Ile Phe Pro Lys Thr Ser Ser Trp Pro Asn His Asp
130 135 140

Ser Asn Lys Gly Val Thr Ala Ala Cys Pro His Ala Gly Ala Lys Ser
145 150 155 160

Phe Tyr Lys Asn Leu Ile Trp Leu Val Lys Lys Gly Asn Ser Tyr Pro
165 170 175

Lys Leu Ser Lys Ser Tyr Ile Asn Asp Lys Gly Lys Glu Val Leu Val
180 185 190

Leu Trp Gly Ile His His Pro Ser Thr Ser Ala Asp Gln Gln Ser Leu
195 200 205

Tyr Gln Asn Ala Asp Ala Tyr Val Phe Val Gly Thr Ser Arg Tyr Ser
210 215 220

Lys Lys Phe Lys Pro Glu Ile Ala Ile Arg Pro Lys Val Arg Asp Gln
225 230 235 240

Glu Gly Arg Met Asn Tyr Tyr Trp Thr Leu Val Glu Pro Gly Asp Lys
245 250 255

Ile Thr Phe Glu Ala Thr Gly Asn Leu Val Val Pro Arg Tyr Ala Phe
260 265 270

Ala Met Glu Arg Asn Ala Gly Ser Gly Ile Ile Ile Ser Asp Thr Pro
275 280 285

Val His Asp Cys Asn Thr Thr Cys Gln Thr Pro Lys Gly Ala Ile Asn
290 295 300

Thr Ser Leu Pro Phe Gln Asn Ile His Pro Ile Thr Ile Gly Lys Cys
305 310 315 320

Pro Lys Tyr Val Lys Ser Thr Lys Leu Arg Leu Ala Thr Gly Leu Arg
325 330 335

Asn Val Pro Ser Ile Gln Ser Arg Gly Leu Phe Gly Ala Ile Ala Gly
340 345 350

-continued

```
Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asp Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Val Cys Ile
                565
```

<210> SEQ ID NO 5
<211> LENGTH: 567
<212> TYPE: PRT
<213> ORGANISM: Influenzavirus H1

<400> SEQUENCE: 5

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Ile Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160
```

-continued

```
Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asp Glu Ile Thr Asn Lys Val Asn Ser Val Ile Glu
385                 390                 395                 400

Lys Met Asn Thr Gln Phe Thr Ala Val Gly Lys Glu Phe Asn His Leu
                405                 410                 415

Glu Lys Arg Ile Glu Asn Leu Asn Lys Lys Val Asp Asp Gly Phe Leu
            420                 425                 430

Asp Val Trp Thr Tyr Asn Ala Glu Leu Leu Val Leu Leu Glu Asn Glu
        435                 440                 445

Arg Thr Leu Asp Tyr His Asp Ser Asn Val Lys Asn Leu Tyr Glu Lys
    450                 455                 460

Val Arg Ser Gln Leu Lys Asn Asn Ala Lys Glu Ile Gly Asn Gly Cys
465                 470                 475                 480

Phe Glu Phe Tyr His Lys Cys Asp Asn Thr Cys Met Glu Ser Val Lys
                485                 490                 495

Asn Gly Thr Tyr Asp Tyr Pro Lys Tyr Ser Glu Glu Ala Lys Leu Asn
            500                 505                 510

Arg Glu Glu Ile Asp Gly Val Lys Leu Glu Ser Thr Arg Ile Tyr Gln
        515                 520                 525

Ile Leu Ala Ile Tyr Ser Thr Val Ala Ser Ser Leu Val Leu Val Val
    530                 535                 540

Ser Leu Gly Ala Ile Ser Phe Trp Met Cys Ser Asn Gly Ser Leu Gln
545                 550                 555                 560

Cys Arg Ile Cys Ile Lys Asn
                565
```

<210> SEQ ID NO 6
<211> LENGTH: 562
<212> TYPE: PRT
<213> ORGANISM: Influenzavirus H2

<400> SEQUENCE: 6

Met Ala Ile Ile Tyr Leu Ile Leu Leu Phe Thr Ala Val Arg Gly Asp
1 5 10 15

Gln Ile Cys Ile Gly Tyr His Ala Asn Asn Ser Thr Glu Lys Val Asp
20 25 30

Thr Ile Leu Glu Arg Asn Val Thr Val Thr His Ala Lys Asp Ile Leu
35 40 45

Glu Lys Thr His Asn Gly Lys Leu Cys Lys Leu Asn Gly Ile Pro Pro
50 55 60

Leu Glu Leu Gly Asp Cys Ser Ile Ala Gly Trp Leu Leu Gly Asn Pro
65 70 75 80

Glu Cys Asp Arg Leu Leu Ser Val Pro Glu Trp Ser Tyr Ile Met Glu
85 90 95

Lys Glu Asn Pro Arg Asn Gly Leu Cys Tyr Pro Gly Ser Phe Asn Asp
100 105 110

Tyr Glu Glu Leu Lys His Leu Leu Ser Ser Val Thr His Phe Glu Lys
115 120 125

Val Lys Ile Leu Pro Lys Asp Arg Trp Thr Gln His Thr Thr Thr Gly
130 135 140

Gly Ser Arg Ala Cys Ala Val Ser Gly Asn Pro Ser Phe Phe Arg Asn
145 150 155 160

Met Val Trp Leu Thr Lys Lys Gly Ser Asn Tyr Pro Val Ala Lys Gly
165 170 175

Ser Tyr Asn Asn Thr Ser Gly Glu Gln Met Leu Ile Ile Trp Gly Val
180 185 190

His His Pro Asn Asp Glu Thr Glu Gln Arg Thr Leu Tyr Gln Asn Val
195 200 205

Gly Thr Tyr Val Ser Val Gly Thr Ser Thr Leu Asn Lys Arg Ser Ile
210 215 220

Pro Glu Ile Ala Thr Arg Pro Lys Val Asn Gly Gln Gly Gly Arg Met
225 230 235 240

Glu Phe Ser Trp Thr Leu Leu Glu Thr Trp Asp Val Ile Asn Phe Glu
245 250 255

Ser Thr Gly Asn Leu Ile Ala Pro Glu Tyr Gly Phe Lys Ile Ser Lys
260 265 270

Arg Gly Ser Ser Gly Ile Met Lys Thr Glu Gly Thr Leu Glu Asn Cys
275 280 285

Glu Thr Lys Cys Gln Thr Pro Leu Gly Ala Ile Asn Thr Thr Leu Pro
290 295 300

Phe His Asn Ile His Pro Leu Thr Ile Gly Glu Cys Pro Lys Tyr Val
305 310 315 320

Lys Ser Asp Arg Leu Val Leu Ala Thr Gly Leu Arg Asn Val Pro Gln
325 330 335

Ile Glu Ser Arg Gly Leu Phe Gly Ala Ile Ala Gly Phe Ile Glu Gly
340 345 350

Gly Trp Gln Gly Met Val Asp Gly Trp Tyr Gly Tyr His His Ser Asn
355 360 365

Asp Gln Gly Ser Gly Tyr Ala Ala Asp Lys Glu Ser Thr Gln Lys Ala
370 375 380

```
Ile Asp Gly Ile Thr Asn Lys Val Asn Ser Val Ile Glu Lys Met Asn
385                 390                 395                 400

Thr Gln Phe Glu Ala Val Gly Lys Glu Phe Asn Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Ala Lys Glu Ile Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Asn Met Gly Val Tyr Gln Ile Leu Ala
        515                 520                 525

Ile Tyr Ala Thr Val Ala Gly Ser Leu Ser Leu Ala Ile Met Ile Ala
    530                 535                 540

Gly Ile Ser Phe Trp Met Cys Ser Asn Gly Ser Leu Gln Cys Arg Ile
545                 550                 555                 560

Cys Ile


<210> SEQ ID NO 7
<211> LENGTH: 566
<212> TYPE: PRT
<213> ORGANISM: Influenzavirus H3

<400> SEQUENCE: 7

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190
```

```
Leu Tyr Ile Trp Gly Val His His Pro Gly Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565
```

<210> SEQ ID NO 8
<211> LENGTH: 560
<212> TYPE: PRT
<213> ORGANISM: Influenzavirus H7

<400> SEQUENCE: 8

```
Met Asn Ile Gln Ile Leu Ala Phe Ile Ala Cys Val Leu Thr Gly Ala
1               5                   10                  15

Lys Gly Asp Lys Ile Cys Leu Gly His His Ala Val Ala Asn Gly Thr
            20                  25                  30

Lys Val Asn Thr Leu Thr Glu Arg Gly Ile Glu Val Val Asn Ala Thr
        35                  40                  45

Glu Thr Val Glu Thr Ala Asn Ile Lys Lys Ile Cys Thr Gln Gly Lys
    50                  55                  60

Arg Pro Thr Asp Leu Gly Gln Cys Gly Leu Leu Gly Thr Leu Ile Gly
65                  70                  75                  80

Pro Pro Gln Cys Asp Gln Phe Leu Glu Phe Ser Ser Asp Leu Ile Ile
                85                  90                  95

Glu Arg Arg Glu Gly Thr Asp Val Cys Tyr Pro Gly Lys Phe Thr Asn
            100                 105                 110

Glu Glu Ser Leu Arg Gln Ile Leu Arg Arg Ser Gly Gly Ile Gly Lys
        115                 120                 125

Glu Ser Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Ser Asp Asn Ala Ala Phe Pro Gln Met Thr Lys Ser
                165                 170                 175

Tyr Arg Asn Pro Arg Asn Lys Pro Ala Leu Ile Ile Trp Gly Val His
            180                 185                 190

His Ser Glu Ser Val Ser Glu Gln Thr Lys Leu Tyr Gly Ser Gly Asn
        195                 200                 205

Lys Leu Ile Thr Val Gly Ser Ser Lys Tyr Gln Gln Ser Phe Thr Pro
    210                 215                 220

Ser Pro Gly Ala Arg Pro Gln Val Asn Gly Gln Ser Gly Arg Ile Asp
225                 230                 235                 240

Phe His Trp Leu Leu Leu Asp Pro Asn Asp Thr Val Thr Phe Thr Phe
                245                 250                 255

Asn Gly Ala Phe Ile Ala Pro Asp Arg Ala Ser Phe Phe Arg Gly Glu
            260                 265                 270

Ser Leu Gly Val Gln Ser Asp Val Pro Leu Asp Ser Gly Cys Glu Gly
        275                 280                 285

Asp Cys Phe His Ser Gly Gly Thr Ile Val Ser Ser Leu Pro Phe Gln
    290                 295                 300

Asn Ile Asn Pro Arg Thr Val Gly Lys Cys Pro Arg Tyr Val Lys Gln
305                 310                 315                 320

Lys Ser Leu Leu Leu Ala Thr Gly Met Arg Asn Val Pro Glu Asn Pro
                325                 330                 335

Lys Thr Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Ile Glu Gln Gln Ile
                405                 410                 415
```

```
Gly Asn Val Ile Asn Trp Thr Arg Asp Ser Met Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asn Lys Leu Tyr Glu Arg Val Arg Lys Gln
    450                 455                 460

Leu Arg Glu Asn Ala Glu Glu Asp Gly Thr Gly Cys Phe Glu Ile Phe
465                 470                 475                 480

His Lys Cys Asp Asp Gln Cys Met Glu Ser Ile Arg Asn Asn Thr Tyr
                485                 490                 495

Asp His Thr Gln Tyr Arg Thr Glu Ser Leu Gln Asn Arg Ile Gln Ile
            500                 505                 510

Asp Pro Val Lys Leu Ser Ser Gly Tyr Lys Asp Ile Ile Leu Trp Phe
        515                 520                 525

Ser Phe Gly Ala Ser Cys Phe Leu Leu Leu Ala Ile Ala Met Gly Leu
    530                 535                 540

Val Phe Ile Cys Ile Lys Asn Gly Asn Met Arg Cys Thr Ile Cys Ile
545                 550                 555                 560


<210> SEQ ID NO 9
<211> LENGTH: 560
<212> TYPE: PRT
<213> ORGANISM: Influenzavirus H9

<400> SEQUENCE: 9

Met Glu Val Val Ser Leu Ile Thr Ile Leu Leu Val Val Thr Val Ser
1               5                   10                  15

Asn Ala Asp Lys Ile Cys Ile Gly Tyr Gln Ser Thr Asn Ser Thr Glu
            20                  25                  30

Thr Val Asp Thr Leu Thr Glu Asn Asn Val Pro Val Thr His Ala Lys
        35                  40                  45

Glu Leu Leu His Thr Glu His Asn Gly Met Leu Cys Ala Thr Asn Leu
    50                  55                  60

Gly His Pro Leu Ile Leu Asp Thr Cys Thr Ile Glu Gly Leu Ile Tyr
65                  70                  75                  80

Gly Asn Pro Ser Cys Asp Leu Leu Leu Gly Gly Arg Glu Trp Ser Tyr
                85                  90                  95

Ile Val Glu Arg Pro Ser Ala Val Asn Gly Leu Cys Tyr Pro Gly Asn
            100                 105                 110

Val Glu Asn Leu Glu Glu Leu Arg Ser Leu Phe Ser Ser Ala Ser Ser
        115                 120                 125

Tyr Gln Arg Ile Gln Ile Phe Pro Asp Thr Ile Trp Asn Val Ser Tyr
    130                 135                 140

Ser Gly Thr Ser Lys Ala Cys Ser Asp Ser Phe Tyr Arg Ser Met Arg
145                 150                 155                 160

Trp Leu Thr Gln Lys Asn Asn Ala Tyr Pro Ile Gln Asp Ala Gln Tyr
                165                 170                 175

Thr Asn Asn Gln Glu Lys Asn Ile Leu Phe Met Trp Gly Ile Asn His
            180                 185                 190

Pro Pro Thr Asp Thr Ala Gln Thr Asn Leu Tyr Thr Arg Thr Asp Thr
        195                 200                 205

Thr Thr Ser Val Ala Thr Glu Glu Ile Asn Arg Thr Phe Lys Pro Leu
    210                 215                 220

Ile Gly Pro Arg Pro Leu Val Asn Gly Leu Gln Gly Arg Ile Asp Tyr
```

-continued

```
225                 230                 235                 240

Tyr Trp Ser Val Leu Lys Pro Gly Gln Thr Leu Arg Val Arg Ser Asn
                245                 250                 255

Gly Asn Leu Ile Ala Pro Trp Tyr Gly His Ile Leu Ser Gly Glu Ser
            260                 265                 270

His Gly Arg Ile Leu Lys Thr Asp Leu Asn Ser Gly Asn Cys Val Val
        275                 280                 285

Gln Cys Gln Thr Glu Lys Gly Gly Leu Asn Thr Thr Leu Pro Phe His
    290                 295                 300

Asn Val Ser Lys Tyr Ala Phe Gly Asn Cys Pro Lys Tyr Val Gly Val
305                 310                 315                 320

Lys Ser Leu Lys Leu Ala Val Gly Leu Arg Asn Val Pro Ala Arg Ser
                325                 330                 335

Ser Arg Gly Leu Phe Gly Ala Ile Ala Gly Phe Ile Glu Gly Gly Trp
            340                 345                 350

Ser Gly Leu Val Ala Gly Trp Tyr Gly Phe Gln His Ser Asn Asp Gln
        355                 360                 365

Gly Val Gly Met Ala Ala Asp Arg Asp Ser Thr Gln Lys Ala Ile Asp
    370                 375                 380

Lys Ile Thr Ser Lys Val Asn Asn Ile Val Asp Lys Met Asn Lys Gln
385                 390                 395                 400

Tyr Glu Ile Ile Asp His Glu Phe Ser Glu Val Glu Thr Arg Leu Asn
                405                 410                 415

Met Ile Asn Asn Lys Ile Asp Asp Gln Ile Gln Asp Ile Trp Ala Tyr
            420                 425                 430

Asn Ala Glu Leu Leu Val Leu Leu Glu Asn Gln Lys Thr Leu Asp Glu
        435                 440                 445

His Asp Ala Asn Val Asn Asn Leu Tyr Asn Lys Val Lys Arg Ala Leu
    450                 455                 460

Gly Ser Asn Ala Val Glu Asp Gly Lys Gly Cys Phe Glu Leu Tyr His
465                 470                 475                 480

Lys Cys Asp Asp Gln Cys Met Glu Thr Ile Arg Asn Gly Thr Tyr Asn
                485                 490                 495

Arg Arg Lys Tyr Lys Glu Glu Ser Arg Leu Glu Arg Gln Lys Ile Glu
            500                 505                 510

Gly Val Lys Leu Glu Ser Glu Gly Thr Tyr Lys Ile Leu Thr Ile Tyr
        515                 520                 525

Ser Thr Val Ala Ser Ser Leu Val Ile Ala Met Gly Phe Ala Ala Phe
    530                 535                 540

Leu Phe Trp Ala Met Ser Asn Gly Ser Cys Arg Cys Asn Ile Cys Ile
545                 550                 555                 560


<210> SEQ ID NO 10
<211> LENGTH: 561
<212> TYPE: PRT
<213> ORGANISM: Influenzavirus H10

<400> SEQUENCE: 10

Met Tyr Lys Ile Val Leu Val Leu Ala Leu Leu Gly Ala Val His Gly
1               5                   10                  15

Leu Asp Lys Ile Cys Leu Gly His His Ala Val Ser Asn Gly Thr Ile
            20                  25                  30

Val Lys Thr Leu Thr Asn Glu Lys Glu Glu Val Thr Asn Ala Thr Glu
        35                  40                  45
```

-continued

```
Thr Val Glu Ser Lys Ser Leu Asp Lys Leu Cys Met Lys Ser Arg Asn
    50                  55                  60

Tyr Lys Asp Leu Gly Asn Cys His Pro Ile Gly Met Val Ile Gly Thr
65                  70                  75                  80

Pro Ala Cys Asp Leu His Leu Thr Gly Thr Trp Asp Thr Leu Ile Glu
                85                  90                  95

Arg Asp Asn Ser Ile Ala Tyr Cys Tyr Pro Gly Ala Thr Val Asn Glu
            100                 105                 110

Glu Ala Leu Arg Gln Lys Ile Met Glu Ser Gly Gly Ile Asp Lys Ile
        115                 120                 125

Ser Thr Gly Phe Thr Tyr Gly Ser Ser Ile Asn Ser Ala Gly Thr Thr
    130                 135                 140

Lys Ala Cys Met Arg Asn Gly Gly Asn Ser Phe Tyr Ala Glu Leu Lys
145                 150                 155                 160

Trp Leu Val Ser Lys Ser Lys Gly Gln Asn Phe Pro Gln Thr Thr Asn
                165                 170                 175

Thr Tyr Arg Asn Thr Asp Ser Ala Glu His Leu Ile Ile Trp Gly Ile
            180                 185                 190

His His Pro Ser Ser Thr Gln Glu Lys Asn Asp Leu Tyr Gly Thr Gln
        195                 200                 205

Ser Leu Ser Ile Ser Val Gly Ser Ser Thr Tyr Gln Asn Asn Phe Val
    210                 215                 220

Pro Val Val Gly Ala Arg Pro Gln Val Asn Gly Gln Ser Gly Arg Ile
225                 230                 235                 240

Asp Phe His Trp Thr Met Val Gln Pro Gly Asp Asn Ile Thr Phe Ser
                245                 250                 255

His Asn Gly Gly Leu Ile Ala Pro Ser Arg Val Ser Lys Leu Lys Gly
            260                 265                 270

Arg Gly Leu Gly Ile Gln Ser Gly Ala Ser Val Asp Asn Asp Cys Glu
        275                 280                 285

Ser Lys Cys Phe Trp Lys Gly Gly Ser Ile Asn Thr Lys Leu Pro Phe
    290                 295                 300

Gln Asn Leu Ser Pro Arg Thr Val Gly Gln Cys Pro Lys Tyr Val Asn
305                 310                 315                 320

Lys Lys Ser Leu Leu Leu Ala Thr Gly Met Arg Asn Val Pro Glu Val
                325                 330                 335

Val Gln Gly Arg Gly Leu Phe Gly Ala Ile Ala Gly Phe Ile Glu Asn
            340                 345                 350

Gly Trp Glu Gly Met Val Asp Gly Trp Tyr Gly Phe Arg His Gln Asn
        355                 360                 365

Ala Gln Gly Thr Gly Gln Ala Ala Asp Tyr Lys Ser Thr Gln Ala Ala
    370                 375                 380

Ile Asp Gln Ile Thr Gly Lys Leu Asn Arg Leu Ile Glu Lys Thr Asn
385                 390                 395                 400

Thr Glu Phe Glu Ser Ile Glu Ser Glu Phe Ser Glu Ile Glu His Gln
                405                 410                 415

Ile Gly Asn Val Ile Asn Trp Thr Lys Asp Ser Ile Thr Asp Ile Trp
            420                 425                 430

Thr Tyr Gln Ala Glu Leu Leu Val Ala Met Glu Asn Gln His Thr Ile
        435                 440                 445

Asp Met Ala Asp Ser Glu Met Leu Asn Leu Tyr Glu Arg Val Arg Lys
    450                 455                 460

Gln Leu Arg Gln Asn Ala Glu Glu Asp Gly Lys Gly Cys Phe Glu Ile
```

465 470 475 480

Tyr His Lys Cys Asp Asp Asn Cys Met Glu Ser Ile Arg Asn Asn Thr
485 490 495

Tyr Asp His Thr Gln Tyr Arg Glu Glu Ala Leu Leu Asn Arg Leu Asn
500 505 510

Ile Asn Pro Val Lys Leu Ser Ser Gly Tyr Lys Asp Val Ile Leu Trp
515 520 525

Phe Ser Phe Gly Ala Ser Cys Phe Val Leu Leu Ala Val Ile Met Gly
530 535 540

Leu Val Phe Phe Cys Leu Lys Asn Gly Asn Met Arg Cys Thr Ile Cys
545 550 555 560

Ile

<210> SEQ ID NO 11
<211> LENGTH: 585
<212> TYPE: PRT
<213> ORGANISM: Influenzavirus B

<400> SEQUENCE: 11

Met Lys Ala Ile Ile Val Leu Leu Met Val Val Thr Ser Asn Ala Asp
1 5 10 15

Arg Ile Cys Thr Gly Ile Thr Ser Ser Asn Ser Pro His Val Val Lys
20 25 30

Thr Ala Thr Gln Gly Glu Val Asn Val Thr Gly Val Ile Pro Leu Thr
35 40 45

Thr Thr Pro Thr Lys Ser His Phe Ala Asn Leu Lys Gly Thr Glu Thr
50 55 60

Arg Gly Lys Leu Cys Pro Lys Cys Leu Asn Cys Thr Asp Leu Asp Val
65 70 75 80

Ala Leu Gly Arg Pro Met Cys Val Gly Thr Thr Pro Ser Ala Lys Ala
85 90 95

Ser Ile Leu His Glu Val Arg Pro Val Thr Ser Gly Cys Phe Pro Ile
100 105 110

Met His Asp Arg Thr Lys Ile Arg Gln Leu Pro Asn Leu Leu Arg Gly
115 120 125

Tyr Glu His Ile Arg Leu Ser Thr His Asn Val Ile Asn Ala Glu Asn
130 135 140

Ala Pro Gly Gly Pro Tyr Lys Ile Gly Thr Ser Gly Ser Cys Pro Asn
145 150 155 160

Val Thr Asn Gly Asn Gly Phe Phe Ala Thr Met Ala Trp Ala Val Pro
165 170 175

Lys Asn Asp Lys Asn Lys Thr Ala Thr Asn Pro Leu Thr Ile Glu Val
180 185 190

Pro Tyr Ile Cys Thr Glu Gly Glu Asp Gln Ile Thr Val Trp Gly Phe
195 200 205

His Ser Asp Asn Glu Thr Gln Met Ala Lys Leu Tyr Gly Asp Ser Lys
210 215 220

Pro Gln Lys Phe Thr Ser Ser Ala Asn Gly Val Thr Thr His Tyr Val
225 230 235 240

Ser Gln Ile Gly Gly Phe Pro Asn Gln Thr Glu Asp Gly Gly Leu Pro
245 250 255

Gln Ser Gly Arg Ile Val Val Asp Tyr Met Val Gln Lys Ser Gly Lys
260 265 270

Thr Gly Thr Ile Thr Tyr Gln Arg Gly Ile Leu Leu Pro Gln Lys Val

```
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asn Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585


<210> SEQ ID NO 12
<211> LENGTH: 470
<212> TYPE: PRT
<213> ORGANISM: Influenzavirus N1

<400> SEQUENCE: 12

Lys Met Asn Pro Asn Gln Lys Ile Ile Thr Ile Gly Ser Ile Cys Met
1               5                   10                  15

Val Ile Gly Ile Val Ser Leu Met Leu Gln Ile Gly Asn Ile Ile Ser
            20                  25                  30

Ile Trp Ala Ser His Ser Ile Gln Thr Gly Ser Gln Asn His Thr Gly
        35                  40                  45

Ile Cys Asn Gln Arg Ile Ile Thr Tyr Glu Asn Ser Thr Trp Val Asn
    50                  55                  60
```

-continued

```
His Thr Tyr Val Asn Ile Asn Asn Thr Asn Val Val Ala Gly Lys Asp
65                  70                  75                  80

Lys Thr Ser Val Thr Leu Ala Gly Asn Ser Ser Leu Cys Pro Ile Ser
                85                  90                  95

Gly Trp Ala Ile Tyr Ser Lys Asp Asn Ser Ile Arg Ile Gly Ser Lys
            100                 105                 110

Gly Asp Val Phe Val Ile Arg Glu Pro Phe Ile Ser Cys Ser His Leu
        115                 120                 125

Glu Cys Arg Thr Phe Phe Leu Thr Gln Gly Ala Leu Leu Asn Asp Lys
    130                 135                 140

His Ser Asn Gly Thr Val Lys Asp Arg Ser Pro His Arg Thr Leu Met
145                 150                 155                 160

Ser Cys Pro Val Gly Glu Ala Pro Ser Pro Tyr Asn Ser Arg Phe Glu
                165                 170                 175

Ser Val Ala Trp Ser Ala Ser Ala Cys His Asp Gly Thr Ser Trp Leu
            180                 185                 190

Thr Ile Gly Ile Ser Gly Pro Asp Asn Gly Ala Val Ala Val Leu Lys
        195                 200                 205

Tyr Asn Gly Ile Ile Thr Asp Thr Ile Lys Ser Trp Arg Asn Asn Ile
    210                 215                 220

Leu Arg Thr Gln Glu Ser Glu Cys Ala Cys Val Asn Gly Ser Cys Phe
225                 230                 235                 240

Thr Val Met Thr Asp Gly Pro Ser Asn Gly Gln Ala Ser Tyr Lys Ile
                245                 250                 255

Phe Lys Met Glu Lys Gly Lys Val Val Lys Ser Val Glu Leu Asp Ala
            260                 265                 270

Pro Asn Tyr His Tyr Glu Glu Cys Ser Cys Tyr Pro Asp Ala Gly Glu
        275                 280                 285

Ile Thr Cys Val Cys Arg Asp Asn Trp His Gly Ser Asn Arg Pro Trp
    290                 295                 300

Val Ser Phe Asn Gln Asn Leu Glu Tyr Gln Ile Gly Tyr Ile Cys Ser
305                 310                 315                 320

Gly Val Phe Gly Asp Asn Pro Arg Pro Asn Asp Gly Thr Gly Ser Cys
                325                 330                 335

Gly Pro Val Ser Ser Asn Gly Ala Tyr Gly Val Lys Gly Phe Ser Phe
            340                 345                 350

Lys Tyr Gly Asn Gly Val Trp Ile Gly Arg Thr Lys Ser Thr Asn Ser
        355                 360                 365

Arg Ser Gly Phe Glu Met Ile Trp Asp Pro Asn Gly Trp Thr Glu Thr
    370                 375                 380

Asp Ser Ser Phe Ser Val Lys Gln Asp Ile Val Ala Ile Thr Asp Trp
385                 390                 395                 400

Ser Gly Tyr Ser Gly Ser Phe Val Gln His Pro Glu Leu Thr Gly Leu
                405                 410                 415

Asp Cys Ile Arg Pro Cys Phe Trp Val Glu Leu Ile Arg Gly Arg Pro
            420                 425                 430

Lys Glu Ser Thr Ile Trp Thr Ser Gly Ser Ser Ile Ser Phe Cys Gly
        435                 440                 445

Val Asn Ser Asp Thr Val Gly Trp Ser Trp Pro Asp Gly Ala Glu Leu
    450                 455                 460

Pro Phe Thr Ile Asp Lys
465                 470
```

<210> SEQ ID NO 13
<211> LENGTH: 469
<212> TYPE: PRT
<213> ORGANISM: Influenzavirus N2

<400> SEQUENCE: 13

```
Met Asn Pro Asn Gln Lys Ile Ile Thr Ile Gly Ser Val Ser Leu Thr
1               5                   10                  15

Ile Ala Thr Ile Cys Phe Leu Met Gln Ile Ala Ile Leu Val Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Gly His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asn
        195                 200                 205

Gly Arg Leu Val Asp Ser Ile Gly Ser Trp Ser Lys Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380
```

-continued

```
Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465


<210> SEQ ID NO 14
<211> LENGTH: 470
<212> TYPE: PRT
<213> ORGANISM: Influenzavirus N7

<400> SEQUENCE: 14

Met Asn Pro Asn Gln Lys Leu Phe Ala Leu Ser Gly Val Ala Ile Ala
1               5                   10                  15

Leu Ser Ile Leu Asn Leu Leu Ile Gly Ile Ser Asn Val Gly Leu Asn
            20                  25                  30

Val Ser Leu His Leu Lys Gly Ser Asn Asp Gln Asp Lys Asn Trp Thr
        35                  40                  45

Cys Thr Ser Val Thr Gln Asn Asn Thr Thr Leu Ile Glu Asn Thr Tyr
    50                  55                  60

Val Asn Asn Thr Thr Val Ile Asn Lys Glu Thr Gly Thr Ala Lys Gln
65                  70                  75                  80

Asn Tyr Leu Met Leu Asn Lys Ser Leu Cys Lys Val Glu Gly Trp Val
                85                  90                  95

Val Val Ala Lys Asp Asn Ala Ile Arg Phe Gly Glu Ser Glu Gln Ile
            100                 105                 110

Ile Val Thr Arg Glu Pro Tyr Val Ser Cys Asp Pro Leu Gly Cys Lys
        115                 120                 125

Met Tyr Ala Leu His Gln Gly Thr Thr Ile Arg Asn Lys His Ser Asn
    130                 135                 140

Gly Thr Ile His Asp Arg Thr Ala Phe Arg Gly Leu Ile Ser Thr Pro
145                 150                 155                 160

Leu Gly Ser Pro Pro Ile Val Ser Asn Ser Asp Phe Leu Cys Val Gly
                165                 170                 175

Trp Ser Ser Thr Ser Cys His Asp Gly Ile Gly Arg Met Thr Ile Cys
            180                 185                 190

Val Gln Gly Asn Asn Asp Asn Ala Thr Ala Thr Val Tyr Tyr Asp Arg
        195                 200                 205

Arg Leu Thr Thr Thr Ile Lys Thr Trp Ala Gly Asn Ile Leu Arg Thr
    210                 215                 220

Gln Glu Ser Glu Cys Val Cys His Asn Gly Thr Cys Val Val Ile Met
225                 230                 235                 240

Thr Asp Gly Ser Ala Ser Ser Gln Ala Tyr Thr Lys Val Leu Tyr Phe
                245                 250                 255

His Lys Gly Leu Val Ile Lys Glu Glu Ala Leu Lys Gly Ser Ala Arg
            260                 265                 270

His Ile Glu Glu Cys Ser Cys Tyr Gly His Asn Ser Lys Val Thr Cys
        275                 280                 285
```

-continued

```
Val Cys Arg Asp Asn Trp Gln Gly Ala Asn Arg Pro Val Ile Glu Ile
    290                 295                 300

Asp Met Asn Ala Met Glu His Thr Ser Gln Tyr Leu Cys Thr Gly Val
305                 310                 315                 320

Leu Thr Asp Thr Ser Arg Pro Ser Asp Lys Ser Ile Gly Asp Cys Asn
                325                 330                 335

Asn Pro Ile Thr Gly Ser Pro Gly Ala Pro Gly Val Lys Gly Phe Gly
            340                 345                 350

Phe Leu Asp Ser Gly Asn Thr Trp Leu Gly Arg Thr Ile Ser Pro Arg
        355                 360                 365

Ser Arg Ser Gly Phe Glu Met Leu Lys Ile Pro Asn Ala Gly Thr Asp
    370                 375                 380

Pro Asn Ser Arg Ile Thr Glu Arg Gln Glu Ile Val Asp Asn Asn Asn
385                 390                 395                 400

Trp Ser Gly Tyr Ser Gly Ser Phe Ile Asp Tyr Trp Asp Glu Ser Ser
                405                 410                 415

Glu Cys Tyr Asn Pro Cys Phe Tyr Val Glu Leu Ile Arg Gly Arg Pro
            420                 425                 430

Glu Glu Ala Lys Tyr Val Trp Trp Thr Ser Asn Ser Leu Val Ala Leu
        435                 440                 445

Cys Gly Ser Pro Ile Ser Val Gly Ser Gly Ser Phe Pro Asp Gly Ala
    450                 455                 460

Gln Ile Gln Tyr Phe Ser
465                 470
```